(12) United States Patent
Mounce et al.

(10) Patent No.: US 9,199,030 B2
(45) Date of Patent: *Dec. 1, 2015

(54) INFUSION MEDIUM DELIVERY DEVICE AND METHOD WITH DRIVE DEVICE FOR DRIVING PLUNGER IN RESERVOIR

(71) Applicant: Medtronic MiniMed, Inc., Northridge, CA (US)

(72) Inventors: R. Paul Mounce, Burbank, CA (US); Melissa D. Norton, Valencia, CA (US); Paul F. Bente, IV, Wayne, PA (US); Ian B. Hanson, Wayne, CA (US); Sheldon B. Moberg, Thousand Oaks, CA (US); Paul H. Kovelman, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 13/971,771

(22) Filed: Aug. 20, 2013

(65) Prior Publication Data

US 2013/0338584 A1    Dec. 19, 2013

Related U.S. Application Data

(60) Division of application No. 12/497,345, filed on Jul. 2, 2009, now Pat. No. 8,529,553, which is a continuation of application No. 11/759,725, filed on Jun. 7, 2007, now Pat. No. 7,744,589, which is a (Continued)

(51) Int. Cl.
*A61M 5/14* (2006.01)
*A61M 5/142* (2006.01)
(Continued)

(52) U.S. Cl.
CPC ......... *A61M 5/1413* (2013.01); *A61M 5/14244* (2013.01); *A61M 5/14248* (2013.01);
(Continued)

(58) Field of Classification Search
CPC .......... A61M 5/1413; A61M 5/14236; A61M 5/14244; A61M 5/14248; A61M 5/1456; A61M 2005/14268; A61M 2005/14573; A61M 2205/0272
See application file for complete search history.

(56) References Cited

U.S. PATENT DOCUMENTS 1,948,982 A    2/1934    Cutter
2,064,815 A    12/1936   Armstrong
(Continued)

FOREIGN PATENT DOCUMENTS

DE    1020040 55 870 U1    5/2006
DE    2020070 06 363 U1    8/2007
(Continued)

OTHER PUBLICATIONS

US Office Action dated Nov. 6, 2014, from related U.S. Appl. No. 12/411,236.
(Continued)

*Primary Examiner* — Andrew Gilbert
(74) *Attorney, Agent, or Firm* — Foley & Lardner LLP

(57) ABSTRACT

A delivery device includes first and second housing portions that selectively engage and disengage. A reservoir on one housing portion operatively engages a drive device and/or a needle inserting device on the other housing portion. Upon proper engagement of the housing portions, the reservoir operatively couples to the drive device and/or the needle inserting device. A first magnet on the first housing portion and a second magnet (or a magnetically-attractive material) on the second housing portion are positioned to magnetically interact with each other, upon operative engagement of the housing portions. A third magnet on the second housing portion may be opposed to the first magnet to help align the housing portions for connection. A magnet-responsive device may be on one or both housing portions to detect alignment and/or connection of the housing portions.

20 Claims, 21 Drawing Sheets

Related U.S. Application Data continuation-in-part of application No. 11/604,172, filed on Nov. 22, 2006, now Pat. No. 8,277,415, which is a continuation-in-part of application No. 11/588,832, filed on Oct. 27, 2006, now Pat. No. 7,905,868, which is a continuation-in-part of application No. 11/515,225, filed on Sep. 1, 2006, now Pat. No. 8,512,288.

(60) Provisional application No. 60/839,822, filed on Aug. 23, 2006.

(51) Int. Cl.
*A61M 5/145* (2006.01)
*A61M 5/50* (2006.01)

(52) U.S. Cl.
CPC .......... *A61M5/1456* (2013.01); *A61M 5/14236* (2013.01); *A61M 5/14526* (2013.01); *A61M 5/5086* (2013.01); *A61M 2005/14268* (2013.01); *A61M 2005/14573* (2013.01); *A61M 2205/0266* (2013.01); *A61M 2205/103* (2013.01); *A61M 2205/58* (2013.01); *A61M 2205/6054* (2013.01); *Y10T 29/49826* (2015.01)

(56) References Cited

U.S. PATENT DOCUMENTS

| | | | |
|---|---|---|---|
| 2,570,625 A * | 10/1951 | Zimmerman et al. | .......... 446/92 |
| 2,627,857 A | 2/1953 | Marcelli | |
| 2,644,450 A | 7/1953 | Krewson | |
| 2,734,504 A | 2/1956 | Crescas et al. | |
| RE24,918 E | 1/1961 | Mills | |
| 2,973,758 A | 3/1961 | Murrish | |
| 3,223,289 A | 12/1965 | Bouet | |
| 3,342,180 A | 9/1967 | Ellsworth et al. | |
| 3,343,422 A | 9/1967 | McSmith | |
| 3,572,552 A | 3/1971 | Guinn | |
| 3,623,474 A | 11/1971 | Heilman et al. | |
| 3,650,093 A | 3/1972 | Rosenberg | |
| 3,662,753 A | 5/1972 | Tassell | |
| 3,729,032 A | 4/1973 | Tischlinger et al. | |
| 3,802,430 A | 4/1974 | Schwebel et al. | |
| 3,807,119 A | 4/1974 | Shields | |
| 3,963,151 A | 6/1976 | North, Jr. | |
| 3,993,061 A | 11/1976 | O'Leary | |
| 4,064,879 A | 12/1977 | Leibinsohn | |
| 4,117,841 A | 10/1978 | Perrotta et al. | |
| 4,215,701 A | 8/1980 | Raitto | |
| 4,219,055 A | 8/1980 | Wright | |
| 4,234,108 A | 11/1980 | Diamond | |
| 4,373,535 A | 2/1983 | Martell | |
| 4,392,850 A | 7/1983 | Elias et al. | |
| 4,411,662 A | 10/1983 | Pearson | |
| 4,434,820 A | 3/1984 | Glass | |
| 4,447,225 A | 5/1984 | Taff et al. | |
| 4,448,206 A | 5/1984 | Martell | |
| 4,493,704 A | 1/1985 | Beard et al. | |
| 4,508,532 A | 4/1985 | Drews et al. | |
| 4,568,336 A | 2/1986 | Cooper | |
| 4,572,210 A | 2/1986 | McKinnon | |
| 4,585,435 A | 4/1986 | Vaillancourt | |
| 4,684,365 A | 8/1987 | Reinicke | |
| 4,684,366 A | 8/1987 | Denny et al. | |
| 4,703,763 A | 11/1987 | McAlister et al. | |
| 4,743,249 A | 5/1988 | Loveland | |
| 4,744,955 A | 5/1988 | Shapiro | |
| 4,749,109 A | 6/1988 | Kamen | |
| 4,759,756 A | 7/1988 | Forman et al. | |
| 4,865,592 A | 9/1989 | Rycroft | |
| 4,883,101 A | 11/1989 | Strong | |
| 4,913,703 A | 4/1990 | Pasqualucci et al. | |
| 4,936,841 A | 6/1990 | Aoki et al. | |
| 4,957,637 A | 9/1990 | Cornell | |
| 4,986,820 A | 1/1991 | Fischer | |
| 4,994,034 A | 2/1991 | Botich et al. | |
| 5,045,096 A | 9/1991 | Quang et al. | |
| 5,049,129 A | 9/1991 | Zdeb et al. | |
| 5,070,884 A | 12/1991 | Columbus et al. | |
| 5,115,948 A | 5/1992 | Johnson | |
| 5,219,099 A | 6/1993 | Spence et al. | |
| 5,275,582 A | 1/1994 | Wimmer | |
| 5,284,570 A | 2/1994 | Savage et al. | |
| 5,292,318 A | 3/1994 | Haber et al. | |
| 5,295,967 A | 3/1994 | Rondelet et al. | |
| 5,308,333 A | 5/1994 | Skakoon | |
| 5,312,364 A | 5/1994 | Jacobs | |
| 5,329,976 A | 7/1994 | Haber et al. | |
| 5,367,891 A * | 11/1994 | Furuyama | ...................... 63/29.2 |
| 5,385,559 A | 1/1995 | Mannix | |
| 5,387,450 A | 2/1995 | Stewart | |
| 5,407,434 A | 4/1995 | Gross | |
| 5,409,236 A | 4/1995 | Therrien | |
| 5,496,285 A | 3/1996 | Schumacher et al. | |
| 5,533,964 A | 7/1996 | Halperin et al. | |
| 5,647,851 A | 7/1997 | Pokras | |
| 5,651,373 A | 7/1997 | Mah | |
| 5,697,916 A | 12/1997 | Schraga | |
| 5,820,622 A | 10/1998 | Gross et al. | |
| 5,865,803 A | 2/1999 | Major | |
| 5,873,859 A | 2/1999 | Muntz | |
| 5,887,752 A | 3/1999 | Strother | |
| 5,933,287 A * | 8/1999 | Muller | .......... 359/819 |
| 5,954,697 A | 9/1999 | Srisathapat et al. | |
| 6,019,745 A | 2/2000 | Gray | |
| 6,042,565 A | 3/2000 | Hirschman et al. | |
| 6,067,906 A | 5/2000 | Ryan et al. | |
| 6,117,107 A | 9/2000 | Chen | |
| 6,126,643 A | 10/2000 | Vaillancouert | |
| 6,229,584 B1 * | 5/2001 | Chuo et al. | ...................... 349/58 |
| 6,248,093 B1 | 6/2001 | Moberg | |
| 6,253,804 B1 | 7/2001 | Safabash | |
| 6,277,095 B1 | 8/2001 | Kriesel et al. | |
| 6,315,754 B1 | 11/2001 | Daoud et al. | |
| 6,364,866 B1 | 4/2002 | Furr et al. | |
| 6,375,047 B1 | 4/2002 | Herda et al. | |
| 6,423,035 B1 | 7/2002 | Das | |
| 6,450,993 B1 | 9/2002 | Lin | |
| 6,453,956 B2 | 9/2002 | Safabash | |
| 6,461,329 B1 | 10/2002 | Van Antwerp et al. | |
| 6,474,375 B2 | 11/2002 | Spero et al. | |
| 6,478,771 B1 | 11/2002 | Lavi et al. | |
| 6,479,587 B1 | 11/2002 | Stockinger et al. | |
| 6,485,465 B2 | 11/2002 | Moberg et al. | |
| 6,503,225 B1 | 1/2003 | Kirsch et al. | |
| 6,551,285 B1 | 4/2003 | Bierman | |
| 6,572,600 B1 | 6/2003 | Roe et al. | |
| 6,591,876 B2 | 7/2003 | Safabash | |
| 6,595,956 B1 | 7/2003 | Gross et al. | |
| 6,626,874 B1 | 9/2003 | Duchamp | |
| 6,641,566 B2 | 11/2003 | Douglas et al. | |
| 6,656,147 B1 | 12/2003 | Gertsek et al. | |
| 6,656,159 B2 | 12/2003 | Flaherty | |
| 6,716,195 B2 | 4/2004 | Nolan et al. | |
| 6,719,734 B1 | 4/2004 | Harkless | |
| 6,749,587 B2 | 6/2004 | Flaherty | |
| 6,752,180 B2 | 6/2004 | Delay | |
| 6,796,965 B2 | 9/2004 | Dumaresq-Lucas et al. | |
| 6,854,620 B2 | 2/2005 | Ramey | |
| 6,886,724 B2 * | 5/2005 | Hung | ...................... 224/163 |
| 6,918,887 B1 | 7/2005 | Gremel et al. | |
| 6,948,522 B2 | 9/2005 | Newbrough et al. | |
| 7,008,399 B2 | 3/2006 | Larsen et al. | |
| 7,041,082 B2 | 5/2006 | Blomquist et al. | |
| 7,077,835 B2 | 7/2006 | Robinson et al. | |
| 7,220,889 B2 | 5/2007 | Sigurjonsson et al. | |
| 7,306,578 B2 | 12/2007 | Gray et al. | |
| 7,338,472 B2 | 3/2008 | Shearn | |
| 7,361,156 B2 | 4/2008 | Joyce et al. | |
| 7,399,484 B2 | 7/2008 | Ellefson et al. | |
| 7,507,221 B2 | 3/2009 | Neer | |
| 7,540,863 B2 | 6/2009 | Haindl | |
| 7,621,429 B2 | 11/2009 | Wu et al. | |

(56) References Cited

U.S. PATENT DOCUMENTS

| | | | |
|---|---|---|---|
| 7,686,787 B2 | 3/2010 | Moberg et al. | |
| 7,708,717 B2 | 5/2010 | Estes et al. | |
| 7,744,589 B2 * | 6/2010 | Mounce et al. | 604/890.1 |
| 7,794,427 B2 * | 9/2010 | Estes et al. | 604/151 |
| 7,858,112 B2 | 12/2010 | Hatanaka et al. | |
| 7,955,305 B2 | 6/2011 | Moberg et al. | |
| 7,981,085 B2 | 7/2011 | Ethelfeld | |
| 8,034,026 B2 | 10/2011 | Grant et al. | |
| 8,337,486 B2 * | 12/2012 | Yodfat et al. | 604/890.1 |
| 8,360,114 B2 | 1/2013 | Clark | |
| 8,409,143 B2 | 4/2013 | Lanigan et al. | |
| 8,529,553 B2 * | 9/2013 | Mounce et al. | 604/890.1 |
| 2002/0104584 A1 | 8/2002 | Spero et al. | |
| 2002/0169439 A1 | 11/2002 | Flaherty | |
| 2003/0023206 A1 | 1/2003 | Bausmith et al. | |
| 2003/0040714 A1 | 2/2003 | Coss | |
| 2003/0050607 A1 | 3/2003 | Gagnieux et al. | |
| 2003/0104032 A1 | 6/2003 | Sawhney et al. | |
| 2003/0199825 A1 | 10/2003 | Flaherty | |
| 2003/0233069 A1 | 12/2003 | Gillespie et al. | |
| 2004/0116866 A1 | 6/2004 | Gorman | |
| 2004/0140327 A1 | 7/2004 | Osborne et al. | |
| 2004/0149349 A1 | 8/2004 | D'Antonio et al. | |
| 2004/0158207 A1 | 8/2004 | Hunn et al. | |
| 2004/0199140 A1 | 10/2004 | Rue et al. | |
| 2005/0101920 A1 | 5/2005 | Keane et al. | |
| 2005/0119618 A1 | 6/2005 | Gonnelli | |
| 2005/0137530 A1 | 6/2005 | Campbell et al. | |
| 2005/0240159 A1 | 10/2005 | Kito et al. | |
| 2006/0106360 A1 | 5/2006 | Wong | |
| 2006/0184103 A1 | 8/2006 | Paproski et al. | |
| 2006/0200073 A1 | 9/2006 | Radmer et al. | |
| 2006/0264894 A1 | 11/2006 | Moberg et al. | |
| 2007/0073235 A1 * | 3/2007 | Estes et al. | 604/151 |
| 2007/0079894 A1 | 4/2007 | Kraus et al. | |
| 2007/0244444 A1 | 10/2007 | Guelker et al. | |
| 2007/0293826 A1 * | 12/2007 | Wall et al. | 604/200 |
| 2008/0051710 A1 | 2/2008 | Moberg et al. | |
| 2008/0161772 A1 | 7/2008 | Nayak et al. | |
| 2008/0172024 A1 | 7/2008 | Yow | |
| 2008/0215030 A1 | 9/2008 | Ritsher | |
| 2008/0249498 A1 | 10/2008 | Fangrow | |
| 2008/0257916 A1 | 10/2008 | Chang | |
| 2008/0269682 A1 | 10/2008 | Kavazov et al. | |
| 2008/0269687 A1 | 10/2008 | Chong et al. | |
| 2009/0012497 A1 | 1/2009 | Uber et al. | |
| 2009/0206111 A1 | 8/2009 | Conrardy et al. | |
| 2009/0243283 A1 | 10/2009 | Schilp et al. | |
| 2010/0094241 A1 | 4/2010 | Remde et al. | |
| 2010/0298768 A1 | 11/2010 | Halili et al. | |
| 2011/0160654 A1 | 6/2011 | Hanson et al. | |
| 2011/0282316 A1 | 11/2011 | Stepovich et al. | |
| 2012/0004602 A1 | 1/2012 | Hanson et al. | |
| 2012/0053520 A1 * | 3/2012 | Kirkpatrick | 604/151 |
| 2015/0011971 A1 | 1/2015 | Lee | |

FOREIGN PATENT DOCUMENTS

| | | |
|---|---|---|
| EP | 1 462 134 | 9/2004 |
| EP | 1 527 792 | 5/2005 |
| FR | 1496026 | 9/1967 |
| GB | 1 452 104 | 10/1976 |
| GB | 2 176 711 | 1/1987 |
| GB | 2 207 652 | 2/1989 |
| WO | WO-95/32015 | 11/1995 |
| WO | WO-96/26702 | 9/1996 |
| WO | WO-97/44078 | 11/1997 |
| WO | WO-97/46203 | 12/1997 |
| WO | WO-99/48546 | 9/1999 |
| WO | WO-99/59665 | 11/1999 |
| WO | WO-00/47254 | 8/2000 |
| WO | WO-00/69488 | 11/2000 |
| WO | WO-02/02165 | 1/2002 |
| WO | WO-03/006090 | 1/2003 |
| WO | WO-03/026728 | 4/2003 |
| WO | WO-03/072172 | 9/2003 |
| WO | WO-2004/006981 | 1/2004 |
| WO | WO-2004/047641 | 6/2004 |
| WO | WO-2004/098683 | 11/2004 |
| WO | WO-2004/110526 | 12/2004 |
| WO | WO-2005/000382 | 1/2005 |
| WO | WO-2005/072795 | 8/2005 |
| WO | WO-2005/094920 | 10/2005 |
| WO | WO-2005/097237 | 10/2005 |
| WO | WO-2006/032692 | 3/2006 |
| WO | WO-2006/058435 | 6/2006 |
| WO | WO-2007/038091 | 4/2007 |
| WO | WO-2007/062068 | 5/2007 |
| WO | WO-2007/071255 | 6/2007 |
| WO | WO-2007/087808 | 8/2007 |
| WO | WO-2007/130809 | 11/2007 |
| WO | WO-2008/024614 | 2/2008 |
| WO | WO-2008/093063 | 8/2008 |
| WO | WO-2008/151241 | 12/2008 |

OTHER PUBLICATIONS

US Notice of Allowance dated May 8, 2013, from related U.S. Appl. No. 11/515,225.
US Office Action dated Nov. 21, 2012, from related U.S. Appl. No. 11/515,225.
US Office Action dated Mar. 10, 2010, from related U.S. Appl. No. 11/515,225.
US Office Action dated Oct. 19, 2009, from related U.S. Appl. No. 11/515,225.
US Office Action dated Apr. 9, 2009, from related U.S. Appl. No. 11/515,225.
US Notice of Allowance dated Jan. 26, 2011, from related U.S. Appl. No. 11/588,832.
US Office Action dated Aug. 10, 2010, from related U.S. Appl. No. 11/588,832.
US Office Action dated Mar. 2, 2010, from related U.S. Appl. No. 11/588,832.
US Office Action dated Apr. 10, 2009, from related U.S. Appl. No. 11/588,832.
US Office Action dated Nov. 21, 2008, from related U.S. Appl. No. 11/588,832.
US Notice of Allowance dated Apr. 26, 2010, from related U.S. Appl. No. 11/604,171.
US Office Action dated Mar. 17, 2010, from related U.S. Appl. No. 11/604,171.
US Office Action dated Oct. 9, 2009, from related U.S. Appl. No. 11/604,171.
US Office Action dated Apr. 13, 2009, from related U.S. Appl. No. 11/604,171.
US Office Action dated Nov. 21, 2008, from related U.S. Appl. No. 11/604,171.
US Notice of Allowance dated Aug. 9, 2012, from related U.S. Appl. No. 11/604,172.
US Office Action dated May 28, 2010, from related U.S. Appl. No. 11/604,172.
US Office Action dated Feb. 17, 2010, from related U.S. Appl. No. 11/604,172.
US Office Action dated Jun. 17, 2009, from related U.S. Appl. No. 11/604,172.
US Office Action dated Jan. 29, 2009, from related U.S. Appl. No. 11/604,172.
US Notice of Allowance dated May 14, 2010, from related U.S. Appl. No. 11/759,725.
US Office Action dated Nov. 24, 2008, from related U.S. Appl. No. 11/759,725.
US Notice of Allowance dated Oct. 7, 2011, from related U.S. Appl. No. 11/964,649.
US Office Action dated Mar. 29, 2011, from related U.S. Appl. No. 11/964,649.
US Office Action dated Jan. 7, 2010, from related U.S. Appl. No. 11/964,649.
US Office Action dated Jul. 8, 2009, from related U.S. Appl. No. 11/964,649.

(56) References Cited

OTHER PUBLICATIONS

US Notice of Allowance dated Apr. 1, 2013, from related U.S. Appl. No. 12/111,751.
US Office Action dated Nov. 21, 2012, from related U.S. Appl. No. 12/111,751.
US Office Action dated Jun. 19, 2012, from related U.S. Appl. No. 12/111,751.
US Office Action dated Dec. 29, 2011, from related U.S. Appl. No. 12/111,751.
US Notice of Allowance dated Apr. 20, 2011, from related U.S. Appl. No. 12/111,815.
US Office Action dated Dec. 22, 2010, from related U.S. Appl. No. 12/111,815.
US Notice of Allowance dated Apr. 29, 2011, from related U.S. Appl. No. 12/107,580.
US Office Action dated Dec. 30, 2010 from related U.S. Appl. No. 12/107,580.
US Office Action dated Aug. 18, 2010, from related U.S. Appl. No. 12/107,580.
US Notice of Allowance dated Aug. 21, 2013, from related U.S. Appl. No. 12/099,738.
US Office Action dated May 24, 2013, from related U.S. Appl. No. 12/099,738.
US Office Action dated Dec. 20, 2012, from related U.S. Appl. No. 12/099,738.
US Office Action dated Jun. 7, 2012, from related U.S. Appl. No. 12/099,738.
US Office Action dated Dec. 9, 2010, from related U.S. Appl. No. 12/099,738.
US Office Action dated Jul. 21, 2010, from related U.S. Appl. No. 12/099,738.
US Office Action dated Mar. 4, 2010, from related U.S. Appl. No. 12/099,738.
US Office Action dated Nov. 10, 2009, from related U.S. Appl. No. 12/099,738.
US Notice of Allowance dated Oct. 3, 2012, from related U.S. Appl. No. 12/027,963.
US Office Action dated Oct. 15, 2010, from related U.S. Appl. No. 12/027,963.
US Office Action dated Jun. 16, 2010, from related U.S. Appl. No. 12/027,963.
US Office Action dated Sep. 24, 2009, from related U.S. Appl. No. 12/027,963.
US Office Action dated Apr. 30, 2009, from related U.S. Appl. No. 12/027,963.
US Notice of Allowance dated Mar. 21, 2013, from related U.S. Appl. No. 12/247,945.
US Office Action dated Nov. 26, 2012, from related U.S. Appl. No. 12/247,945.
US Office Action dated Feb. 14, 2012, from related U.S. Appl. No. 12/247,945.
US Office Action dated Aug. 22, 2011, from related U.S. Appl. No. 12/247,945.
US Office Action dated Feb. 23, 2011, from related U.S. Appl. No. 12/411,236.
US Office Action dated Sep. 28, 2010, from related U.S. Appl. No. 12/411,236.
US Office Action dated Oct. 23, 2009, from related U.S. Appl. No. 12/411,236.
US Office Action dated Jul. 10, 2009, from related U.S. Appl. No. 12/411,236.
US Notice of Allowance dated Jul. 27, 2011, from related U.S. Appl. No. 12/411,247.
US Office Action dated Mar. 8, 2011, from related U.S. Appl. No. 12/411,247.
US Office Action dated Oct. 1, 2010, from related U.S. Appl. No. 12/411,247.
US Office Action dated Jan. 14, 2010, from related U.S. Appl. No. 12/411,247.
US Office Action dated Aug. 4, 2009, from related U.S. Appl. No. 12/411,247.
US Notice of Allowance dated Apr. 29, 2013, from related U.S. Appl. No. 12/497,345.
US Office Action dated Oct. 10, 2012, from related U.S. Appl. No. 12/497,345.
US Notice of Allowance dated Jul. 30, 2013, from related U.S. Appl. No. 13/083,512.
US Office Action dated Nov. 28, 2012, from related U.S. Appl. No. 13/083,512.
US Notice of Allowance dated Oct. 21, 2013, from related U.S. Appl. No. 13/163,548.
US Office Action dated May 29, 2013, from related U.S. Appl. No. 13/163,548.
Partial Search Report dated Jan. 2, 2008, from related international application No. PCT/US2007/076474.
International Search Report and Written Opinion dated Feb. 29, 2008, from related international application No. PCT/US2007/076474.
Partial Search Report dated Feb. 18, 2008, from related international application No. PCT/US2007/076679.
International Search Report and Written Opinion dated May 15, 2008, from related international application No. PCT/US2007/076679.
International Search Report and Written Opinion dated Feb. 3, 2009, from related international application No. PCT/US2008/082185.
International Search Report and Written Opinion dated Apr. 28, 2009, from related international application No. PCT/US2008/082186.
International Search Report and Written Opinion dated Jun. 5, 2009, from related international application No. PCT/US2008/082187.
Partial Search Report dated Apr. 19, 2010, from related international application No. PCT/US2008/082193.
International Search Report and Written Opinion dated Jun. 29, 2010, from related international application No. PCT/US2008/082193.
U.S. Office Action Dated May 7, 2015, from related U.S. Appl. No. 13/961,798.
U.S. Notice of Allowance dated May 22, 2015, from related U.S. Appl. No. 13/961,795.

* cited by examiner

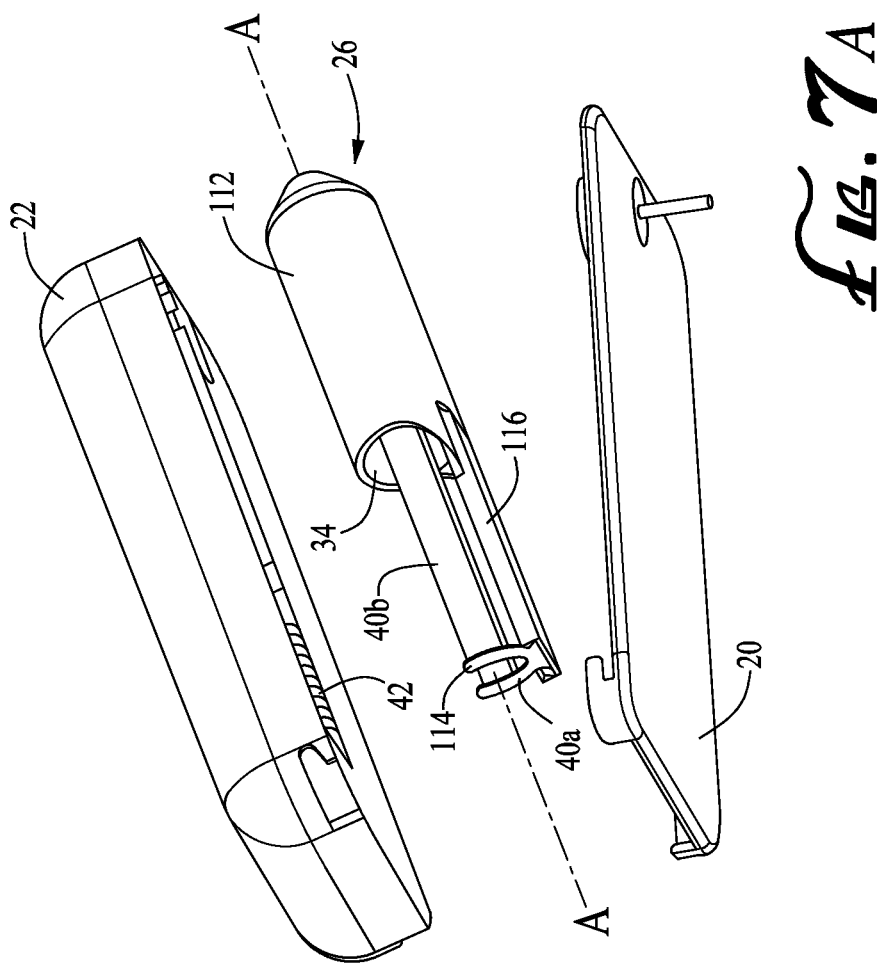

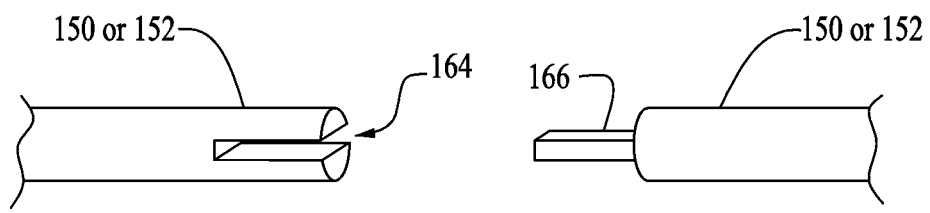
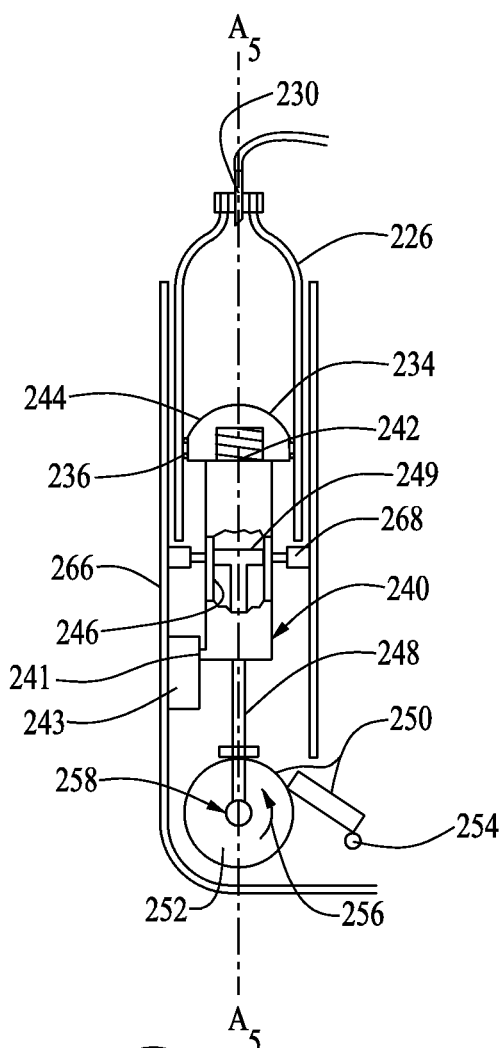
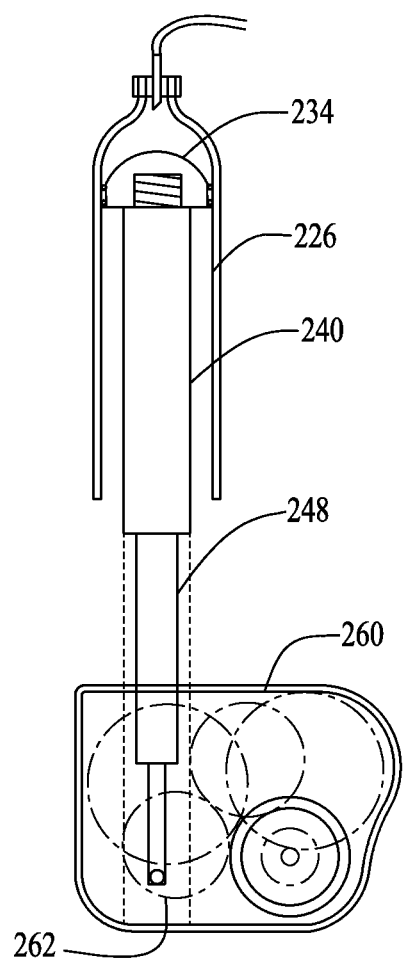

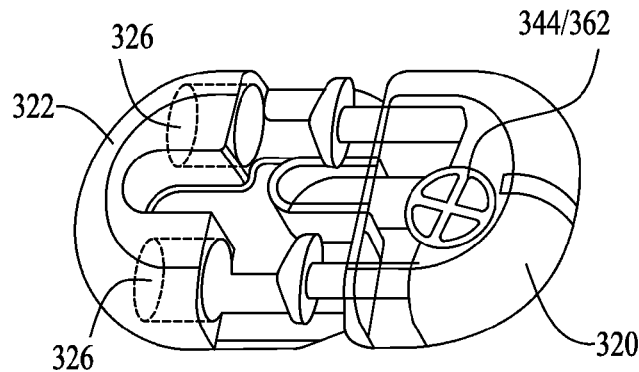
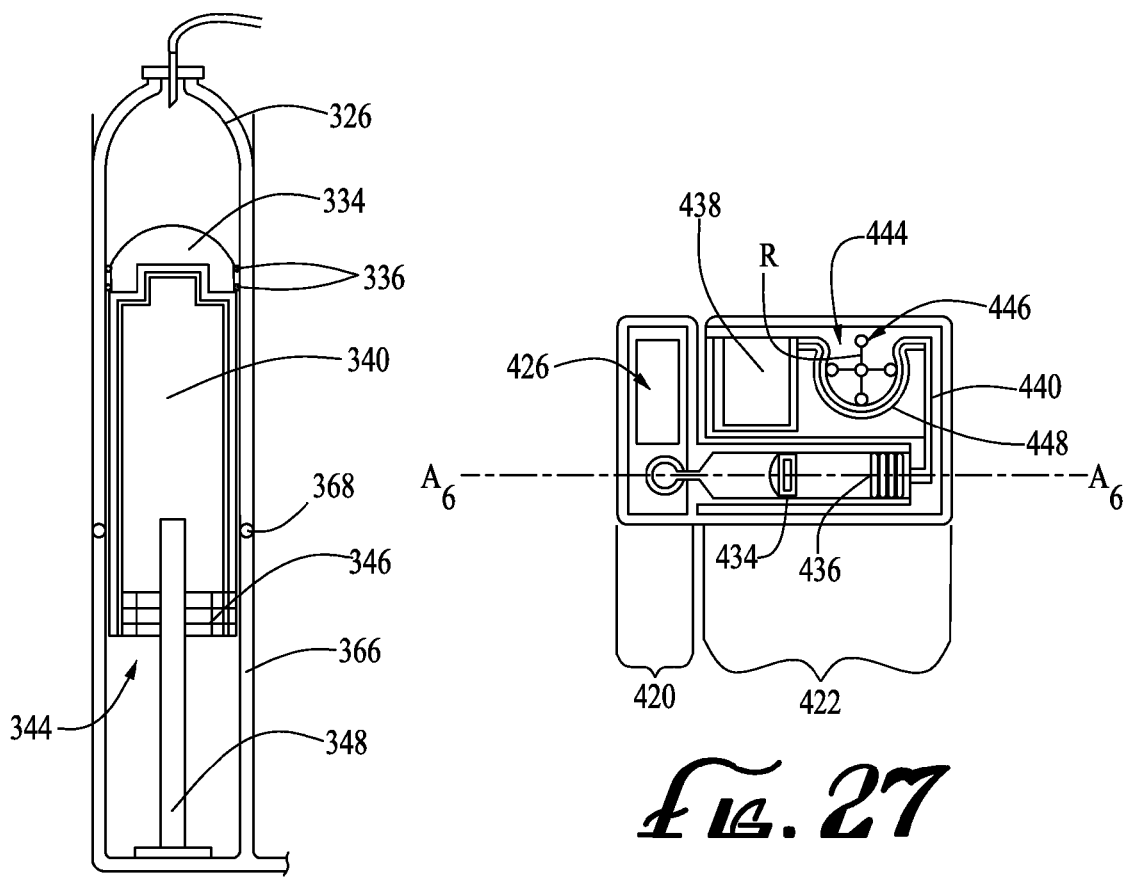

INFUSION MEDIUM DELIVERY DEVICE AND METHOD WITH DRIVE DEVICE FOR DRIVING PLUNGER IN RESERVOIR

CROSS-REFERENCE TO RELATED PATENT APPLICATIONS

This application is a Divisional of U.S. patent application Ser. No. 12/497,345, filed Jul. 2, 2009, incorporated herein by reference in its entirety, which is a Continuation of U.S. patent application Ser. No. 11/759,725, filed Jun. 7, 2007, incorporated herein by reference in its entirety, which is a Continuation-In-Part of U.S. patent application Ser. No. 11/604,172, filed on Nov. 22, 2006, which claims priority to U.S. Provisional Application No. 60/839,822, filed on Aug. 23, 2006 and is a Continuation-In-Part of U.S. patent application Ser. No. 11/588,832, filed on Oct. 27, 2006, which is a Continuation-In-Part of U.S. patent application Ser. No. 11/515,225, filed on Sep. 1, 2006, which claims priority to U.S. Provisional Application 60/839,822, filed on Aug. 23, 2006, each of which is incorporated herein by reference in its entirety. U.S. patent application Ser. No. 11/759,725 of which this application is a Continuation claims priority from U.S. Provisional Application 60/839,822, filed Aug. 23, 2006, and U.S. Provisional Application 60/927,032, filed Apr. 30, 2007, each of which is incorporated herein by reference in its entirety. U.S. patent application Ser. No. 11/759,725 of which this application is a Continuation also relates to U.S. Provisional Patent Application 60/678,290, filed May 6, 2005 and U.S. patent application Ser. No. 11/211,095, filed Aug. 23, 2005, each of which is incorporated herein by reference in its entirety. U.S. patent application Ser. No. 11/759,725 of which this application is a Continuation also relates to U.S. Patent Application No. 60/839,821, entitled "Systems And Methods Allowing For Reservoir Filling And Infusion Medium Delivery," filed Aug. 23, 2006; U.S. Patent Application No. 60/839,832, entitled "Infusion Medium Delivery Device And Method With Compressible Or Curved Reservoir Or Conduit," filed Aug. 23, 2006; U.S. Patent Application No. 60/839,840, entitled "Infusion Medium Delivery System, Device And Method With Needle Inserter And Needle Insert Device And Method," filed Aug. 23, 2006; and U.S. Patent Application No. 60/839,741, entitled "Infusion Pumps And Methods And Delivery Devices And Methods With Same," filed Aug. 23, 2006. U.S. patent application Ser. No. 11/759,725 of which this application is a Continuation also relate to: (i) U.S. patent application Ser. No. 11/604,171, filed Nov. 22, 2006, entitled "Infusion Medium Delivery Device And Method With Drive Device For Driving Plunger In Reservoir"; (ii) U.S. patent application Ser. No. 11/588,875, filed Oct. 27, 2006, entitled "Systems And Methods Allowing For Reservoir Filling And Infusion Medium Delivery"; (iii) U.S. patent application Ser. No. 11/588,847, filed Oct. 27, 2006, entitled "Infusion Medium Delivery Device and Method with Compressible or Curved Reservoir or Conduit"; (iv) U.S. Provisional Patent Application No. 60/854,829, filed Oct. 27, 2006, entitled "Infusion Medium Delivery System, Device and Method with Needle Inserter and Needle Inserter Device and Method"; and (v) U.S. patent application Ser. No. 11/589,323, filed Aug. 23, 2006, entitled "Infusion Pumps and Methods and Delivery Devices and Methods with Same", the contents of each of which are incorporated by reference herein, in their entirety.

FIELD OF THE INVENTION

Embodiments of the present invention relate to an infusion medium delivery device for delivering an infusion medium to a patient-user, where the delivery device includes a base portion and a durable portion connectable to the base portion, where the base portion is securable to a patient-user's skin and can be removed and disposed of after a specified number of uses.

BACKGROUND OF THE INVENTION

Certain chronic diseases may be treated, according to modern medical techniques, by delivering a medication or other substance to a patient's body, either in a continuous manner or at particular times or time intervals within an overall time period. For example, diabetes is a chronic disease that is commonly treated by delivering defined amounts of insulin to the patient at appropriate times. Some common modes of providing an insulin therapy to a patient include delivery of insulin through manually operated syringes and insulin pens. However, other modern systems employ programmable pumps to deliver controlled amounts of insulin to a patient.

Pump type delivery devices have been configured in external devices (that connect to a patient) or implantable devices (to be implanted inside of a patient's body). External pump type delivery devices include devices designed for use in a stationary location (for example, in a hospital or clinic), and further devices configured for ambulatory or portable use (to be carried by a patient). Examples of some external pump type delivery devices are described in Published PCT Application WO 01/70307 (PCT/US01/09139) titled "Exchangeable Electronic Cards For Infusion Devices" (which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle designed to pierce the patient-user's skin and deliver an infusion medium there-through. Alternatively, the hollow tubing may be connected directly to the patient-user as or through a cannula or set of micro-needles.

In contexts in which the hollow tubing is connected to the patient-user through a hollow needle that pierces the patient-user's skin, a manual insertion of the needle into the patient-user can be somewhat traumatic to the patient-user. Accordingly, insertion tools have been made to assist the insertion of a needle into the patient-user, whereby a needle is forced by a spring to quickly move from a retracted position into an extended position. One example of such an insertion tool is described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient-user's skin in a single, relatively abrupt motion that can be less traumatic to a patient-user as compared to a slower, manual insertion of a needle. However, in some contexts, a controlled, slow insertion speed can be less traumatic to some patients.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

SUMMARY OF THE DISCLOSURE

Embodiments of the present invention relate to an infusion medium delivery device for delivering an infusion medium to a patient-user, wherein the delivery device includes a first (or durable) housing portion and a second (or disposable) housing portion that selectively, engage and disengage from each other, for example, by manual force. One or both of the first and second housing portions secures to the patient-user. The disposable housing portion may be disposed of after it has been in use for a prescribed period. Components that normally come into contact with a patient-user and/or with infusion media may be supported by the disposable housing portion for disposal after the prescribed use, while the durable housing portion supports other components such as electronics for controlling the delivery of infusion media.

According to embodiments of the invention, a delivery device includes first and second housing portions as described above and a reservoir located in one of the first or second housing portions. The reservoir has an interior for containing a fluidic medium and a plunger is moveable within the interior of the reservoir along an axial direction of the reservoir. At least one of a drive device and a needle inserting device is supported by the other of the first and second housing portions relative to the housing portion that supports the reservoir, such that upon the first and second housing portions being operatively engaged, the reservoir is operatively coupled to the at least one of a drive device and a needle inserting device. A first pair of magnets includes a first magnet supported on the first housing portion and a second magnet supported on the second housing portion in a position to magnetically interact with the first magnet, upon the first and second housing portions being operatively engaged.

In one embodiment, each of the first and second magnets have a pole that faces a pole of the other of the first and second magnet, when the first and second housing portions are properly aligned and brought together for operative engagement. The facing poles of the first and second magnets are of opposite polarity such that the first and second magnets mutually attract each other upon the first and second housing portions being operatively engaged.

A further embodiment includes a second pair of magnets comprising third and fourth magnets, wherein each of the third and fourth magnets have a pole that faces a pole of the other of the third and fourth magnet when the first and second housing portions are not properly aligned when brought toward each other for operative engagement. The facing poles of the third and fourth magnets are of the same polarity such that the third and fourth magnets mutually repel each other upon the first and second housing portions being improperly aligned when brought toward each other for operative engagement.

In a further embodiment, the third and fourth magnets are positioned relative to each other so as to impart a repelling force directed toward properly aligning the first and second housing portions for operative engagement, when the first and second housing portions are not properly aligned when brought toward each other for operative engagement. The third and fourth magnets are positioned to be laterally offset from each other upon the first and second housing portions being operatively engaged.

In yet a further embodiment, the second pair of magnets includes the first magnet and a third magnet, wherein each of the first and third magnets have a pole that faces a pole of the other of the first and third magnet when the first and second housing portions are not properly aligned and brought toward each other for operative engagement. The facing poles of the first and third magnets are of the same polarity such that the first and third magnets mutually repel each other upon the first and second housing portions being improperly aligned when brought toward each other for operative engagement. The first and third magnets may be positioned relative to each other so as to impart a repelling force directed toward properly aligning the first and second housing portions for operative engagement, when the first and second housing portions are not properly aligned when brought toward each other for operative engagement. The first and third magnets may be positioned laterally offset from each other upon the first and second housing portions being operatively engaged.

In yet a further embodiment, the first and second magnets have a pole that faces a pole of the other of the first and second magnet, when the first and second housing portions are not properly aligned when brought toward each other for operative engagement. In this embodiment, the facing poles of the first and second magnets are of the same polarity such that the first and second magnets mutually repel each other upon the first and second housing portions being improperly aligned when brought toward each other for operative engagement. According to a further aspect of this embodiment, the first and second magnets are positioned relative to each other so as to impart a repelling force directed toward properly aligning the first and second housing portions for operative engagement. Also according to a further aspect of this embodiment, the first and second magnets may be positioned laterally offset from each other upon the first and second housing portions being operatively engaged.

A further embodiment of the present invention relates to a delivery device for delivering an infusion medium to a user, where the delivery device has a first housing portion adapted to be carried by a user, a second housing portion configured to be selectively operatively engaged with and disengaged from the first housing portion, a reservoir supported by one of the first and second housing portions and at least one of a drive device and a needle inserting device supported by the other of the first and second housing portions, as described above. However, this further embodiment includes a first magnet supported on the first housing portion and at least one of a magnetically attractive material and a magnetically-responsive device supported on the second housing portion in a position to magnetically interact with the first magnet, upon the first and second housing portions being operatively engaged.

According to one aspect of such an embodiment, the magnetically responsive device includes a magnetically attractive material that is attracted to the first magnet upon the first and second housing portions being operatively engaged. According to a further aspect of such an embodiment, the magnetically responsive device includes a device that provides a signal or changes a state, upon the first and second housing portions being operatively engaged. In further embodiments, the delivery device may include control electronics operatively coupled to the magnetically-responsive device, for controlling a drive device dependent upon the signal from or state of the magnetically responsive device. The control electronics may be configured to inhibit operation of the drive device unless the signal from or state of the magnetically-responsive device corresponds to the signal or state when the first and second housing portions are operatively engaged.

A further embodiment of the present invention relates to a delivery device for delivering an infusion medium to a user, where the delivery device has a first housing portion adapted to be carried by a user, a second housing portion configured to be selectively operatively engaged with and disengaged from the first housing portion, a reservoir supported by one of the first and second housing portions and at least one of a drive device and a needle inserting device supported by the other of the first and second housing portions, as described above. However, this further embodiment includes a nut member having an open side, the nut member being supported in a fixed relation with a plunger shaft of the reservoir. The nut member has a structure for engaging a threaded lead shaft in any one of a plurality of positions in a first dimension relative to the nut member. The threaded lead shaft is supported by the second housing portion for rotation about a rotary axis. The rotatable lead shaft is supported by the second housing portion in a position to be inserted through the open side of the nut member to threadably engage with the nut member, as the first and second housing portions are brought together for operative engagement. The nut member may be a generally U-shaped member having a pair of arms that are separated by a gap between the arms.

In particular embodiments, the plunger shaft comprises a pair of rods, where each rod extends from the plunger head to one respective arm of the U-shaped member. In yet further embodiments, at least one of the nut member and at least one of the rods includes a detectable feature and the delivery device further includes a sensor arranged to detect the detectable feature to provide a signal corresponding to the position of the detectable feature, where the position of the detectable feature corresponds to a fill state of the reservoir. The detectable feature may include, but is not limited to, a magnetic material. In one embodiment, the nut member is made of a magnetic material.

BRIEF DESCRIPTION OF THE DRAWINGS

FIG. 7a is a partial, exploded, perspective view of a delivery device according to a further embodiment of the present invention.

FIG. 7b is a partial perspective view of a reservoir of the embodiment of FIG. 7a.

FIG. 7c is a generalized top view of a partial nut of the embodiment of FIG. 7a.

FIG. 22 shows a perspective view of an embodiment of connection ends of the drive linkage and the rotatable shaft of FIGS. 17 and 18.

FIGS. 23 and 24 show partial cross-sectional views of reservoirs and drive devices for a delivery device according to further embodiments of the present invention.

FIG. 25 shows a perspective view of a delivery device containing two reservoirs that may employ a drive device according to FIG. 23, 24 or 26 or other suitable drive device.

FIG. 26 shows a schematic cross-sectional view of a reservoir and drive device for a delivery device according to a further embodiment of the present invention.

FIG. 27 shows a schematic view of a delivery device according to a further embodiment of the present invention.

DETAILED DESCRIPTION

The present invention relates, generally, to delivery devices, systems and methods for delivering an infusion medium, such as a drug, to a recipient, such as a medical patient-user. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient-user for delivery of a fluidic infusion medium to the patient-user.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Figure 1:
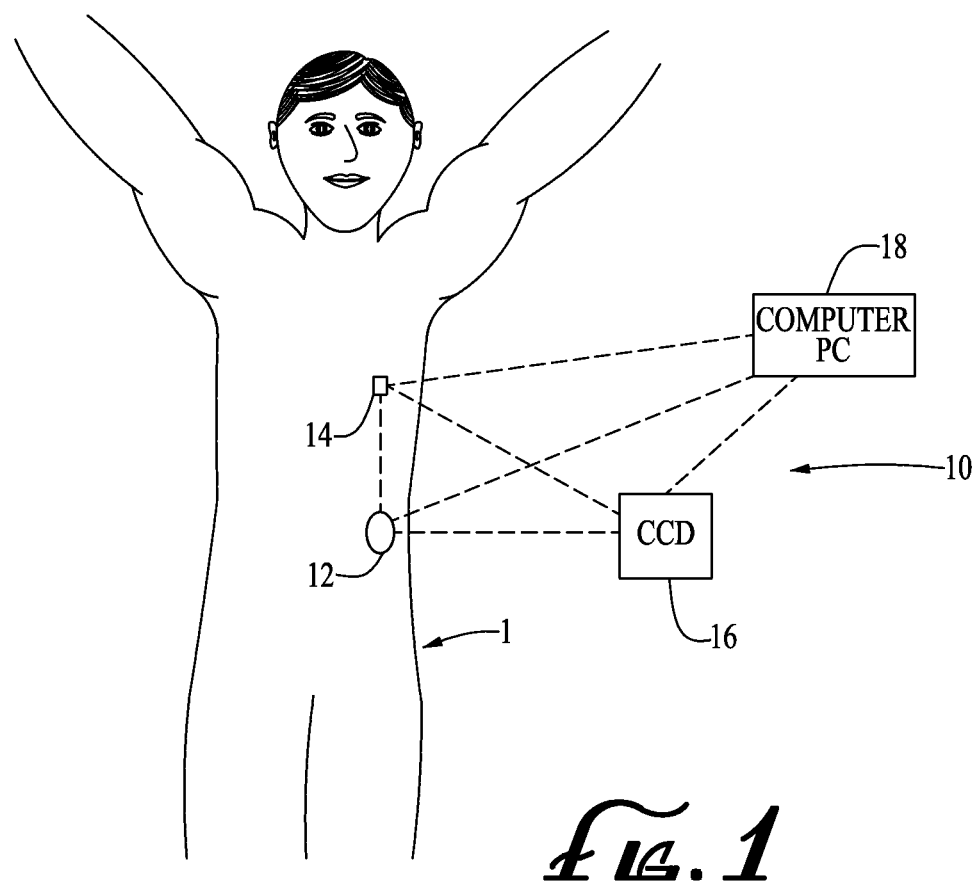
FIG. 1 is a generalized diagram of a delivery system in relation to a human patient-user.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the computer 18, the sensor or monitor 14 and the delivery device 12 may include receiver or transceiver electronics that allow communication with other components of the system. The delivery device 12 may include electronics and software for analyzing sensor data and for delivering an infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may include delivery device 12 that operates without any one or more of the other components of the system 10 shown in FIG. 1. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1, and such locations may depend upon the type of treatment to be administered by the system 10. Such other locations may include, but are not limited to, other locations on the patient-user's body, locations on the patient-user's clothing, belt, suspenders, straps, purse, tote or other structure that may be carried by the patient-user. Thus, while embodiments are described herein with reference to a patch-like device that secures to the patient-user's skin, other embodiments may be configured as portable devices that may be carried by the user, for example, by securing the device to an article of the user's clothing or providing additional securing structure, such as straps, tie strings, or the like, to secure to the patient-user or the patient-user's clothing or the like.

As described in further detail below, the delivery device 12 contains a reservoir of an infusion medium and delivers the infusion medium into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal, for example, under a garment.

Examples of patch-like delivery devices are described in U.S. patent application Ser. No. 11/211,095, filed Aug. 23, 2005, which is incorporated herein, in its entirety. A further example of a patch-like delivery device 12 is shown in FIGS. 2-5 herein. The delivery device 12 in FIGS. 2 and 3 includes a first housing portion 20 that, in some embodiments, may be disposable after one or a number of specified uses, and a second housing portion 22 that, in some embodiments, may be a durable housing portion cable of multiple usages. The disposable housing portion 20 may support structural elements that ordinarily contact the patient-user's skin or the infusion medium, during operation of the delivery device 12.

On the other hand, the durable housing portion 22 may support elements (including electronics, motor components, linkage components, and the like) that do not ordinarily contact the patient-user or the infusion medium during operation of the delivery device 12. Thus, elements in the durable portion 22 of the delivery device 12 are typically not contaminated from contact with the patient-user or the infusion medium during normal operation of the delivery device 12.

In the illustrated embodiment, the disposable portion 20 of the delivery device 12 includes a base 21 that includes or otherwise supports a reservoir retaining portion 24 that houses a reservoir. The durable portion 22 may include a housing that secures onto the base 21 adjacent the reservoir retaining portion 24. The durable portion 22 may house a suitable drive device, such as an electrically operated motor (not shown in FIGS. 2 and 3), and drive linkage components (not shown in FIG. 2) for driving fluid out of the reservoir. The durable portion 22 also may house suitable control electronics (not shown in FIGS. 2 and 3) for controlling the operation of the drive device to drive fluid from the reservoir in a controlled manner. Further embodiments may include communication electronics (not shown in FIGS. 2 and 3) within the durable portion 22, for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base portion 21, with a peelable cover layer 23 covering the adhesive material. In this manner, a patient-user may peel off the cover layer 23 to expose the adhesive material and then place the adhesive side of the base 21 against the patient-user's skin.

The disposable portion 20 may include a button or other operator 25 for operating a needle inserter device located within the reservoir retaining portion 24. Alternatively, or in addition, reference number 25 may represent an opening, through which an external needle inserter device may operate. Alternatively, or in addition to an operator or opening 25, the needle inserter device may be activated, through a wireless link, from an external controller, such as the CCD 16, sensor or monitor 14 or computer 18. For such embodiments, the CCD 16, sensor or monitor 14 or computer 18 includes a wireless signal transmitter, while the delivery device includes a receiver for receiving a wireless actuation signal and an electronic actuator that is controlled to actuate the needle inserter device, upon receipt of an actuation signal from the CCD 16, sensor or monitor 14 or computer 18. Examples of suitable needle inserter device are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Alternatively, the reservoir retaining portion may include a suitable opening or port for connecting one end of a hollow tube to the reservoir, while the other end of the hollow tube is connected to a hollow needle for piercing the patient-user's skin and conveying the infusion medium from the reservoir into the patient-user, for example, as described with reference to FIG. 2 of U.S. patent application Ser. No. 11/211, 095, filed Aug. 23, 2005 and/or as described herein with reference to FIG. 29.

The durable portion 22 of the delivery device 12 includes a housing shell configured to mate with and secure to the disposable portion 20. The durable portion 22 and disposable portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and disposable portion 20 may be separated from each other by manually applying sufficient force to unsnap the two parts from each other. In further embodiments, a suitable seal, such as an o-ring seal, may be placed along the peripheral edge of the disposable portion 20 and/or the durable portion 22, so as to provide a seal against water between the disposable portion 20 and the durable portion 22.

The durable portion 22 and disposable portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable portion 20 and the durable portion 22 of the delivery device 12 may be made of any suitable plastic, metal, composite material or the like. The disposable portion 20 may be made of the same type of material or a different material relative to the durable portion 22. The disposable portion and durable portions may be manufactured by injection molding or other molding processes, machining processes or combinations thereof.

The base 21 of the disposable housing portion 20 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable portion 20 and/or the durable portion 22 may include an internal sensor (not shown in FIGS. 2 and 3) for connection to a patient-user, for example, through a needle (not shown in FIGS. 2 and 3) or a set of micro-needles for piercing a patient-user's skin when the disposable portion 20 is secured to a patient-user's skin. In such embodiments, a suitable aperture (not shown in FIGS. 2 and 3) may be formed in the base 21, to allow the passage of the sensor needle or micro-needles, when the sensor needle is extended to pierce a patient-user's skin. Alternatively, or in addition, micro-needles may be arranged on or through the adhesive material on the base 21, to pass through the patient-user's skin, when the base 21 is adhered to the patient-user's skin. Alternatively, the durable portion 22 of the delivery device 12 may be connected to an external sensor 14, through a sensor lead, as described in U.S. patent application Ser. No. 11/211,095, filed Aug. 23, 2005. The sensor may include any suitable biological sensing device, depending upon the nature of the treatment to be administered by the delivery device 12. For example, in the context of delivering insulin to a diabetes patient-user, the sensor 14 may include a blood glucose sensor. Alternatively, or in addition, one or more environmental sensing devices may be included in or on the delivery device 12, for sensing one or more environmental conditions. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may, then, be mated with a new (un-used, user-filled, pre-filled, refurbished, refilled or re-manufactured) disposable portion 20 for further delivery operation with a patient-user.

A reservoir 26 may be supported by the reservoir retaining portion 24 of the disposable portion 20 in any suitable manner. The reservoir 26 may be a hollow internal volume of the reservoir retaining portion 24, such as, but not limited to, a cylindrical-shaped volume as shown in broken lines in FIG. 3. Alternatively, the reservoir 26 may be a cartridge or generally cylindrical canister having a shape and size to be received within a hollow internal volume of the reservoir retaining portion. The reservoir 26 is configured for containing a fluidic infusion medium.

Figure 2:
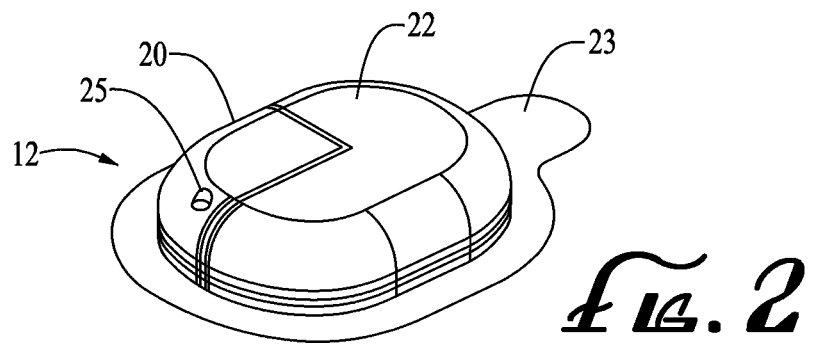
FIG. 2 is a perspective view of a delivery device according to an embodiment of the invention.

The reservoir 26 has a port and a septum. The septum is located in a position at which a hollow needle or cannula may pass through the septum and into a patient-user's skin, when the disposable housing portion 20 is secured to a patient-user's skin, as described below. In other embodiments, the port and septum of the reservoir 26 may be connectable to a patient-user, through an external needle or cannula, through a connector and external tubing, as shown in FIG. 2 of U.S. patent application Ser. No. 11/211,095, filed Aug. 23, 2005, for providing a fluid flow path between the reservoir 26 and the patient-user, when the disposable housing portion 20 is secured to a patient-user's skin. In further embodiments, the port or septum may be used (alternatively or in addition to an outlet port) for filling or re-filling the reservoir 26, for example, but not limited to, inserting a syringe through the septum and passing fluid from the syringe into the reservoir. Examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used.

The durable portion 22 of the delivery device 12 may include a motor or other force-applying mechanism, for applying a force to the infusion medium within the reservoir 26 to force the fluidic infusion medium out of the reservoir 26 and into the hollow needle or cannula (not shown in FIGS. 2 and 3), for delivery to the patient-user. For example, an electrically driven motor may be mounted within the durable portion 22 with appropriate linkage for causing the motor to operably connect to (through the linkage) a piston plunger within the reservoir and drive the piston plunger in a direction to force the fluidic infusion medium out of the reservoir port and into the patient-user. The motor may be arranged within the durable portion 22 and the reservoir 26 may be correspondingly arranged on the disposable portion 20, such that the operable connection of the motor with the reservoir piston (e.g., through appropriate linkage) occurs automatically upon the patient-user snap fitting the durable portion 22 onto the disposable portion 20 of the delivery device 12.

Figure 4:
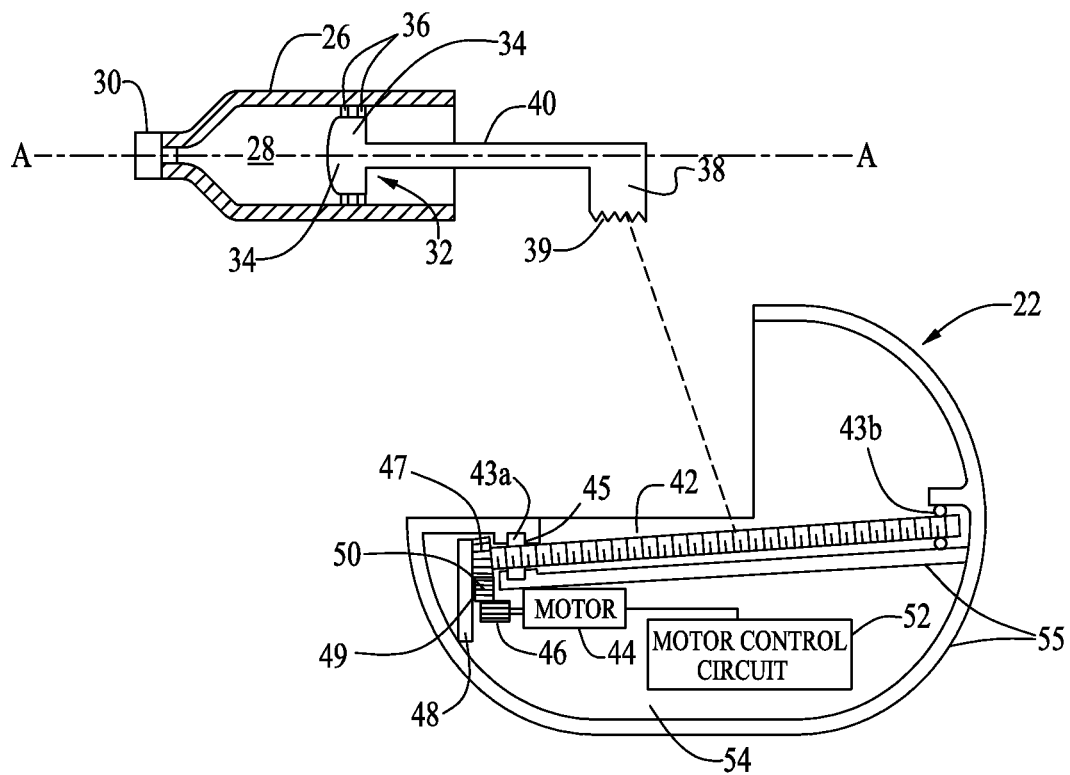
FIG. 4 is a schematic, cross-sectional view of the interior of a reservoir and a durable housing portion of a delivery device according to an embodiment of the invention.

One example of a motor and reservoir configuration is shown in FIG. 4. In the embodiment of FIG. 4, the reservoir 26 (shown in cross-section) is a canister, for example, made of a suitable metal, plastic, ceramic, glass, composite material or the like, and having a hollow interior 28 for containing a fluidic infusion medium. For example, the canister may be formed of a plastic material referred to as TOPAS (trademark of Ticona, a subsidiary of Celanese Corporation), such as described in U.S. patent application Ser. No. 11/100,188, filed Apr. 5, 2005 (Publication No. 2005/0197626), the contents of which is incorporated herein in its entirety.

Figure 3:
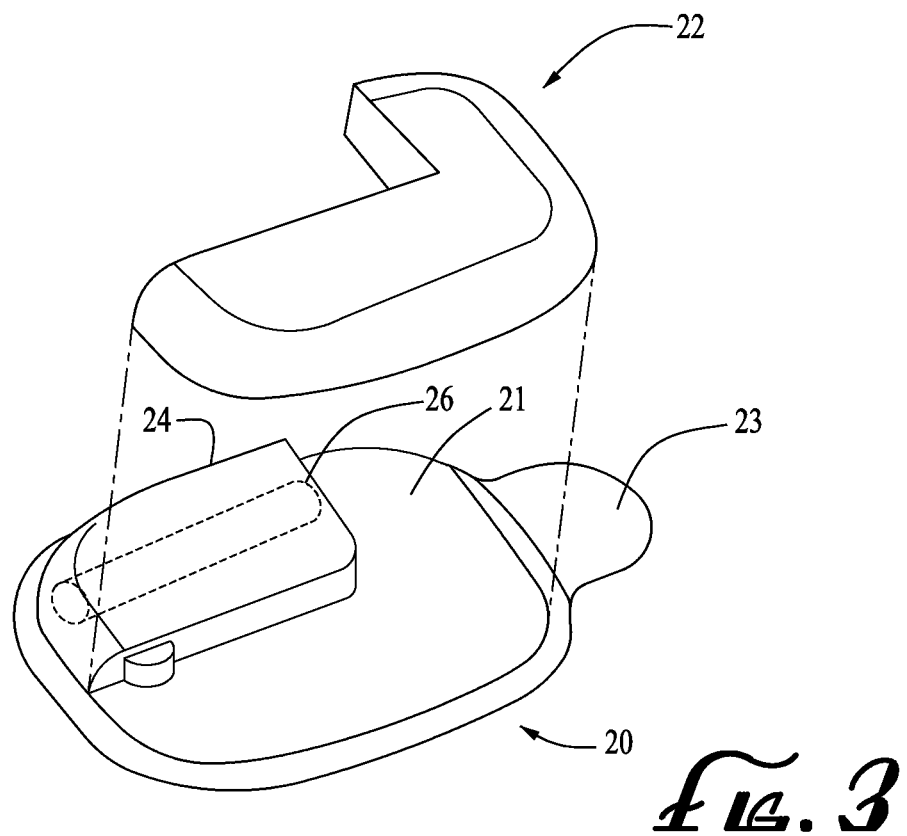
FIG. 3 is a perspective view of a durable portion and a disposable portion of the delivery device of FIG. 2, with the durable portion separated from the disposable portion.

The canister reservoir 26 in FIG. 4 may be configured to fit within and be removable from a correspondingly-shaped opening and volume in the reservoir retaining portion 24 shown in FIG. 3. In such embodiments, the canister reservoir 26 and reservoir retaining portion 24 may include one or more mating protrusions, grooves, indentations and/or non-circular cross-section that restrain the canister reservoir 26 from rotating about the axis A relative to the reservoir retaining portion 24, once the canister reservoir 26 is fitted within the reservoir retaining portion 24. In further embodiments, a canister reservoir 26 may be permanently fixed within the interior volume of the reservoir retaining portion 24.

By supporting a canister reservoir 26 in a manner that allows the reservoir 26 (and piston plunger 32) to be removed and replaced relative to the remainder of the disposable portion 20, a user may replace a spent canister reservoir 26 with a new (un-used, user-filled, pre-filled, refurbished, refilled or re-manufactured) canister reservoir 26 (and piston plunger 32), while the disposable portion remains secured to the patient-user's skin (or otherwise secured to or carried by the patient-user, in contexts in which the housing portions do not adhere to the patient-user's skin). In this manner, the same disposable portion 20 may be used for multiple new reservoirs 26 and, then, disposed of after a prescribed number of unused new, re-filled, user-filled, pre-filled, refurbished or re-manufactured reservoirs have been used on the disposable portion 20, while the same durable portion 22 may be used for multiple disposable portion 20 replacements. This also provides the user with the option to change medication delivery, by changing out and replacing reservoirs 26 with different ones containing either different medications, such as Amilyn, GLP-1, Byetta, Peptide C, insulin sensitizers, combinations of medications (with or without insulin) or the like. Alternatively, the user my change out different types of insulin (e.g., long acting, fast acting, or the like) or utilize different concentrations (U50, U100, U200, U400 or the like).

As described above, in yet further embodiments, the reservoir 26 may be formed unitarily with the reservoir retaining portion 24, for example, as a shaped, hollow interior of the reservoir retaining portion 24. In such embodiments, the hollow interior of the reservoir retaining portion 24 may be coated or otherwise lined with a suitable metal, plastic, plastic, TOPAS (trademark of Ticona, a subsidiary of Celanese Corporation), ceramic, glass, composite material or the like. Alternatively, or in addition, the retaining portion 24, itself, may be made of a suitable metal, plastic, plastic, TOPAS (trademark of Ticona, a subsidiary of Celanese Corporation), ceramic, glass, composite material or the like.

The reservoir 26 includes a septum 30 that can be pierced by a hollow needle or cannula to provide a hollow flow path from the interior 28 of the reservoir 26 to the patient-user. Examples of mechanisms that may be used for moving a hollow needle through a septum of a reservoir are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Alternatively, or in addition, the septum 30 may include a surface that is exposed through a wall of the reservoir retaining portion, for refilling the reservoir 26 or withdrawing infusion medium from the reservoir 26, for example, by piercing the exposed surface of the septum with a syringe, hollow needle or cannula. The septum 30 may be formed of a suitable material, such as, but not limited to, rubber, silicone rubber, polyurethane or other materials that may be pierced by a needle and form a seal around the needle. Examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used.

Figure 5:
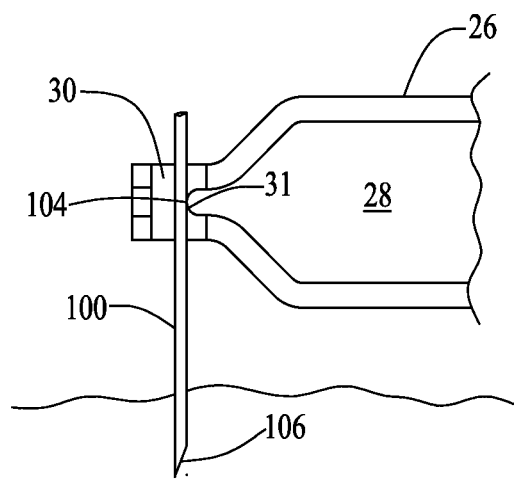
FIG. 5 is a schematic, cross-sectional view of a portion of a reservoir, showing an arrangement of a hollow needle or cannula piercing the reservoir septum and a patient-user's skin.

With reference to FIG. 5, the septum 30 may be configured such that a hollow needle or cannula 100 may be passed through the septum to create a fluid flow path between the interior 28 of the reservoir 26 and a patient-user 1. In particular, when the hollow needle or cannula 100 is passed through the septum 30, a side opening 104 in the hollow needle or cannula 100 may be aligned with a channel or indentation 31 in the septum 30 to form a fluid flow path between the hollow interior of the needle and the interior 28 of the reservoir 26. The hollow needle or cannula 100 includes a patient-end opening 106, to form a fluid flow path between the hollow interior of the needle or cannula 100 and a patient-user 1, upon the sharp end of the needle or an open end of the cannula being inserted in a patient-user's skin. Alternatively, an injection site for inserting a hollow needle or cannula into a patient-user and coupling the needle or cannula in fluid flow communication with the reservoir, as described below with reference to the injection site 132 in FIG. 15, may be employed in the embodiment of FIGS. 1-5. In further embodiments, the injection site may comprise a set of hollow micro-needles arranged to pierce a patient-user's skin, when the disposable housing portion 20 is secured to the patient-user's skin, wherein the micro-needles are connected in fluid-flow communication (for example, through a manifold structure) to the reservoir 26.

Referring again to FIG. 4, a piston plunger 32 is moveable within the interior of the reservoir, for changing the volume of the fluid-containing portion of the interior 28 of the reservoir 26. When a hollow needle or cannula is passed through the septum 30 (or a set of micro-needles are arranged in fluid flow communication with the reservoir) to form a fluid flow path from the reservoir to a patient-user, as described herein, infusion medium inside of the reservoir 26 may be expelled from the reservoir, into the patient-user, in response to a force applied by the piston plunger 32.

The piston plunger 32 extends partially into the interior of the reservoir 26 from the opposite side of the canister relative to the septum 30. The piston plunger 32 may be made of a suitably rigid material, such as but not limited to metal, plastic, ceramic, glass or composite material, and has a head 34 that has an outside diameter of slightly less than the inside diameter of the interior 28 of the reservoir 26. Alternatively, the piston plunger 32 may be made of a compressible material (such as, but not limited to, an elastically compressible plastic, rubber, silicone, or the like) and may be slightly larger in diameter than the inside diameter of the interior 28 of the reservoir 26, so as to be compressed sufficiently to fit within the interior 28 of the reservoir 26. One or more seals, such as but not limited to o-ring type seals 36, may be arranged within annular grooves provided on the piston plunger head 34. The o-ring seals 36 may be made of any suitable material, including, but not limited to rubber, plastic, metal, composite material or the like, where such o-rings provide a sealing function for inhibiting the leakage of infusion medium from the piston-plunger end of the reservoir 26. The materials from which the canister portion of the reservoir 26, piston plunger 32 and seal(s) 36 are made are preferably selected for suitable strength and durability characteristics, as well as compatibility with the infusion medium. Examples of potential piston plunger configurations may be found in U.S. Pat. No. 6,817,990 issued Nov. 16, 2004, and entitled "Improved Fluid Reservoir Piston," which is incorporated herein by reference in its entirety.

The piston plunger 32 and the interior surface of the reservoir 26 may include an anti-rotation structure, such as, but not limited to, one or more mating protrusions, grooves, indentations similar to those described below with respect to FIG. 17 and/or non-circular cross-section that restrain the piston plunger 32 from rotating about the axis A relative to the reservoir 26. Alternatively, the anti-rotation feature may include one or more seals, such as the seal(s) 36, provided that such seal(s) have sufficient frictional resistance with the interior surface of the reservoir 26 to inhibit rotation of the piston plunger 32 about the axis A, relative to the reservoir 26. For embodiments in which one or more protrusions and mating grooves are provided on the piston plunger 32 and interior surface of the reservoir 26, the protrusions and grooves may be formed with sufficiently slowly arched or curved surfaces (instead of abrupt angles or corners), to allow a seal to be readily placed over the surfaces and seal against the piston plunger 32 and interior surface of the reservoir 26. In yet further embodiments, an anti-rotation structure may be provided on the piston shaft 40 and may include any suitable structure for engaging a surface of the durable housing portion 22 or disposable housing portion 20 (or other suitable surface structure supported by the durable housing portion 22 or the disposable housing portion 20) and inhibiting rotation of the piston shaft 40 about the axis A.

The piston plunger 32 in FIG. 4 includes an engagement portion 38, located external to the interior 28 of the reservoir 26 and connected by a plunger shaft 40 to the plunger head 34. The piston plunger 32 is configured to be moveable in the axial direction A of the reservoir 26. The fluid-containing portion of the interior volume 28 of the reservoir 26 varies, with movement of the piston plunger 32 in the axial direction A of the reservoir 26. The engagement portion 38 is provided with keys, key slots or threads 39 (hereinafter referred to as threads) that are configured to operatively engage corresponding key slots, keys or threads (hereinafter, referred to as threads) on a lead shaft 42. As described in more detail below, when the engagement portion 38 is operatively engaged with the lead shaft 42 and a drive motor 44 rotates the lead shaft 42, the piston plunger 32 will move axially within the reservoir 26.

The anti-rotation structure described above inhibits the piston plunger 32 from rotating about the axis A. Accordingly, the piston plunger 32 may be arranged in, and inhibited from rotating away from, a position in which the threaded surface 39 of the engagement portion 38 faces a direction that allows the surface 39 to automatically align with and readily come into operable engagement with the lead shaft 42 when the durable portion 22 and the disposable portion 20 are arranged together for coupling.

The lead shaft 42 may be supported for rotation on the durable portion 22 of the delivery device 12. For example, one or more bearings or other suitable structure may be fixed in the durable portion for supporting the lead shaft 42 for rotation about its longitudinal axis. In the embodiment of FIG. 4, the lead shaft 42 is supported at two locations by two rotary bearings 43a and 43b. In other embodiments, the lead shaft 42 may be supported in more than two locations by more than two bearings or may be supported in a cantilevered fashion at one location by a single bearing 43a or 43b. A portion of the length of the lead shaft 42 may be exposed for engagement with the engagement portion 38 of the piston plunger 32. The lead shaft 42 extends through an opening in the durable portion 22 such that a further portion of the lead shaft 42 is located within the enclosed interior 54 of the durable portion 22, for engagement with drive linkage, as described below. One or more seals 45 may be located around the lead shaft 42, between the exposed portion of the lead shaft and the further portion of the lead shaft located in the durable portion 22. In this manner, the seal(s) 45 may inhibit fluid from entering the opening in the durable portion 22 through which the lead shaft 42 extends. The seal(s) 45 may be made of any suitable seal material, including, but not limited to silicone or other flexible plastic, metal, ceramic, composite material or the like. In further embodiments, the seal(s) 45 may comprise a material and/or seal configuration that provides a liquid-tight seal, but allows the passage of air to allow equalization of pressure between the interior 54 of the durable housing portion 22 and the environment exterior of the durable housing portion 22. In yet other embodiments, a pressure equalization port opening may be provided in any suitable location of the durable housing portion, to provide air-flow communication between the interior 54 and exterior of the durable housing portion. In such embodiments, the air-flow communication port may be covered with a material that allows the passage of air, but inhibits the passage of water or other liquids. Examples of structures that permit air-flow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety.

A drive motor 44 is mechanically coupled to the lead shaft 42, to drive the lead shaft in a rotary motion about its longitudinal axis, in a controlled manner. The motor 44 may be coupled to the lead shaft 42 through one or more suitable gears, belts, chains, drive shafts or other linkage structure. The linkage structure may be configured to provide a torque conversion, for example, to increase torque and decrease rotational speed at the lead shaft, relative to the torque and speed output of the motor 44. Accordingly, the motor 44 may produce relatively high-speed rotational motion, which may be converted through the linkage structure to a lower speed of rotation, but higher torque applied to the lead shaft.

In the embodiment illustrated in FIG. 4, the motor 44 includes a drive gear 46, while the shaft 42 is provided with an engagement gear 47. A linking gear 48 is arranged between the drive gear 46 and the engagement gear 47, to convey rotary drive force from the motor 44 to the shaft 42. The linking gear 48 in FIG. 4 includes hub portion 49 for engaging the drive gear 46, and a main portion 50 for engaging the engagement gear 47. The hub portion 49 is fixed to the main portion 50 and has a smaller diameter than the main portion 50.

In other embodiments, a linking gear 48 may be arranged such that a smaller diameter hub portion engages the engagement gear 47, while a larger diameter main portion engages the drive gear 46. In yet further embodiments, additional gears may be interposed between some or each of the gears 46, 47 and 48, to convey rotational motion from the motor 44 to rotational motion of the lead shaft 42. In yet further embodiments, the linking gear 48 may be eliminated and the drive gear 46 may be arranged to directly engage the engagement gear 47. In yet further embodiments, other linkage structure may be employed to operatively link the motor 44 to the lead shaft 42. Further examples of linkage and control structures may be found in U.S. patent application Ser. No. 09/813,660 filed Mar. 21, 2001, and entitled "Control Tabs For Infusion Devices And Methods Of Using The Same," which is incorporated herein by reference in its entirety.

Figure 6A:
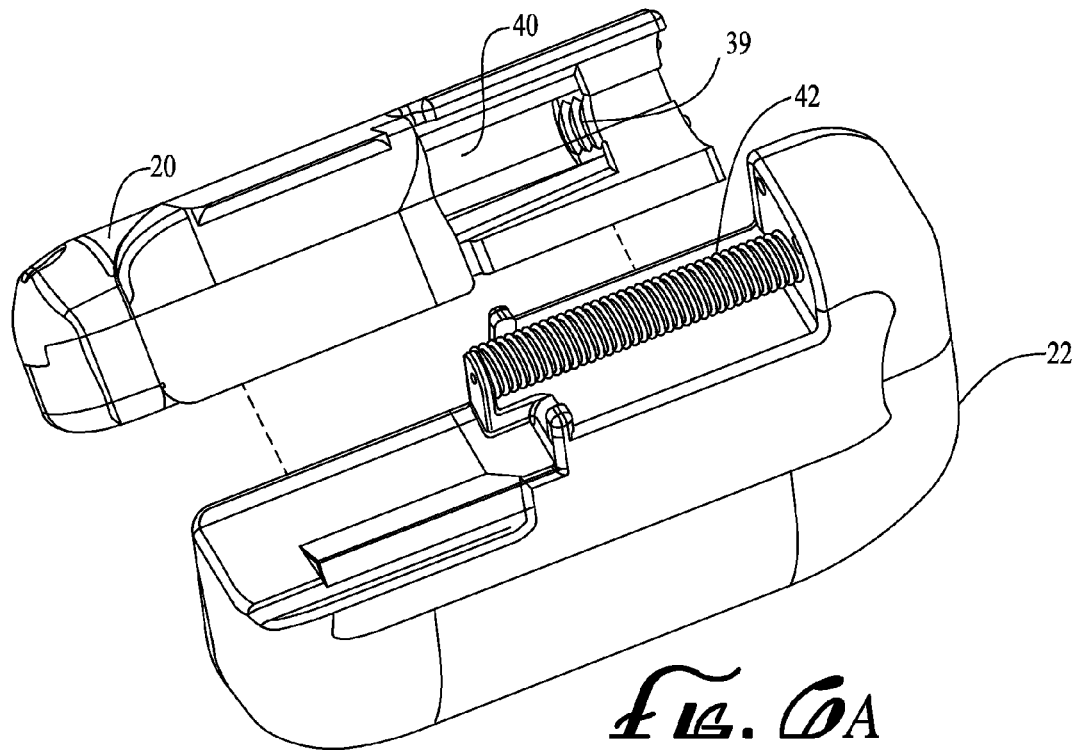
FIG. 6a is a perspective view of a durable portion separated from a disposable portion of a delivery device having a reservoir, piston plunger and lead shaft configuration that engage in a manner similar to that of FIG. 4.
Figure 6B:
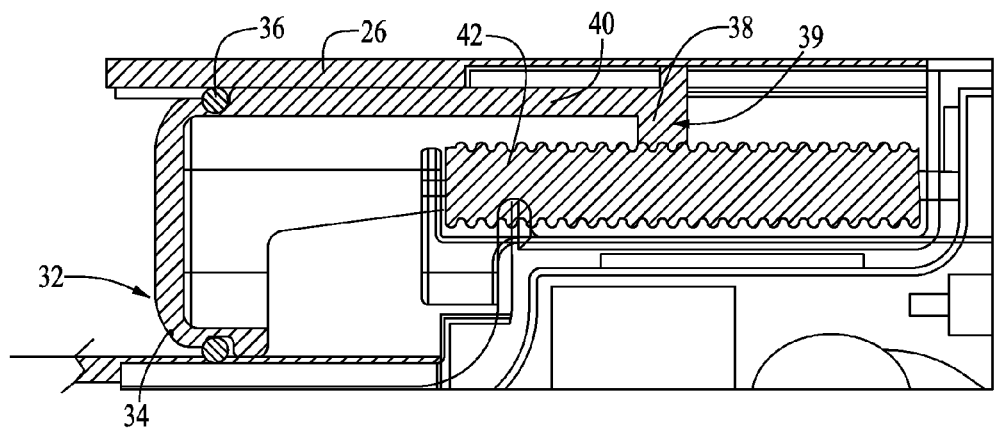
FIG. 6b is a schematic, cross-section view of the piston plunger and lead shaft of FIG. 6, in an engaged state.

FIGS. 6a and 6b show a further example embodiment of delivery device having a piston plunger 32, lead shaft 42 and reservoir 26, similar to piston plunger, lead shaft and reservoir described above with respect to FIG. 4. Referring to FIGS. 6a and 6b, the reservoir 26 may be arranged in a first or disposable housing portion 20 (similar to the disposable housing portion described above), while the lead shaft 42 may be supported by the second or durable housing portion 22 (similar to the durable housing portion described above). In the embodiment in FIGS. 6a and 6b, the piston plunger 32 has a piston head 34 located within the reservoir 26 and a piston shaft 40 that extends from the peripheral edge of the piston head 34 to a location outside of the reservoir 26. One or more seals 36 (for example, similar to seals 36 described above) may be included around the outer peripheral surface of the piston head 34, for sealing against the interior surface of the reservoir 26. A partial-nut engagement portion 38 is provided with threads 39 on a arched surface. The arched surface of the engagement portion 38 curves around the longitudinal axis of the lead shaft 42 to allow the threads 39 to readily operatively engage with threads on the lead shaft 42 as a partial nut (threading partially, but not fully around the shaft), when the disposable housing portion 20 and the durable housing portion 22 are engaged. The arched or curved surface of the threads 39 on the engagement portion 38 allow the engagement portion 38 to easily fit over a portion of the lead shaft 42 and operatively engage the threads on the lead shaft 42 by simply bringing the disposable housing portion 20 and the durable housing portion 22 together in operative engagement.

In FIG. 6a, the disposable housing portion 20 and the disposable housing portion 22 are shown as being separated (for example, just before the disposable housing portion 20 and the durable housing portion 22 are brought together for operative engagement). In FIG. 6b, the disposable housing portion 20 and the durable housing portion 22 are engaged, such that the threads on the engagement portion 38 on the piston plunger 32 is operatively engaged with the threads on the lead shaft 42. The piston plunger 32, including the piston head 34, the piston shaft 40 and the engagement portion 38 may be configured as a single, unitary member, for example, by molding, machining, or other suitable manufacturing technique, for example, for cost-efficiency. Alternatively, the piston plunger 32 may be configured as a multi-piece member that is assembled to form a piston plunger 32.

A further embodiment of a structure for connecting a drive mechanism to a reservoir piston plunger is described with reference to FIGS. 7a, 7b and 7c. For simplifying the present disclosure, components in FIGS. 7a, 7b and 7c that are similar in structure and/or function to components in the above-described embodiments are labeled with corresponding reference numbers in FIGS. 7a, 7b and 7c.

Figures 7B, 7C:
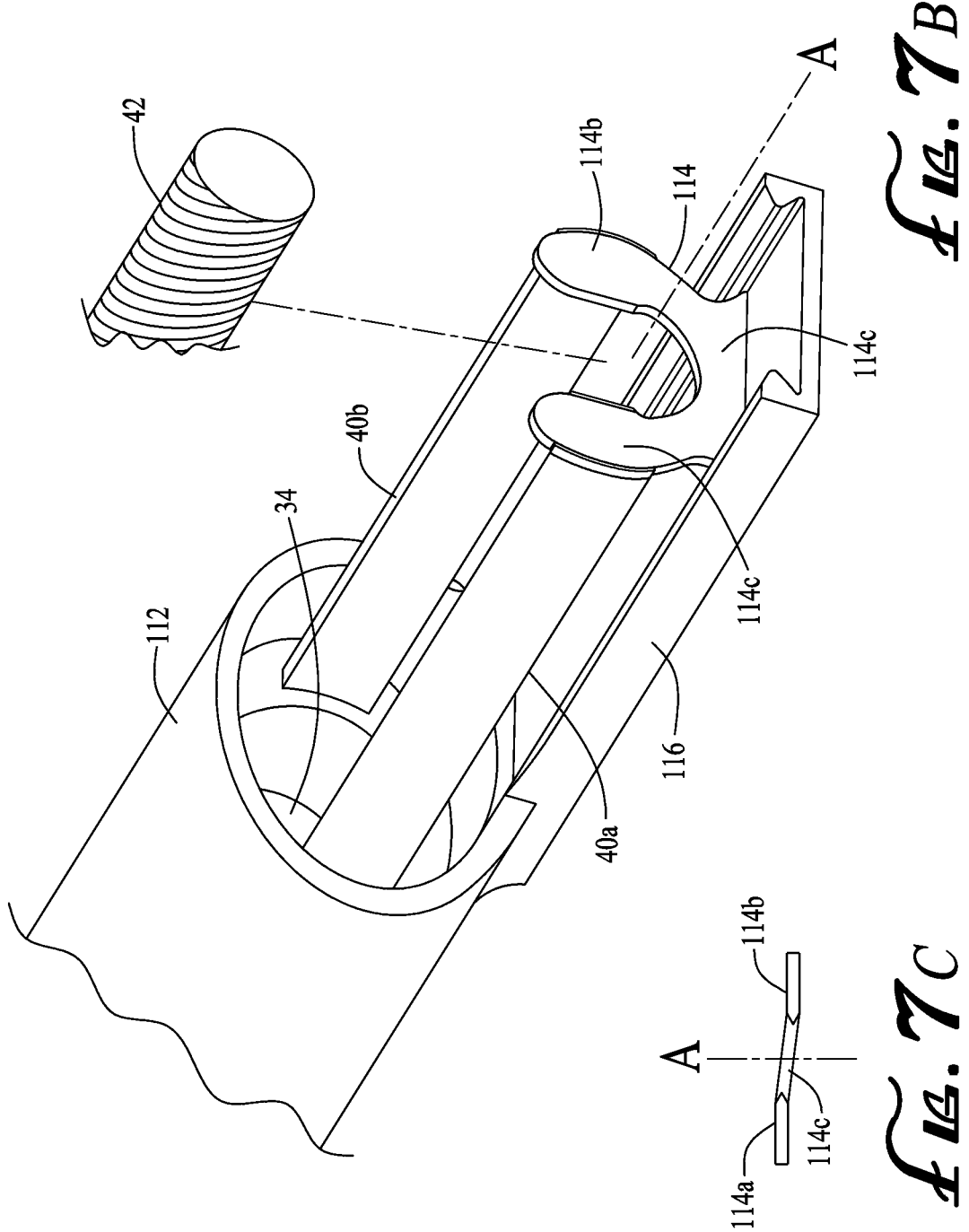

In FIG. 7a, a reservoir 26 has a housing 112 with a hollow interior for containing a fluidic medium, as described above. A plunger head 34 is located within the reservoir housing 112 and is moveable in the axial direction A of the reservoir, to expand or contract the interior volume of the reservoir. In the embodiment of FIGS. 7a, 7b and 7c, the piston shaft 40 is composed of a pair of rods 40a and 40b extend from the plunger head 34, outside of the reservoir housing 112. The rods 40a and 40b function to provide a rigid connection between a U-shaped nut 114 and the plunger 34. The U-shaped nut 114 may be supported by the rods 40a and 40b. Alternatively or in addition, the U-shaped nut 114 may be supported by a guide rail 116 for movement in the axial direction A of the reservoir 26.

In FIG. 7b, the U-shaped nut 114 has a pair of arms 114a and 114b that are connected by a span 114c and form an open channel 114d there-between. In FIG. 7a, the reservoir 26 is configured to be supported on a base of a disposable housing portion 20 (or a separate base member, such as, but not limited to the base portion describe below with respect to parts 21', 450, 456 or the like), with the open side of the channel 114d of the U-shaped nut 114 oriented to face away from the base. A durable housing portion 22 is configured to secure to the base, over the reservoir 26. The durable housing portion 22 contains, among other components described above, a threaded lead shaft 42 that is operatively engaged with a drive device as described above.

In FIG. 7b, the lead shaft 42 is positioned within the durable housing portion 22 at a location at which it will fit within the channel 114d and engage the arms 114a and 114b, upon the durable housing portion 22 being arranged onto the disposable housing portion 20 (or separable base) for connection. The channel 114d of the U-shaped nut 114 may have a sufficient depth to allow engagement of the lead shaft 42 with the arms 114a and 114b at any one of multiple locations of the lead shaft 42 in the vertical dimension in FIG. 7b, for ease of assembly and manufacturing tolerances. In particular embodiments, the placement of the durable housing portion 22 onto the base of the disposable housing portion 20 (or separate base portion) in a position at which the durable housing portion 22 connects to the base of the disposable housing portion 20 (or separate base portion) will also result in an alignment of the drive shaft 42 with the channel 114d of the U-shaped nut 114, so that no additional manipulation of the components are needed to operatively connect the drive shaft 42 to the nut 114.

In FIG. 7b, the arms 114a and 114b of the U-shaped nut 114 may be offset in the axial direction A relative to each other and may be configured to engage threads on the lead shaft 42. As the lead shaft 42 is rotated while engaged with the U-shaped nut 114, the U-shaped nut 114 will be caused to move in the axial direction A. With the U-shaped nut 114 abutted against or connected to one or both of the rods 40a and 40b, movement of the U-shaped nut 114 in the axial direction A is transferred to movement of the rods 40a and 40b and, thus, movement of the plunger head 34 in the axial direction A. Accordingly, when the lead shaft 42 is engaged with the U-shaped nut 114, movement of the reservoir plunger 34 may be selectively carried out and controlled by selectively driving the lead shaft 42.

In yet further embodiments, the U-shaped nut 114 may be made of or otherwise include a magnetic material (or a magnetically attractive material), while the rods 40a and 40b may be made of a non-magnetic material (or a material that is not attracted to magnets). In such embodiments, a magnetically activated switch or magnet detection device (or magnetically attractive material detector) may be provided in a location to detect the position of the U-shaped nut 114, as the nut 114 is moved along the axial direction A. The position of the U-shaped nut 114 corresponds to the fill state of the reservoir 26. Accordingly, the magnetically activated switch or magnet detection device may be connected to suitable control electronics (such as motor control circuit 52 described above with respect to FIG. 4), for determining the fill state of the reservoir 26. The control electronics 52 may be configured to inhibit operation of a drive device 44 (such as shown in FIG. 4), upon detection of a sufficiently depleted state of the reservoir 26.

While in the embodiment described above, the magnetic material (or magnetically attractive material) is of or on the U-shaped nut 114, other embodiments may employ a magnetic material (or magnetically attractive material) on one or more discrete locations along the length of one or both of the rods 40a and 40b, for detection as described above. Also, while the above embodiments employ a magnet material (or magnetically attractive material) for detection, other embodiments may employ other suitably detectable characteristics, such as, but not limited to, other detectable materials, optically detectable indicia or the like (and corresponding detectors) for detection of the position of the U-shaped nut 114 and/or the rods 40a and 40b.

For example, embodiments may employ an electrical coil arranged adjacent the U-shaped nut 114, where the U-shaped nut 114 has or is made of a magnetic material or a ferrous (or other magnetically attractive) material. By arranging the electrical coil in sufficiently close proximity to the U-shaped nut 114 and passing a current though the coil, the position of the U-shaped nut 114 relative to the electrical coil will have a detectable effect on the current in the coil, by inductive or capacitive properties. In this manner, the position of the U-shaped nut 114 and, thus, the position of the plunger head 34 (in the axial direction A) within the reservoir housing 112, can be detected by detection of the effect on the coil current. In other embodiments, one or both of the rods 40a and 40b may include or be made of a magnetic material or a ferrous (or other magnetically attractive) material to operate with a coil in a manner as described above. The coil may be positioned to one side of the U-shaped nut 114 and rods 40a and 40b. Alternatively, the coil may be positioned around the U-shaped nut 114 and rods 40a and 40b, with the axis of the coil arranged parallel to or coaxially with the axis A of the reservoir.

Alternatively or in addition, one or more linear resistors may be employed to provide a position detection function. For example, a linear resistor may be arranged adjacent to the U-shaped nut 114 or on of the rods 40a and 40b. A brush or other sliding or movable conductor may be arranged in a fixed ration to on one of the U-shaped nut 114, rod 40a or rod 40b and in sliding contact with the linear resistor, to slide along the linear resistor as the plunger 34 is moved axially with in the reservoir housing 112. The position of contact between the brush (or sliding or movable conductor) and the linear resistor will determine a resistance value. That resistance value is different with each different position of contact between the brush (or other sliding or movable conductor) and the linear resistor. The control electronics may be configured to determine a plunger position (of the plunger 34 within the reservoir housing 112), based on the resistance value defined by the position of contact between the brush (or sliding or movable conductor) and the linear resistor. In yet other embodiments, a similar function may be provided by reversing the position of the linear resistor and brush (or other sliding or movable conductor). For example, a linear resistor may be included on one or both of the rods 40a or 40b, while a brush (or other sliding or moveable conductor) is fixed relative to the housing 20 or housing 22 and arranged in sliding contact with the linear resistor. A ratio metric measurement may be employed to compensate for environmental effects on the position sensing mechanisms.

Figure 8:
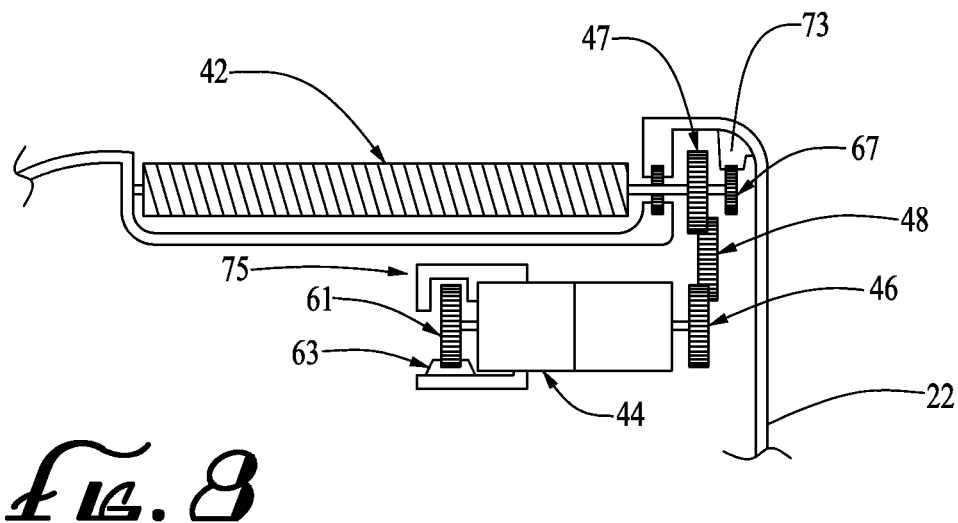
FIG. 8 is a schematic, side view of a motor and linkage structure that may be employed with the embodiments of FIGS. 4, 6 and 7.
Figure 9:
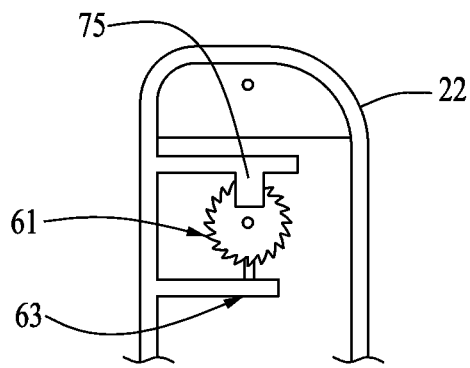
FIG. 9 is a side view of the motor and linkage structure of FIG. 8, as viewed from the left side of FIG. 8.
Figure 10:
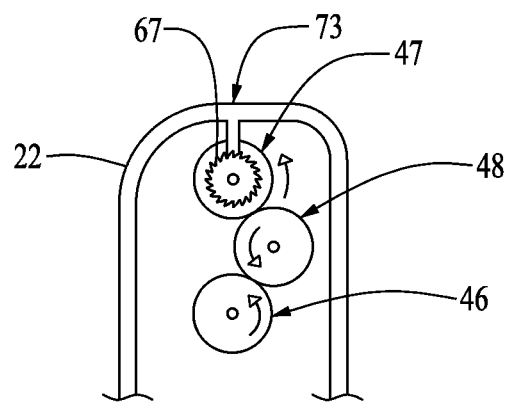
FIG. 10 is a side view of the motor and linkage structure of FIG. 8, as viewed from the right side of FIG. 8.

An example embodiment of a motor 44 and linkage structure for operatively coupling the motor 44 to the lead shaft 42 is shown in FIGS. 8, 9 and 10, where FIG. 9 is a view of the structure of FIG. 8, as viewed from the left side of FIG. 8. Similarly, FIG. 10 is a view of the structure of FIG. 8, as viewed from the right side of FIG. 8. (The orientation of the linkage gears and motor relative to the lead shaft in FIG. 8 is shown as an opposite or a mirror-image of the orientation shown in FIG. 4, but otherwise is structurally similar to the arrangement in FIG. 4.) In the embodiment of FIGS. 8, 9 and 10, one or more of the motor and the linkage structure may be provided with an anti-reverse rotation structure, to inhibit rotation of the lead screw in a direction opposite to the normal drive direction (e.g., opposite to the direction at which the piston plunger is moved to force fluid out of the reservoir). Such anti-reverse rotation structure may include a ratchet wheel and stop surface arrangement.

For example, in the embodiment of FIGS. 8, 9 and 10, the motor 44 is provided with a motor escapement wheel 61 on a common motor drive shaft as the drive gear 46 of the motor. The escapement wheel 61 may include ratchet teeth arranged to ride over a stop surface 63 when the escapement wheel is rotated in the normal drive direction, but that abut the stop surface and inhibit rotation of the motor drive shaft in a direction opposite to the normal drive direction. In a further embodiment, an escapement wheel may be provided in the linkage structure, such as on a common rotary shaft as one of the gears in the linkage structure. In the embodiment in FIGS. 8, 9 and 10, a second escapement wheel 67 is provided on the same rotary shaft of the lead shaft gear 47. A stop surface 73 is arranged relative to the escapement wheel 67 to allow the ratchet teeth on the escapement wheel 67 to ride over the stop surface 73, when the lead shaft 42 is rotated in a normal drive direction, but inhibit rotation of the escapement wheel in a direction opposite to the normal drive direction.

The anti-reverse rotation structure may be provided to inhibit un-intended reverse movement of the piston plunger within the reservoir, for example, due to an improperly aligned motor poles, improper handling of the lead shaft, or the like. A rotation sensor may be associated with either one or both of the escapement wheels 61 and 67. In the embodiment of FIGS. 8, 9 and 10, a rotation sensor in the form of a sensor 75 is arranged adjacent the escapement wheel 61 to sense rotation of the escapement wheel 61. The sensor 75 may be any suitable rotation sensor including, but not limited to an optical sensor for sensing optical elements (reflecting or non-reflecting surface features) on the escapement wheel 61, as the wheel 61 is rotated.

In FIGS. 4 and 6-10, the drive gear 46, the linking gear 47 and engagement gear 48 form a gear train for transferring motor drive force from the motor 44 to the lead shaft 42. In this manner, as the motor rotatably drives the motor drive shaft, the gear train transfers the motor drive force to rotate the lead shaft 42. When the piston plunger 32 is engaged with the lead shaft 42, rotation of the lead shaft 42 causes the engagement portion 38 of the piston plunger 32 to ride along a portion of the threaded length of the lead shaft 42. In this manner, the rotation of the lead shaft 42 is transferred to an axial movement of the piston plunger 32, when the piston plunger is engaged with the lead shaft 42. The available length of travel of piston plunger 32 is dependant upon the length of the threaded portion of the lead shaft 42, the length of the piston plunger shaft 40 and the starting location of the engagement portion 38 of the piston plunger along the threaded length of the lead shaft 42.

The lead shaft 42 may be provided with threads along most or all of the length of the exposed portion of the shaft, to allow operable engagement of the threads on the engagement portion 38 to the corresponding threads on the lead shaft 42 at any location along the length of the exposed portion of the lead shaft 42. As described above, to further assist the operable engagement of the threads on the engagement portion 38 to the corresponding threads on the lead shaft 42, the engagement portion 38 may be provided with an arcuate surface on which the threads are arranged. The threaded arcuate surface of the engagement portion 38 may extend around one half or less (180 degrees or less) of the circumference of the lead shaft 42, when the engagement portion 38 is engaged with the lead shaft 42, i.e., when the durable housing portion and disposable housing portion are engaged as shown in FIG. 2. In further embodiments, the threaded arcuate surface of the engagement portion 38 may extend around a little more than one half (more than 180 degrees) of the circumference of the lead shaft 42 and may be composed of sufficiently resilient, flexible material to provide a snap-fit with the lead shaft, when the engagement portion 38 is engaged with the lead shaft 42, i.e., when the durable housing portion and disposable housing portion are engaged as shown in FIG. 2. Other types of drive engagement structures that may be used are shown in U.S. patent application Ser. No. 10/379,627 filed Mar. 5, 2003, and entitled "Leadscrew Driven Syringe With Integral Plunger Nut," and U.S. Pat. No. 5,954,697 issued Sep. 19, 1999, and entitled "Threaded Nut Syringe Plunger For Use With A Medication Infusion Pump," both of which are incorporated herein by reference in their entirety.

Figure 11A:
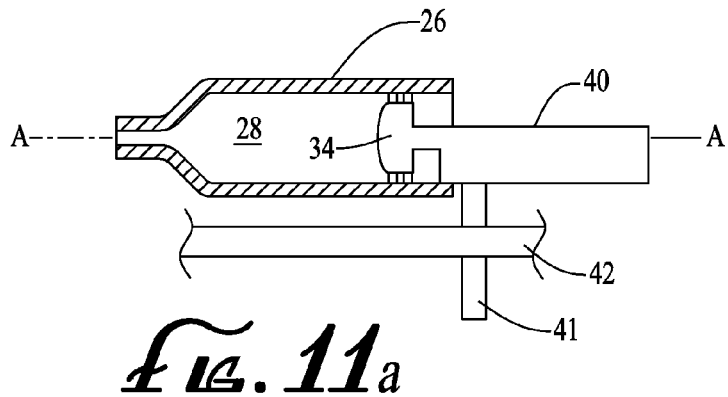
FIG. 11a is a schematic, cross-sectional view of a portion of a reservoir and a portion of a lead shaft according to another embodiment of the invention.
Figure 11B:
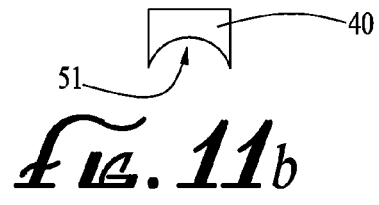
FIG. 11b is a further view of the piston shaft of FIG. 11, along the longitudinal axis of the piston shaft.

In other embodiments as represented in FIG. 11*a*, the piston plunger shaft 40 may be provided with teeth (or threads) along its length and the lead shaft 42 may have a disk-shaped threaded head portion 41 that may be relatively short in length in the axial direction A. The threaded head portion 41 has threads on its outer peripheral surface to engage the teeth (or threads) of the piston plunger shaft 40, for example, in a rack and pinion type of an arrangement, wherein the piston plunger shaft 40 may include a toothed rack and the threaded head portion 41 may function as a pinion gear. In embodiments as shown in FIG. 11*b*, the piston plunger shaft 40 may be provided with an arcuate surface 51 on which the teeth (or threads) are located. The arcuate surface 51 extends along the longitudinal dimension of the piston plunger shaft 40, outside of the interior portion of the reservoir and arcs partially around the axis of the lead shaft 42, to engage the head portion 41, when the durable housing portion and the disposable housing portion are engaged as shown in FIG. 2. The radius of the arcuate surface 51 may approximate the radius of the disk-shaped head 41, to allow the head 41 to readily, operatively engage the piston plunger shaft and to increase the surface area of engagement between those components, when the durable housing portion and disposable housing portion are engaged as shown in FIG. 2.

Similar to the arcuate surface of the engagement portion 38 in FIG. 4 described above, the arcuate surface 51 of the piston plunger shaft 40 in FIGS. 11*a* and 11*b* may extend around one half or less (180 degrees or less) of the circumference of the lead shaft 42, when the piston plunger shaft 40 is engaged with the lead shaft 42, i.e., when the durable housing portion and disposable housing portion are engaged as shown in FIG. 2. In further embodiments, the arcuate surface 51 of the piston plunger shaft 40 may extend around more than one half (more than 180 degrees) of the circumference of the lead shaft 42 and may be composed of sufficiently resilient, flexible material to provide a snap-fit with the lead shaft, when the piston plunger shaft 40 is engaged with the lead shaft 42, i.e., when the durable housing portion and disposable housing portion are engaged as shown in FIG. 2.

In the embodiments of FIGS. 4, 6, 7 and 11a and 11b, one of the lead shaft 42 or the piston plunger shaft 40 includes a threaded portion extending a length along the direction of axis A, beyond the length in the direction of axis A of the fluid containing portion 28 of the reservoir 26. The piston plunger shaft 40 may be provided with threads along most or all of the length of the exposed portion of the shaft, to allow operable engagement with the lead shaft 42 or threaded head portion 41, at any location along the length of the exposed portion of the piston plunger shaft 40.

A motor 44, lead shaft 42 and any linkage between the motor and lead shaft may be supported by the durable portion 22 of the delivery device in a location at which the threaded portion of the shaft 42 engages the threaded portion of the piston plunger 32, as shown in FIG. 4, 7, 8 or 11a. In this manner, when the durable portion 22 is arranged to be secured (such as by snap fitting, friction fitting or other suitable engagement configuration) onto the disposable portion 20, the threaded portion of the shaft 42 operatively engages the threaded portion of the piston plunger 32 without requiring further user manipulation of the elements. In other embodiments, additional manipulation of the housing portions and/or a manual operator may be required to operatively engage the threaded portion of the shaft 42 with the threaded portion of the piston plunger 32, while or after the durable portion 22 is arranged to be secured (such as by snap fitting, friction fitting or other suitable engagement configuration) onto the disposable portion 20.

While not shown in FIGS. 4 and 6, the motor 44 may be provided with electrical terminals for connection to a motor control circuit (e.g., motor control circuit 52 shown in FIG. 4 or a similar motor control circuit, not shown, in the durable housing portion 22 of FIG. 6. The motor control circuit 52 may be mounted within the durable portion 22 of the delivery device, for controlling the operation of the motor according to a desired infusion delivery program or profile. A delivery program or profile may be stored within a suitable electronic storage medium (not shown) located within the durable portion 22 and/or may be communicated to the delivery device 12 from other sources, such as a CCD 16 or a computer 18 (as shown in FIG. 1). In such embodiments, the delivery program or profile may be employed by the motor control circuit 52 to control the operation of the motor 44 in accordance with the delivery program or profile. Alternatively or in addition, the motor control circuit 52 may control the motor 44 to deliver one or more discrete volumes of infusion medium in response to delivery demand control signals generated within the device 12 or communicated to the device 12 from other sources, such as a CCD 16, sensor or monitor 14 or a computer 18 (as shown in FIG. 1).

The durable portion 22 may contain additional electronic circuitry (not shown) for communication with external devices such as the CCD 16 or computer 18, for storage of sensor data or other data, for processing and control functions, or for other functions. The durable portion 22 may have a user interface (not shown) including one or more buttons, electronic display (including, but not limited to, an LED display, an LCD display or other suitable electronic display), or the like, to allow a user to access data and/or input data or instructions to control electronic circuitry within the durable portion 22. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," both of which are incorporated herein by reference in their entirety.

In some embodiments, the durable portion 22 may contain a battery, high energy capacitor or other electronic power source (not shown) for providing electrical power to the motor 44, motor control circuit 52 and other electronic circuitry contained in the durable portion 22. In such embodiments, the battery, high energy capacitor or other electronic power source may be rechargeable through a recharge connector (not shown) provided on the durable portion 22. In other embodiments, a battery, capacitor or other electronic power source (not shown) may be supported on the disposable portion 20 and connectable to the motor 44, motor control circuit 52 and other electronic circuitry in the durable housing portion, through electrical connectors that make an electrical connection upon the durable portion 22 being coupled to the disposable portion 20, without additional manual manipulation. Such electrical connectors may include one or more pairs of conductive pads, where each pair of pads is connected to opposite poles of the power source and located on any suitable surface of the disposable portion 20 that engages a corresponding surface on the durable portion 22, when the durable portion 22 is coupled in engagement with the disposable portion 20. In such embodiments, the corresponding surface of the durable portion 22 includes one or more corresponding pairs of conductive pads that are electrically connected to the motor 44, motor control circuit 52 and other electronic circuitry in the durable housing portion and are arranged to engage the conductive pads on the disposable portion, when the durable portion 22 is engaged with the disposable portion 20. In other embodiments, further manual manipulation of the housings and/or a manual operator may be required to complete the electrical connection, once the durable portion 22 and the disposable portion 20 are engaged.

The durable portion 22 includes an interior volume 54 that contains the motor 44, gears 46-48, motor control circuit 52, other electronic circuitry and, in some embodiments described above, a power source. To protect those electrical and mechanical components from certain environmental conditions (such as, but not limited to, moisture, air, biological or medical fluids), the interior volume 54 of the durable portion 22 may be suitably sealed from the external environment by the housing structure 55 that forms the durable portion 22 and the seal(s) 45 for the opening through which the lead shaft 42 extends. Accordingly, the housing structure of the durable portion 22 and the seal(s) 45 may form a suitable moisture-tight seal, air-tight seal and/or hermetic seal, to protect the electronic components located in the interior volume 54 and/or separate those components from environmental, medical or biological materials to which the disposable portion 20 is exposed during normal operation. The gear train composed of gears 46, 47 and 48, may be included in the sealed interior volume 54, to protect and/or separate those mechanical components from environmental or biological materials, as well.

As discussed above, in the arrangement illustrated in FIGS. 2, 3, 4, 6, 7 and 11, the durable portion 22 may be attached (for example, snap fitted, friction fitted, or the like) onto the disposable portion 20, where the threaded portion of the lead shaft 42 automatically engages the threaded portion of the piston plunger 32 without requiring further user manipulation of the elements. In further embodiments, further user manipulation may be required for the lead shaft 42 to engage the threaded portion of the piston plunger 32. In the embodiment of FIGS. 4, 6 and 7, the threaded surface 39 of an engagement portion 38 of the piston plunger 32 may have an arcuate surface that curves around a portion of the longitudinal axis of the lead shaft 42. By providing the surface of the engagement portion 38 of the piston plunger 32 with an arcuate shape that curves around a portion of the longitudinal axis of the lead shaft 42, the surface area of the surface 39 that engages the lead shaft 42 may be increased. In addition, the curvature of the surface 39 of the engagement portion 38 around a portion of the longitudinal axis of the lead shaft 42 can help to inhibit inadvertent separation of the engagement portion 38 and the lead shaft 42, once the engagement portion 38 is engaged with the lead shaft 42. The curvature of the surface 39 also may allow the engagement portion 38 to easily align with and operably engage the lead shaft 42, by bringing the lead shaft 42 into contact with the engagement portion 38 as a consequence of the manual operation of coupling the durable portion 22 to the disposable portion 20.

Figure 12:
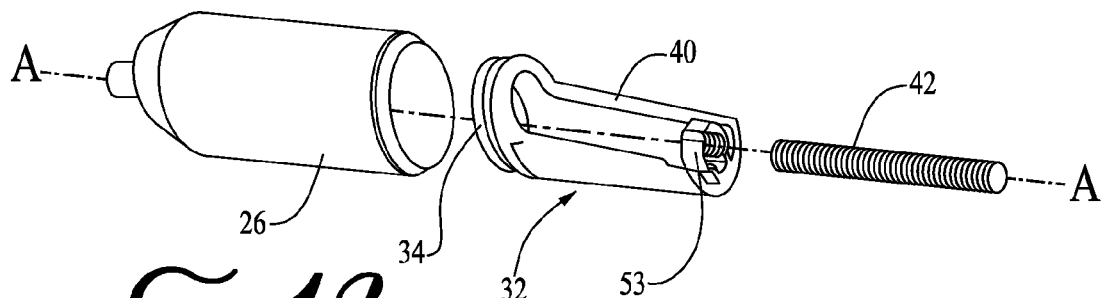
FIG. 12 is a perspective view of an embodiment of a reservoir, piston plunger and lead shaft suitable for the delivery device embodiments of FIGS. 4, 6 and 7.
Figures 13, 14:
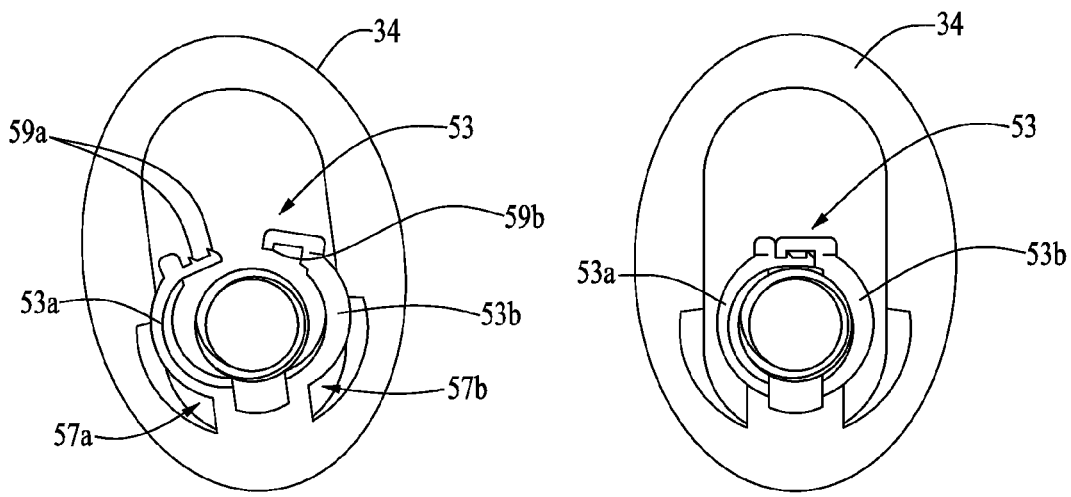
FIG. 13 is an axial view of the piston plunger of FIG. 12, with the clip open.
FIG. 14 is an axial view of the piston plunger of FIG. 12, with the clip closed.
Figure 15:
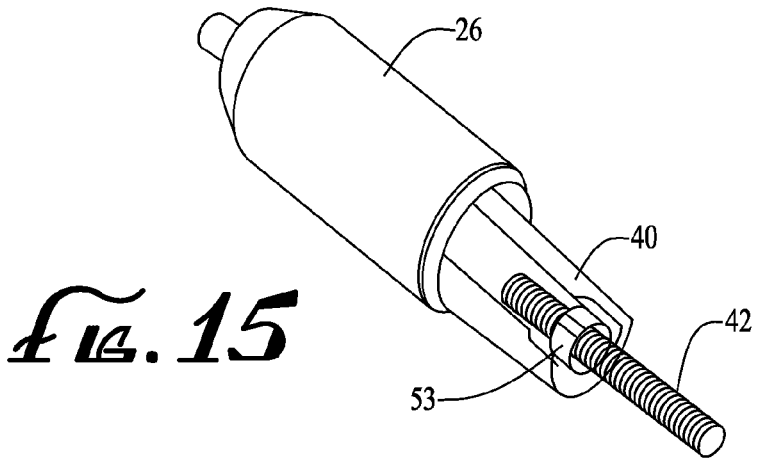
FIG. 15 is a perspective view of the piston plunger of FIG. 12 assembled with the reservoir of FIG. 12, and with the lead shaft of FIG. 12 in operable engagement with the piston plunger.

FIGS. 12-15 show a further example embodiment of a piston plunger 32 and lead shaft 42 configured for operable engagement, upon engagement of the disposable housing portion 20 and the durable housing portion 22. FIG. 12 is a perspective view of an embodiment of a reservoir, piston plunger and lead shaft suitable for the delivery device embodiment of FIG. 4. FIG. 13 is an axial view of the piston plunger of FIG. 12, with the clip open, while FIG. 14 is an axial view of the piston plunger of FIG. 12, with the clip closed. FIG. 15 is a perspective view of the piston plunger of FIG. 12 assembled with the reservoir of FIG. 12, and with the lead shaft of FIG. 12 in operable engagement with the piston plunger.

In the embodiment of FIGS. 12-15, the piston plunger 32 includes an oval-shaped piston head 34, having a shape and size for fitting within the correspondingly-shaped interior of the reservoir 26. The oval shape of the piston head 34 and the interior of the reservoir 26 inhibit rotation of the piston head 34 relative to the reservoir 26, when the piston head 34 is fitted within the interior of the reservoir 26.

The piston plunger 32 in the embodiment of FIGS. 12-15 includes a piston shaft 40 that has concave surface extending along the axial dimension A, that forms a trough shaped curvature, curving partially around the axis A. The trough-shaped curvature of the piston shaft 40 provides a receptacle for receiving the lead shaft 42, when the disposable housing portion 20 and the durable housing portion 22 are engaged. The piston shaft 40 includes at least one clip 53, for operatively engaging the lead shaft 42, when the disposable housing portion 20 and the durable housing portion 22 are engaged. While the embodiment of FIGS. 12-15 is shown with one clip 53, other embodiments may include two or more clips along the axial length A of the piston shaft 40.

The clip 53 includes a pair of clip arms 53a and 53b, each of which are flexible and/or pivotal between an open state (shown in FIG. 13) and a closed state (shown in FIG. 14). In the embodiment of FIGS. 12-15, the clip arms 53a and 53b each have a pivot point or flexible hinge portion 57a and 57b, respectively, to allow the arms 53a and 53b to pivot about an axis that is substantially parallel to the axis A, between the open and closed states. One or both of the clip arms includes threads that are of a suitable size and pitch to operatively engage with the threads on the lead shaft 42. When in an open state, each clip arm 53a and 53b has a free end that is spaced apart from the free end of the other clip arm. When in the closed state (FIG. 14), the free ends of the clip arms 53a and 53b engage and may partially overlap.

The free ends of the clip arms 53a and 53b may include locking structure for allowing the clip arms to lock together, when the free ends of the clip arms 53a and 53b are brought together, by flexing or pivoting the clip arms 53a and 53b about the pivot point or flexible hinge portion 57a and 57b, respectively. Such locking structure may include one or more protrusions 59a and 59b adjacent the free end of each clip arm 53a and 53b, respectively, where the protrusions 59a and 59b provide stop surfaces that abut each other when the free ends of the clip arms 53a and 53b are brought together, with one clip arm (e.g., clip arm 53b) partially overlapping the other clip arm (e.g., clip arm 53a).

In one embodiment, the clip arms 53a and 53b are biased (for example by a spring or a natural spring force of the material from which the clip arms are made) toward the closed position, but are held in an open position (as shown in FIG. 13) by a releasable lock mechanism. The lock mechanism may be released, for example, by the action of the lead shaft 42 engaging the flexible hinge portion 57a and 57b of one or both clip arms 53a and 53b. In other embodiments, the lock mechanism may be released by a manual operator (not shown), operable from outside of the disposable housing portion 20 and the durable housing portion 22, when those housing portions are engaged. In yet other embodiments, the clip arms 53a and 53b may be configured to be in an open position (as shown in FIG. 13) by the natural spring force of the material that forms the clip arms (or by a further bias member, such as a separate spring), and may be closed by the manual operation of engaging the disposable housing portion 20 with the durable housing portion 22, for example by squeezing the arms 53a and 53b together by sliding the arms in engagement with a diverging pair of walls or other structure in the durable housing portion 22 after the engagement portion 38 of the piston plunger 32 is manually aligned to engage with the lead shaft 42. In yet other embodiments, the clip arms 53a and 53b may be biased toward a closed position (by the natural spring force of the arms or by a separate bias member, such as a spring), while a stop member maintains the arms 53a and 53b in an open position (as shown in FIG. 13) prior to assembly of the disposable housing portion 20 with the durable housing portion 22. In such an embodiment, a stop release mechanism may be employed to release the arms 53a and 53b from the stop member and allow the arms 53a and 53b to close around the lead shaft 42, after the engagement portion 38 of the piston plunger 32 is manually aligned to engage with the lead shaft 42. In such an embodiment, the stop release mechanism may comprise an automatic structure that moves the stop member (or moves the arms 53a and 53b relative to the stop member) to automatically release the arms 53a and 53b by the manual action of engaging the disposable housing portion 20 with the durable housing portion 22. Alternatively, the stop release mechanism may comprise a further manual operator that requires a further manual operation (pushing a button, moving a lever or the like) to release the stop member and allow the arms 53a and 53b to move to their closed position.

In operation, as the durable housing portion 22 is manually brought into engagement with the disposable housing portion 20, the lead shaft 42 on the durable housing portion is aligned with the axial dimension A of the piston shaft 40 and is brought into a position between the open clip arms 53a and 53b. Either by automatic operation or by manual operation of the clip arms 53a and 53b, the clip arms 53a and 53b are flexed or pivoted from the open state to the closed state, to operatively engage the threads on the clip arms with the threads on the lead shaft 42, as shown in FIG. 15. Once engaged, rotation of the lead shaft 42 causes the piston plunger 32 to move in the axial dimension A, within the interior of the reservoir 26.

As described above, when the durable portion 22 and the disposable portion 20 are fitted together with the lead shaft 42 engaging the engagement portion 38 of the piston plunger 32, the motor 44 may be controlled to rotatably drive the lead shaft 42 and, thus, move the piston plunger 32 in the axial direction A of the reservoir 26. When the interior volume of the reservoir 26 is filled with an infusion medium and a hollow needle or cannula is positioned in a septum of the reservoir (for example, similar to septum 30 discussed above) to form a fluid flow path between the reservoir 26 and a patient-user, the piston plunger 32 may be controlled to move in the axial direction A, toward the septum 30 end of the reservoir 26, to force infusion medium from the reservoir volume 28, through the hollow needle or cannula and into the patient-user.

Once the reservoir 26 has been sufficiently emptied or otherwise requires replacement, the patient-user may simply unsnap and remove the durable portion 22 from the disposable portion 20 of the delivery device 12 and replace the disposable portion 20 (including the reservoir) with a new disposable portion having an unused new, user-filled, prefilled, refurbished, remanufactured or re-filled reservoir 26. The durable portion 22 may be engaged to the new disposable portion and the delivery device (including the new disposable portion) may be secured to (or otherwise carried by) the patient-user, as described above.

In further embodiments in which the reservoir 26 includes a reservoir canister that fits within a hollow interior of the reservoir retaining portion 24, the canister may be removed from the retaining portion 24 and replaced with an unused new, user-filled, prefilled, refurbished, remanufactured or re-filled canister, to allow the disposable portion 22 to remain in place on a patient-user for more than one reservoir depletion period. In such embodiments, the reservoir canister may be replaced one or more times during the operable life of the disposable portion 20 and the disposable portion 20 may be removed from the patient-user and replaced with a new or remanufactured disposable portion 20, for example, after a predefined number of reservoir canister replacement operations.

The drive motor 44 in FIG. 4 (or any of the embodiments described herein) may include any suitable rotary drive device that converts electrical power to mechanical, rotary motion. Examples of a suitable rotary drive motor 44 include, but are not limited to, a DC motor, flat or pancake DC motor, servo motor, stepper motor, electronically commutated motor, rotary piezo-electrically actuated motor, and the like. In further embodiments, the drive motor 44 may include a bender or linear actuator in combination with an escapement wheel arrangement, to rotatably drive the lead shaft 42. For example, a drive device for rotatably driving the lead shaft 42 may include a piezo-electrically actuated bender and escapement wheel arrangement, a thermally actuated bender and escapement wheel arrangement, a shape memory alloy wire and escapement wheel arrangement, an electronically actuated solenoid and escapement wheel arrangement, or the like. Examples of shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement Micro-Pump With Pulsatile Output," both of which are incorporated herein by reference in their entirety.

Figure 16A:
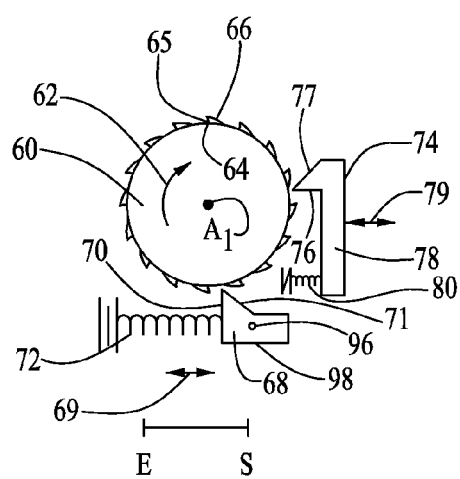
FIGS. 16a-d show schematic views of escapement wheel arrangements and components thereof, for providing a controlled rotational motion.

Escapement wheel arrangements operable with bender or linear actuators in accordance with example embodiments of the present invention are described with reference to FIGS. 16a-16c. As shown in FIG. 16a, an escapement wheel 60 is supported for rotation around an axis $A_1$ (extending into the page), in the direction of arrow 62. The escapement wheel 60 has an outer peripheral edge provided with serrations or teeth 64. Each tooth 64 includes a sloped surface 66 arranged at an obtuse angle relative to an axial direction of the wheel 60 and a catch surface 65 in a substantially axial direction of the wheel. A drive pawl 68 is located adjacent to the escapement wheel 60 and at least partially between two of the teeth on the escapement wheel. The drive pawl 68 is supported for movement in a generally linear direction, as represented by the double arrow 69, between a start position S and an end position E.

The drive pawl 68 has a drive surface 70 for engaging the catch surface 65 of an adjacent tooth 64 on the escapement wheel 60, when the drive pawl 68 is moved in a direction from the start position S to the end position E. The drive pawl 68 has a further surface 71 facing away from the drive surface 70 and configured for riding over the sloping surface 66 of a tooth 64 on the escapement wheel 60, when the drive pawl is moved in a return direction from the end position E to the start position S. The further surface 71 of the drive pawl 68 may be sloped at an angle relative to the radial direction of drive wheel, to assist the drive pawl 68 in riding over the sloping surface 66 of a tooth 64 of the escapement wheel.

As described in more detail below, the drive pawl 68 is coupled to a bender or linear motion actuator to selectively drive the drive pawl 68 from the start position S to the end position E. With each motion of the drive pawl 68 from the start position S to the end position E, the surface 70 engages the catch surface 65 of a tooth 64 on the escapement wheel and rotates the escapement wheel 60 a small distance. A bias member 72 is operably coupled to the drive pawl 68, to bias the drive pawl 68 in a return direction, to return the drive pawl 68 to the start position. The bias member 72 may include a spring as shown in FIG. 14a or other suitable mechanism for providing a bias force to return the drive pawl 68 to the start position, including, but not limited to a permanent magnet, electro-magnet, electronic or thermal linear actuator, shape memory alloy actuator, or the like. In the illustrated embodiment, the bias member 72 is a coil spring having one end coupled to the drive pawl 68 and another end coupled to a fixed surface, for example, a fixed surface of a wall or other fixed structure of or within the durable portion 22 of the drive mechanism 12 described above.

A further pawl 74 may be provided to inhibit back rotation of the escapement wheel 60 in the direction opposite to the direction of arrow 62. For example, the further pawl 74 may be located adjacent the escapement wheel 60 and at least partially between two of the teeth on the escapement wheel. The further pawl 74 has a surface 76 for engaging the catch surface 65 of an adjacent tooth 64 on the escapement wheel 60, to inhibit rotary motion of the escapement wheel 60 in the direction opposite to the direction of arrow 62.

The pawl 74 has a further surface 77 facing opposite to the surface 76, configured for riding over the sloping surface 66 of a tooth 64 on the escapement wheel 60, when the escapement wheel is driven in the rotary direction of arrow 62 by action of the drive pawl 68. The surface 77 of the pawl 74 may be angled relative to the radial direction of the drive wheel, to assist the pawl 74 in riding over the sloping surface 66 of a tooth 64 of the escapement wheel. The pawl 74 may be supported for pivotal motion about a pivot point 78 in the direction of double arrow 79, to allow the surface 77 of the pawl 74 to pivot in a direction away from the escapement wheel, to further assist the pawl 74 in riding over the sloping surface 66 of a tooth 64 of the escapement wheel.

A bias member 80 may be arranged to bias the surface 76 of the pawl 74 toward the escapement wheel, to return the pawl 74 to a position in which the surface 76 engages the catch surface 65 of a tooth 64, after the pawl 74 has ridden over the sloping surface 66 of an adjacent tooth 64 of the escapement wheel. The bias member 80 may include a spring as shown in FIG. 16a or other suitable mechanism for providing a bias force to return the pawl 74 to the position in which the pawl surface 76 engages the catch surface 65 of a tooth 64, including, but not limited to a permanent magnet, electro-magnet, electronic or thermal linear actuator, shape memory alloy actuator, or the like. In the illustrated embodiment, the bias member 80 includes a coil spring having one end coupled to the pawl 74 and another end coupled to a fixed surface, for example, a fixed surface of a wall or other fixed structure of or within the durable portion 22 of the drive mechanism 12 described above. In further embodiments, a leaf spring or other suitable spring structure may be employed, instead of a coil spring. For example, a spring may be located around or within the pivot point 78 of the pawl 74 for effecting the bias force described above.

As described above, the drive pawl 68 is coupled to a bender or linear motion actuator to selectively drive the drive pawl 68 and cause the escapement wheel to rotate a small distance with each motion of the drive pawl 68 from the start position S to the end position E. A bender or linear actuator may include a piezoelectric bender or piezoelectric actuator, a thermally actuated bender, a shape memory alloy wire, an electronically actuated solenoid, or the like. Such actuators for providing small, generally linear movements in response to the application of an electrical power signal are known. Examples of alternative shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement MicroPump With Pulsatile Output," both of which are incorporated herein by reference in their entirety.

Figure 16B:
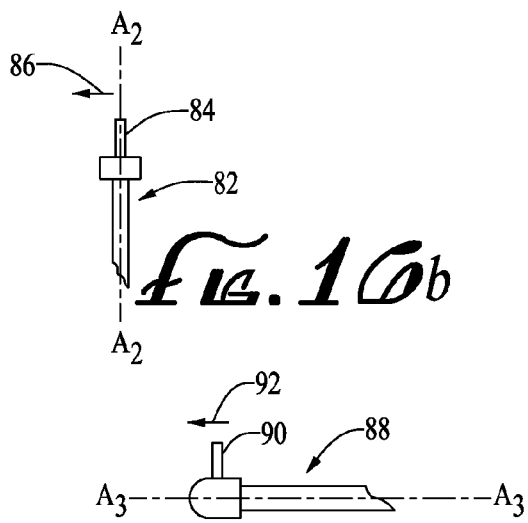
Figure 16C:
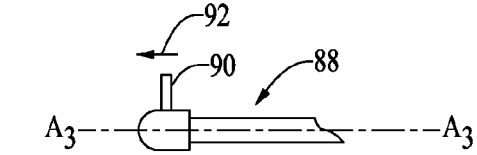

As shown in FIG. 16b, a bender actuator 82 may be configured to include a connector end 84 that is provided with a lateral motion represented by arrow 86 relative to a major axis $A_2$ of the actuator body, when a power signal is applied to the actuator. Alternatively, as shown in FIG. 14c, a linear actuator 88 may be configured to include a connector end 90 that is provided with a longitudinal motion represented by arrow 92 relative to a major axis $A_3$ of the actuator body, when a power signal is applied to the actuator. A bender actuator as shown in FIG. 16b, for providing lateral motion, may be coupled to the drive pawl 68 at a connection location 96. The connection location 96 for a bender actuator may be on a surface of the drive pawl 68 that is substantially perpendicular to the drive surface 70. Alternatively, a linear actuator as shown in FIG. 16c, for providing longitudinal motion, may be coupled to the drive pawl 68 at a connection location 98. The connection location 98 for a linear actuator may be on a surface of the drive pawl 68 that is substantially parallel to the drive surface 70. In that manner, a bender or a linear actuator as shown in FIGS. 16b and 16c may be employed to selectively move the drive pawl 68 from the start position S to the end position E and, thus drive the escapement wheel 60 in a rotary manner. In yet further embodiments, the drive pawl 68 may be eliminated and the bender or linear actuator may be arranged to directly engage the catch surfaces of the teeth on the escapement wheel 60.

The escapement wheel 60 may be configured to rotate the rotary distance of one tooth for each movement of the drive pawl 68 from the start position S to the end position E. In further embodiments, the drive pawl 68 may be configured to cause the escapement wheel 60 to rotate a rotary distance of a pre-defined number of teeth greater than one tooth, for each movement of the drive pawl 68 from the start position S to the end position E. The escapement wheel 60 may be coupled to the lead shaft 42, to rotate the lead shaft 42 with rotation of the escapement wheel 60. In one embodiment, the lead shaft 42 may be connected in axial alignment directly to the escapement wheel 60, such that the rotary axis $A_1$ of the escapement wheel is in alignment with the longitudinal axis of the lead shaft 42. In other embodiments, the escapement wheel 60 may be coupled, in axial alignment, with any one of the drive gear 46, engagement gear 47 or linking gear 48 shown in FIG. 4 or FIG. 8, to transfer rotary motion of the escapement wheel 60 to the lead shaft 42. In yet further embodiments, other suitable gear and linkage arrangements may be employed for transferring rotary motion of the escapement wheel 60 to the lead shaft 42.

The use of bender or linear actuators with escapement wheel arrangements as described above may provide certain advantages over electric motor and linkage arrangements, in that the bender or linear actuators can provide a repeatable, controlled, step-like response to an electrical power signal. In the context of driving a delivery device for delivering a medication to a patient-user, the ability to accurately control the drive response can provide significant advantages, for example, in administering accurate quantities, small quantities at accurate levels and accurate recording of delivered quantities of the medication. In addition, bender or linear actuators with escapement wheel arrangements can be made relatively small and flat and can, therefore, improve the ability to form the delivery device 12 with a relatively small and flat shape. In addition, bender or linear actuators with escapement wheel arrangements can operate with relatively low power requirements, thus prolonging the operational life of the power source and allowing smaller power sources to be employed, thus, allowing further reductions in the size of the delivery device.

Figure 16D:
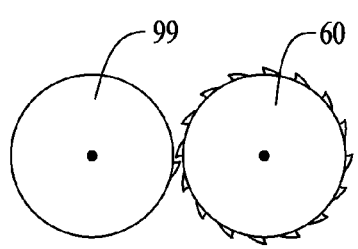

Other types of drive devices may be coupled to an escapement wheel 60, as shown in FIG. 16d, to provide a controlled, step-like response. For example, in the embodiment shown in FIG. 16d, a second wheel 99 has one tooth and is coupled to the lead shaft 42 as described above, while the toothed escapement wheel 60 is operatively coupled to the lead shaft 42, for example, through a suitable linkage structure as described herein. The second wheel 99 may be driven by any suitable rotary drive source, including, but not limited to a DC motor, flat or pancake DC motor, servo motor, stepper motor, electronically commutated motor, rotary piezo-electrically actuated motor, and the like. While the second wheel 99 in FIG. 16d is provided with a single tooth to effect a rotation of the escapement wheel 60 a rotary distance of a single tooth for each complete rotation of the second wheel 99, other embodiments may employ a second wheel 99 having two teeth (or another pre-defined number of teeth) for effecting a rotation of the escapement wheel 60 a rotary distance of two teeth (or the pre-defined number of teeth) for each complete rotation of the second wheel 99.

The above embodiments involve various manners of conveying a drive force to the lead shaft 42, to rotate the lead shaft 42 and drive a piston plunger 32 within the reservoir 26. Further embodiments may employ other mechanisms for driving a plunger within a reservoir, to selectively deliver infusion medium from the reservoir.

For example, FIGS. 17-21 show a further embodiment of a delivery device, which includes a disposable portion 120 and a durable portion 122. The disposable portion has a reservoir retaining portion 124 in which a reservoir 126 is located. The disposable portion 120, durable portion 122, reservoir retaining portion 124 and reservoir 126 may be similar to the disposable portion 20, durable portion 22, reservoir retaining portion 24 and reservoir 26 described above with respect to FIGS. 2-6. However, the reservoir 126 in FIGS. 17-21 employs a rotatable plunger shaft 127 located within the reservoir interior 128, instead of the arrangement shown in FIGS. 2-8 that employs a piston plunger shaft 40 that extends, lengthwise, a distance beyond the medium-containing portion of the interior 28 of the reservoir 26 by a distance at least as great as the distance that the piston head 34 moves over the full period of use of the reservoir. Accordingly, the overall length of the reservoir and internal shaft of FIGS. 17-21 may be smaller relative to the overall length of the reservoir and external shaft of FIGS. 2-8, for a given reservoir volume.

Figure 18:
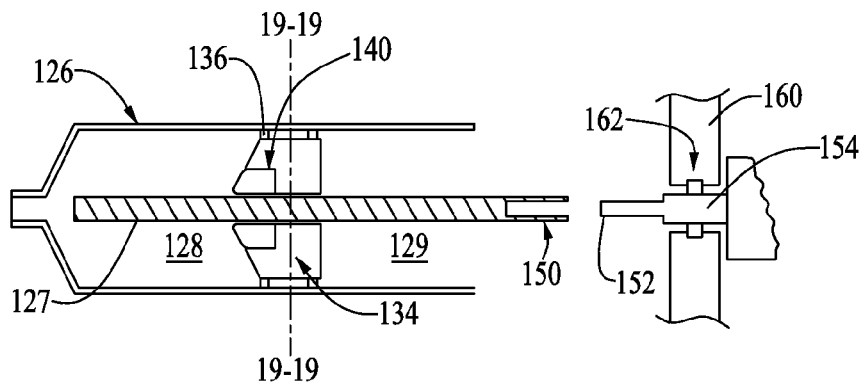
FIG. 18 shows a schematic, cross-sectional view of a reservoir and moveable plunger head of the delivery device of FIG. 17.
Figure 19:
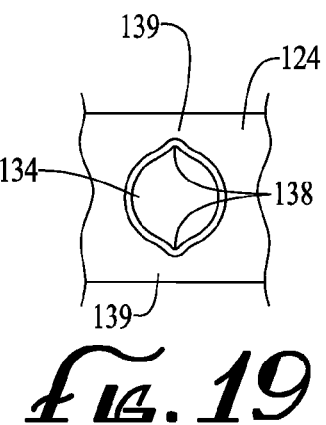
FIG. 19 shows a cross-sectional view taken along line 10-10 of FIG. 18.
Figure 17:
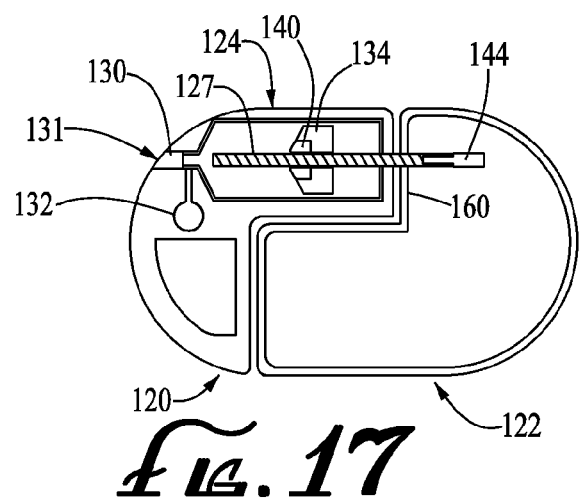
FIG. 17 shows a schematic view of a delivery device according to a further embodiment of the present invention.

The reservoir 126 in FIGS. 17 and 18 may include a septum 130, similar to the septum 30 described above with respect to FIG. 5. The septum 130 may include a surface 131 that is exposed through a wall of the reservoir retaining portion 124, for filling the reservoir 126 or withdrawing infusion medium from the reservoir 26, for example, by piercing the exposed surface of the septum with a syringe.

An injection site 132 may be located within the disposable portion 120, adjacent the reservoir 126 and connected in fluid flow communication to the interior of the reservoir 126. The injection site 132 may employ a mechanism for inserting a hollow needle or cannula into a patient-user, after the disposable portion 120 is secured to the patient-user and coupling the needle or cannula in fluid flow communication to the interior of the reservoir 126. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

The rotatable shaft 127 is threaded along its length within the interior of the reservoir 126. A moveable plunger head 134 is located within the interior of the reservoir 126 and is threaded and engaged with the rotatable shaft 127. In particular, the plunger head 134 has a threaded channel that has threads of a pitch and diameter to engage and mate with the threads of the rotatable shaft 127. By rotating the shaft 127 without rotating the plunger head 134, the plunger head is moved along the length of the shaft 127, within the interior of the reservoir 126. In this manner, the shaft 127 may be rotated to drive the plunger head 134 and force the infusion medium from the reservoir 126 to a patient-user, through a hollow needle or cannula connected in fluid flow communication with the reservoir. While the threaded channel in the plunger head 134 may be located at the center of the diameter of the plunger head 134, other embodiments may employ a plunger head 134 with an off-center channel (a channel that is laterally spaced relative to the longitudinal axis A of the reservoir). An off-center location of the channel in the plunger head 134 allows the transfer of linear motion (with the rotational motion of the lead shaft 127) to the plunger head 134, while inhibiting rotation of the plunger head 134 relative to the lead shaft 127.

One or more seals 136 may be provided around the outer peripheral surface of the plunger head 134, to inhibit the passage of infusion medium across the plunger head 134, from the medium-retaining interior portion 128 of the reservoir to the external side 129 of the plunger head 134. One or more annular grooves may be provided in the outer peripheral surface of the plunger head 134 for retaining the seal(s) 136. The seal(s) 136 may include one or more o-ring seals or other suitable seal structure and may be made of any suitable seal material, including, but not limited to, rubber, silicone rubber, polyurethane or other plastic material, metal, composite material or the like. The seal(s) 136 may provide sufficient frictional force between the plunger head 134 and the interior surface of the reservoir 126 to inhibit rotation of the plunger head 134 with the rotation of the shaft 127. However, in further embodiments, additional structure may be provided to inhibit rotation of the plunger head with the rotation of the shaft 127, including, but not limited to, one or more projections or shaped portions 138 on the plunger head 134 that fit within corresponding one or more shaped grooves along the length of the interior wall of the reservoir 126, as shown in the cross-section view of FIG. 19 (taken along the cross-section 19-19 of FIG. 18). The shaped projection(s) 138 may have generally curved configurations, with slow curvatures (as compared to an abrupt step), to allow one or more seals 136 to be placed around the plunger head. In alternative embodiments, the interior wall of the reservoir 126 may include a projecting portion extending along the length of the reservoir, for engaging a corresponding groove in the plunger head 134, similar to, but reverse of the projection and groove arrangement shown in FIG. 19. In yet further alternative embodiments, the cross-sectional shape of the plunger head 134 and the reservoir 126 (in the cross-sectional direction shown in FIG. 19) may be non-circular, to inhibit rotation of the plunger head 134 with rotation of the shaft 127. Such non-circular cross-section shapes may include, but are not limited to, an oval or partially oval shape, a polygonal or partially polygonal shape, or the like.

Figure 20:
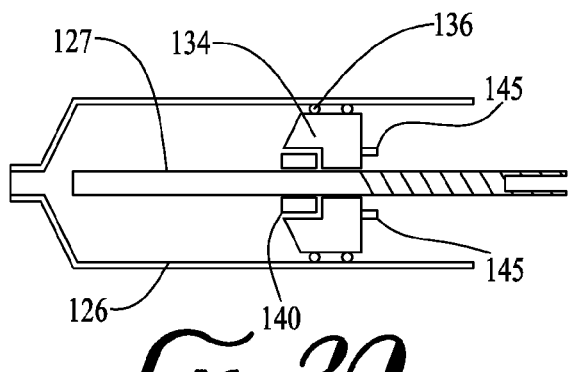

The plunger head 134 includes one or more seals 140 arranged to provide a fluid-tight seal between the plunger head 134 and the lead shaft 127, to inhibit the passage of infusion medium through the central channel of the plunger head 134, from the infusion medium-retaining interior portion 128 of the reservoir to the external side 129 of the plunger head 134, as the plunger head 134 is moved toward the septum end of the reservoir 126. The seal(s) 140 may include an annular structure disposed on one side (such as the infusion-medium-contacting side) of the plunger head 134 and made of any suitable seal material, including, but not limited to, rubber, silicone rubber, polyurethane or other plastic material, metal, composite material or the like. Alternatively, or in addition, the seal(s) 140 may be located within the central channel of the plunger head 134, between the plunger head 134 and the lead shaft 127. In the embodiment of FIG. 20, the lead shaft 127 is, at least initially, not threaded, while the plunger head 134 is provided with one or more cutting blades 145, to cut threads into the lead shaft 127 and ride along the cut threads, as the lead shaft is rotated. In the embodiment of FIG. 20, the lead shaft 127 may be made with a smooth surface and of any suitable material that would allow the thread forming blade(s) 145 to cut threads into the lead shaft 127 when the lead shaft 127 is rotated by the drive linkage 154. Rotation of the lead shaft 127 would cause the thread forming blades to cut threads into the lead shaft 127 and would cause the plunger 134 to move toward the infusion medium-retaining interior portion 128 of the reservoir 126.

Figure 21:
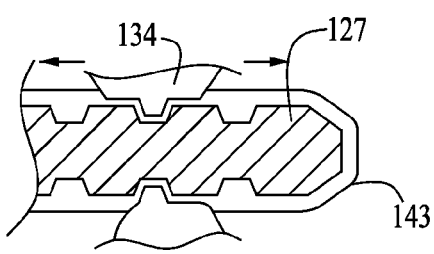
FIGS. 20 and 21 show schematic views of embodiments of seal arrangements for the plunger head within the reservoir of FIGS. 17 and 18.

Alternatively, or in addition, the lead shaft 127 may be coated or wrapped with one or more layers 143 of a seal material, as shown in FIG. 21. The seal material layer 143 may include, but is not limited to, rubber, silicone rubber, polyurethane or other plastic material, or other material having suitable elasticity and flexibility to allow the threads of the plunger head 134 to operatively engage the coated or wrapped threads of the lead shaft 127. In yet further embodiments, the inner surface of the central channel in the plunger head may be provided with seals 140 or sealing material 143, in addition to or as an alternative to seals or sealing material on the shaft 127.

The shaft 127 has a connection end 150, for connection to a mating connection end 152 of a drive linkage 154. The drive linkage 154 may be a direct connection to the drive shaft of a motor 144, such that the connection end 152 of the drive linkage 154 rotates with the rotary drive motion of the drive shaft of the motor 144. In other embodiments, the drive linkage 154 may include one or more gears, belts, chains, drive shafts or other linkage structure (not shown) for transferring drive force from a motor 144 to rotational motion of the connection end 152 of the drive linkage. The motor 144 may be any suitable drive device for rotatably driving the connection end 152 of the drive linkage (either directly or through one or more gears, belts, chains, drive shafts or other linkage structure), including, but not limited to the example drive devices described above with respect to the motor 44 in FIG. 4 and escapement wheel arrangements in FIGS. 16a-16d.

The motor 144 and any gears, belts, chains, drive shafts or other linkage structure for coupling the motor 144 to the drive linkage 154 may be contained within the interior of the housing structure of the durable portion 122. The drive linkage or the drive shaft of the motor 144 may extend through an aperture in a wall 160 of the housing structure of the durable portion 122. A seal 162 may be provided within or adjacent the aperture in the wall 160, to inhibit the passage of one or more of moisture, air, biological materials or infusion media into the interior of the housing structure of the durable portion 122. The seal 162 may include, but is not limited to, one or more o-ring seals disposed around the aperture in the wall 160 or around the portion of the drive linkage or drive shaft that extends through the aperture in the wall 160. The seal 162 may be made of any suitable sealing material, including, but not limited to rubber, silicone rubber, polyurethane or other plastic material, metal, composite material or the like.

The connection end 152 of the drive linkage 154 and the connection end 150 of the lead shaft 127 are configured to connect to each other when the durable portion 122 is coupled to the disposable portion 120 and to disconnect from each other when the durable portion 122 is separated from the disposable portion 120. For example, the connection ends 150 and 152 of the lead shaft 127 and the drive linkage 154, respectively, may include mating features that are configured to easily engage with each other when the connection ends 150 and 152 are brought together and disengage from each other when the connection ends 150 and 152 are moved apart. In addition, the mating features allow the transfer of rotational motion from the drive linkage 154 to the lead shaft 127, when the connection ends 150 and 152 are engaged.

In one example embodiment as shown in FIG. 22, the mating features may include a slot 164 formed on the connection end 150 of the lead shaft 127 and a tab 166 extending from the connection end 152 of the drive linkage 154, where the tab 166 is shaped to fit within the slot 164 to connect the lead shaft 127 in rotational communication with the drive linkage 154. Alternatively, the slot 164 may be formed on the connection end 152 of the drive linkage 154 and the tab 166 may extend from the connection end 150 of the lead shaft 127. The shape of the tab 166 and the slot 164 in FIG. 20 have a generally rectangular cross-sectional dimension (in the cross-section plane perpendicular to the longitudinal dimension of the lead shaft 127). Other embodiments may employ a tab and slot arrangement with other non-circular cross-sectional shapes (in the cross-section plane perpendicular to the longitudinal dimension of the lead shaft 127) to allow communication of rotational motion from the drive linkage 154 to the lead shaft 127. In further alternative embodiments, the mating features may be other shapes that can be readily engaged together to communicate rotational motion from the drive linkage to the lead shaft 127 and readily separated to allow the durable portion 122 to be removed from the disposable portion 120 of the delivery device. Such other shapes include, but are not limited to, mating star-shaped structures, cross-shaped structures, non-circular mating shapes (e.g., oval, partially oval, polygonal or partially polygonal), a mating pattern of projections and recesses, or the like, on the connection ends 150 and 152.

In the delivery device embodiments described above, a plunger head 34 or 134 is driven within a reservoir 26 or 126 to drive the infusion medium from the reservoir. Further embodiments of mechanisms for driving a plunger head within a reservoir of a delivery device are described with reference to FIGS. 23-27.

In the embodiment of FIG. 23, a reservoir 226 employs a moveable plunger head 234. The reservoir 226 and the plunger head 234 may be similar to the reservoir 126 and plunger head 134 described above with respect to FIG. 18, except that the plunger head 234 need not include a threaded central channel. The plunger head 234 includes seals 236 similar to the seals 136 on the plunger head 134 described above with respect to FIG. 18. The plunger head 234 and reservoir 226 may include further structure to inhibit rotation of the plunger head within the reservoir 226, for example, as described above with respect to example structure for inhibiting rotation of the plunger head 134, including, but not limited to, structure described above with respect to FIG. 19. The reservoir 226 may include a septum 230, similar to the septa 30 and 130 described above. The septum 230 may be used for refilling the reservoir 226 and/or for receiving a hollow needle or cannula to provide a fluid flow path to a patient-user, as described above with respect to the septa 30 and 130.

A slide tube 240 is configured to engage the plunger head 234. The slide tube 240 includes a generally hollow, cylindrical tube made of a suitably rigid material, such as, but not limited to, metal, plastic, ceramic, composite material or the like. One end of the cylindrical slide tube 240 is provided with a mating feature 242 for mating with a corresponding mating feature 244 on the plunger head 234. In the embodiment of FIG. 23, the mating feature 242 includes a projection that extends from the end of the slide tube 240 in the axial direction of the cylindrical shape of the slide tube, while the mating feature 244 includes a recess in the exterior-facing side of the plunger head 234. The recess 244 has a shape adapted to receive the projection 242, when the end of the slide tube 240 is brought into engagement with the exterior-facing side of the plunger head 234. The recess 244 and projection 242 may have corresponding, mating shapes having non-circular cross-sectional dimensions (in the cross-section plane perpendicular to the axis $A_S$) that inhibit relative rotation between the slide tube 240 and the plunger head 234. In another embodiment (as shown in FIG. 24), the plunger head 234 may be connected to (or unitary with) a sleeve 240 that has a hollow interior. The sleeve 240 in FIG. 24 may have a slot-like opening along its longitudinal dimension through which a rotary drive screw 248 may be received. The slot-like opening in the sleeve 240 may be smaller than the diameter of the rotary drive screw 248 and the sleeve 240 may be made of a suitably elastically flexible material to allow the dive screw 248 to be snap fit into the hollow interior of the sleeve 240, through the slot-like opening in the sleeve 240.

The slide tube 240 (in either of the embodiments of FIGS. 23 and 24) has a generally hollow interior and an interior surface 246 that is threaded along at least a portion of its length. The rotary drive screw 248 includes a shaft that extends coaxially with the slide tube 240. The drive screw 248 shaft extends through one end (opposite to the end connected to the plunger head) of the slide tube 240. One end of the drive screw 248 shaft extends into the interior of the slide tube 240 and an opposite end of the drive screw 248 shaft extends outside of the slide tube 240. The drive screw 248 may be threaded along its length (as shown in FIG. 24) or may have a threaded head 249 coupled to the drive screw shaft (as shown in FIG. 23). The threads along the length of the drive screw 248 or the threaded head 249 has threads of a pitch and diameter for engaging and mating with the threads on the threaded interior surface 246 of the slide tube 240. In that arrangement, rotation of the drive screw 248 results in a linear movement of the slide tube 240 along the direction of the axis $A_5$ of the slide tube 240. By rotating the drive screw with a rotary drive device in the appropriate direction, the slide tube pushes the plunger head 234 toward the septum end of the reservoir 226, to force infusion medium through a hollow needle or cannula, to a patient-user.

The end of the drive screw 248 shaft that is external to the slide tube 240 is coupled to a drive device, through suitable drive linkage, to rotate the drive screw 248 in a controlled manner. In the embodiment shown in FIG. 23, the drive device includes a linear actuator 250, such as a piezoelectric actuator device that expands in a linear direction, upon the application of a suitable electrical drive signal. The actuator 250 is arranged to frictionally engage and rotate a rotary wheel 252 a small amount in the direction of arrow 256 with each linear expansion of the actuator 250. The actuator 250 may be selectively controlled to drive the rotary wheel 252 in the direction of arrow 256 for dispensing infusion medium from the reservoir 226, and in the direction opposite to the direction of arrow 256, to retract the plunger head 234 and allow replacement of the reservoir 226. A spring 254 or other suitable structure may be provided to force the actuator 250 against the rotary wheel 252 during expansion of the actuator. The rotational motion of the rotary wheel 252 is transferred to rotational motion of the drive screw 248, through suitable transfer gearing 258. According to the arrangement shown in FIG. 21, the linear actuator 250 may be selectively energized to rotate the wheel 252, which rotates the drive screw 248, which causes the slide tube 240 to move axially and push the plunger head 234 toward the septum end of the reservoir 226, in a controlled, step-like manner.

While FIG. 23 shows a linear drive device that includes a linear actuator for rotatably driving the drive screw 248, other embodiments may employ other drive devices operatively coupled to drive the drive screw 248. For example, FIG. 24 shows an embodiment in which the drive device includes a DC pancake motor 260 that is operatively coupled to the external end of the drive screw 248, through any suitable interface gear arrangement 262. In further embodiments, the drive screw 248 may be operatively coupled to any suitable drive device for rotatably driving the drive screw 248 in a controlled manner, including, but not limited to the example drive devices described above with respect to the motor 44 in FIG. 4 and escapement wheel arrangements in FIGS. 16a-16d.

As shown in FIG. 23, the slide tube 240 may be supported within a portion of a housing structure 266, such as the housing structure of a durable portion of a delivery device. The slide tube 240 extends through an opening in the housing structure 266 to engage the plunger head 234. One or more seals 268 may be disposed around the opening in the housing structure 266 and/or the slide tube 240, to protect the drive device from, for example, moisture, air, biological material or infusion media. The seal(s) 268 may be o-ring seals or other suitable seals made of any suitable seal material, including, but not limited to, the seal materials described above with respect to the seal(s) 45. In addition, an anti-rotation structure may be provided, to inhibit rotation of the slide tube 240 about the axis $A_5$, relative to the housing structure 266. In one embodiment, the anti-rotation structure may include a projection 241 extending from the slide tube 240, for engaging a stop surface 243 that is fixed relative to the housing structure 266. In other embodiments, the seal(s) 268 may provide sufficient frictional engagement with the slide tube and/or the housing structure 266, to inhibit rotation of the slide tube 240 about the axis $A_5$, relative to the housing structure 266.

The reservoir 226 may be located within a disposable housing portion, while the slide tube 240, drive screw 248 and drive device 250 or 260 may be located within a durable housing portion that can selectively couple to or separate from the disposable housing portion, as described above with respect to embodiments of FIGS. 1-22. In a further embodiment, as shown in FIG. 25, a delivery device includes a disposable housing portion 320 having a reservoir retaining portion 324 for containing multiple reservoirs 326 (two in FIG. 25). A piston plunger head 334 is located in each reservoir 326 and may be operated by a slide tube arrangement similar to that shown in either of FIG. 23 or 24 or other suitable piston moving structure. The delivery device in FIG. 25 includes a durable housing portion 322 for containing one or more drive devices 344 and linkage 362 (which may include, for example bevel gears pinion gears or other suitable gear arrangements) for coupling the drive device(s) to the reservoirs 326. For example, a drive device, slide tube and drive screw arrangement as described with respect to FIGS. 23 and 24 may be included in the durable housing portion 322.

The embodiment of FIG. 26 employs a reservoir 326, plunger head 334, seals 336 and seals 368, similar to the reservoir 226, plunger head 234, seals 236 and seals 268 described above with respect to FIG. 23. The embodiment of FIG. 26 also includes a slide tube 340, similar to the slide tub 240 of FIG. 23, except that the slide tube 340 need not include a threaded interior surface. Instead, the slide tube 340 in FIG. 26 is operatively coupled to a drive device 344 in the form of a linear motor comprising one or more (two in FIG. 26) piezoelectric stacks 346 compressed on a drive shaft 348. The drive shaft 348 may be fixed to a durable portion 366 of delivery device, similar to the durable portion 266 described above.

The linear motor drive device 344 may be selectively energized by selectively applying electrical control signals to the piezoelectric stacks to cause the slide tube 340 to move toward the septum end of the reservoir 326, to selectively force infusion medium out of the reservoir, as described above with respect to the reservoir 226 in FIG. 23. However, the linear motor drive device 344 of FIG. 26 may be considerably smaller and may consume less power than some of the drive devices and linkages described above for creating rotary motion to drive the slide tube 240 of FIG. 23.

A further embodiment of a delivery device shown in FIG. 27 includes a reservoir 426 and a moveable plunger head 434 within the interior of the reservoir 426. The reservoir 426 and plunger head 434 may be similar to the reservoir 326 and plunger head 334 of FIG. 26, except that the plunger head 434 need not have a mating feature for engaging a slide tube. Instead, the plunger head 434 is configured to abut an expandable bellows 436 and move along the direction of the longitudinal axis $A_6$ of the reservoir 426 with the expansion of the bellows 436.

The bellows 436 is any suitable expandable structure that includes an interior volume that is expandable and that is capable of containing a hydraulic fluid. The delivery device in FIG. 27 includes a second reservoir 438 for containing hydraulic fluid, a conduit or tube 440 connected to the hydraulic fluid reservoir 438 and the bellows 436, for providing a fluid-flow communication path between the hydraulic fluid reservoir 438 and the interior volume of the bellows 436. A pumping mechanism 444 is provided to selectively pump hydraulic fluid into the bellows 436.

In the embodiment shown in FIG. 27, the pumping mechanism 444 is a peristaltic pump device including a rotor 446 mounted for rotation about an axis R. The rotor 446 has a plurality of rollers or pads arranged to engage a portion of the conduit 440 and roll or slide along a length of the conduit 440. The conduit 440 may be elastically flexible, at least along the length engaged by the rotor 446 rollers or pads. The length of the conduit 440 engaged by the rotor 446 may be arranged along an arcuate surface 448, where the arc of the surface 448 corresponds to the diameter of the rotor 446. The arcuate surface 448 may be a surface of a wall or other structure formed within the durable housing portion 422.

By rolling across the conduit 440 on the arcuate surface 448, the rotor rollers or pads may engage and squeeze the conduit 440 during the period of motion of the rollers or pads along the length of the arcuate surface 448. The rolling or sliding motion of the rotor rollers or pads along the arcuate length of the flexible conduit 440 creates a sufficient pressure differential to drive hydraulic fluid from the hydraulic fluid reservoir 438 to the interior of the bellows 436, in a manner controlled by the controllable rotary motion of the rotor 444. Any suitable rotary drive device or arrangement, such as, but not limited to those described herein, may be employed to drive the rotor 444 in a controlled manner.

As hydraulic fluid is pumped into the bellows 436 by the pumping mechanism 442, the hydraulic fluid creates a fluid pressure within the bellows sufficient to cause the bellows to expand an amount dependent upon the amount of hydraulic fluid pumped into the bellows. As the bellows 436 expands, the end of the bellows that abuts the plunger head 434 is moved toward the septum end of the reservoir 426 and pushes the plunger head 434 toward the septum end of the reservoir 426. As the plunger head 434 is moved toward the septum end of the reservoir 426, the plunger head forces infusion medium within the reservoir 426 out through a suitable hollow needle or cannula, to a patient-user.

While the embodiment of FIG. 27 employs a peristaltic pump device 444 to drive hydraulic fluid from the hydraulic fluid reservoir 438 to the bellows 436 in a controlled manner, other embodiments may employ other suitable pump devices for performing that function, including, but not limited to, conventional piston pumps, impeller pumps, membrane pumps, or the like.

In the embodiment shown in FIG. 27 the reservoir 426 may be located in a disposable portion 420 of the delivery device, while the hydraulic fluid reservoir 438, hydraulic fluid pump device 444, pump drive motor (not shown) and bellows 436 may be located in a durable portion 422 of the delivery device. The disposable portion 420 and durable portion 422 may be configured to be coupled together for operation, or separated for servicing, as described above with respect to disposable portion 20 and durable portion 22 in FIGS. 2 and 3. The disposable portion 420 may be provided with a needle insertion mechanism, for inserting a hollow needle or cannula into a patient-user's skin and connecting the hollow needle or cannula in fluid flow communication with the interior of the reservoir 426, when the disposable portion 420 is secured to a patient-user's skin, as described above with respect to the disposable portion 20 of FIGS. 2 and 3. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application No. 60/839, 840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, (047711-0384). Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Figure 28:
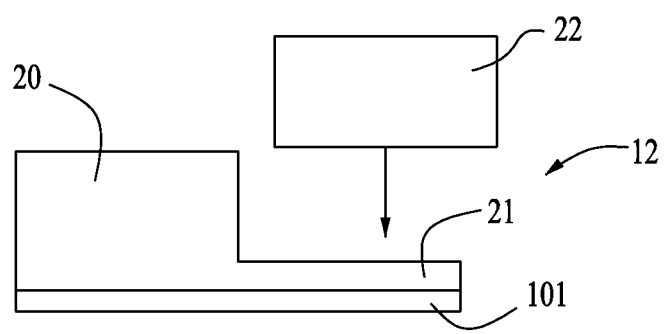
FIG. 28 shows a schematic side view of an arrangement of a durable housing portion and a disposable housing portion of a delivery system according to an embodiment of the invention consistent with the embodiment of FIG. 3.

In embodiments described above, the disposable housing portion (e.g., 20 in FIG. 3) is provided with a base portion 21 that may be secured to the patient-user's skin by, for example, but not limited to, an adhesive material provided on the bottom surface of the base portion 21. That arrangement is generally represented, in side view, in FIG. 26, wherein an adhesive material 101 is provided on the bottom surface (skin-facing surface) of the base 21 of the disposable housing portion 20. As shown in FIGS. 2, 3 and 28, the durable housing portion 22 may be configured to be arranged on the base 21 of the disposable housing portion 20 to engage and connect to the disposable housing portion 22. In such an arrangement, the base 21 may be disposed between the durable housing portion 22 and the patient-user's skin, during operation, such that only the base 21 of the disposable housing portion remains in contact with the patient-user's skin, during operation.

Figure 29:
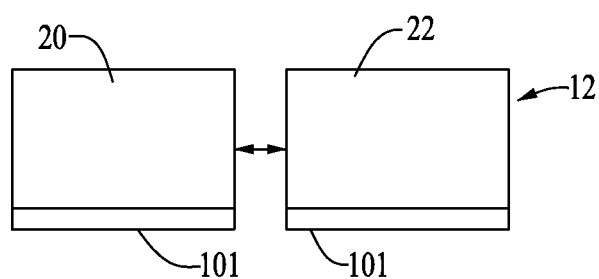
FIG. 29 shows a schematic side view of an arrangement of a durable housing portion and a disposable housing portion of a delivery system according to another embodiment of the invention.

However, in other embodiments, the durable housing portion 22 and the disposable housing portion 20 may be configured to engage each other in a side-by-side arrangement, for example, as represented in FIG. 29. In the side-by-side arrangement in FIG. 29, either one or both of the durable housing portion 22 and the disposable housing portion 20 may be provided with a base having an adhesive material 101 (and a peelable cover layer 23 as shown in FIG. 3).

Figure 30:
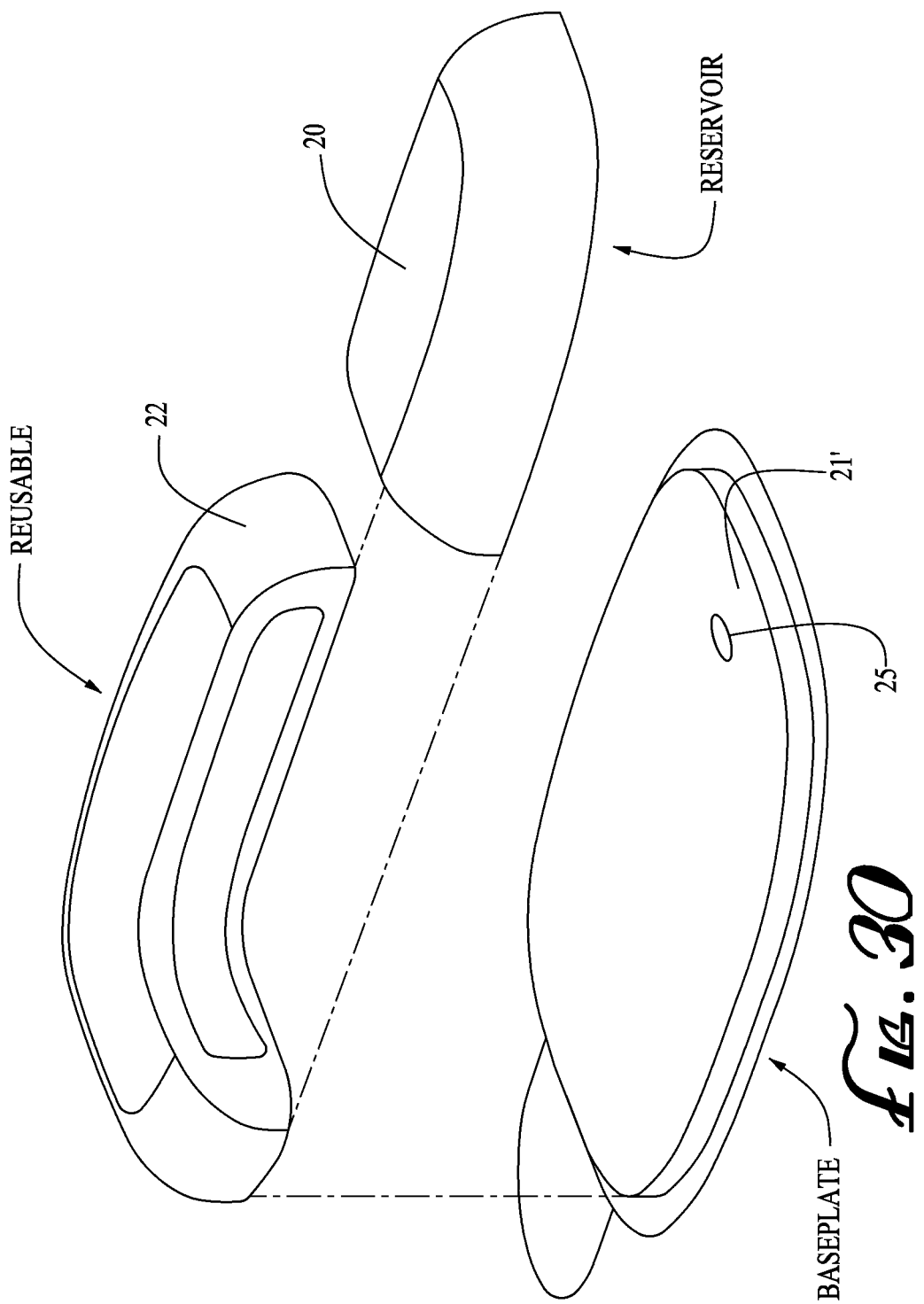
FIG. 30 shows a partially exploded view of a delivery device according to an embodiment of the invention.

In yet further embodiments, as represented by FIG. 30, one or both of the durable housing portion 22 and the disposable housing portion 20 may be attachable and detachable from a separate base member 21'. Suitable connecting structure, such as described above for connecting the durable housing portion and the disposable housing portion together, may be employed for connecting the durable housing portion and the disposable housing portion to the base member 21'. The separate base member 21' may include a generally flat, plate-like structure made of any suitably rigid material including, but not limited to, plastic, metal, ceramic, composite material or the like. The base member 21' has a surface (the upper-facing surface in FIG. 30) to which the disposable housing portion 20 and the durable housing portion 22 may be attached. The base member 21' has a second surface (the lower-facing surface in FIG. 30) to which an adhesive material and a peelable cover film may be applied, as described above, to allow the base member 21' to be secured to a patient-user's skin.

The base member 21' may include a needle inserter device 25, as described above. Examples of suitable needle inserter devices are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. In such embodiments, the base member 21' may be secured to a patient-user's skin. Then, the needle inserter 25 may be activated to insert a hollow needle or cannula into the patient-user's skin. Then, after the hollow needle or cannula is inserted, the durable housing portion 22 and the disposable housing portion 20 may be attached to the base member 21', to connect the reservoir within the disposable housing portion 20 in fluid flow communication with the hollow needle or cannula. In one embodiment, the durable housing portion 22 and the disposable housing portion 20 may be connected together (for example, in the manner described above) before attaching those housing portions to the base member 21'. In a further embodiment, one of the durable and disposable housing portion is attached to the base member 21' before the durable and disposable housing portions are connected together. In such further embodiment, the needle inserter device may be activated to insert a hollow needle or cannula into the patient-user's skin after the disposable housing portion is attached to the base member 21' (either before or after the durable and disposable housing portions are connected together).

Alternatively, reference number 25 may represent an opening in the base member 21' that aligns with a needle inserter device (or aligns with a further opening) located in the disposable housing portion 20, when the disposable housing portion 20 is attached to the base member 21'. In such embodiments, the base member 21' may be secured to the patient-user's skin. Then the disposable housing portion 20 is attached to the base member 21' (either before or after the durable and disposable housing portions are connected together). Once the disposable housing portion 20 is attached to the base member 21', the needle inserter device 25 may be activated to insert a hollow needle or cannula into a patient-user's skin (either before or after the durable and disposable housing portions are connected together). Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Figure 31:
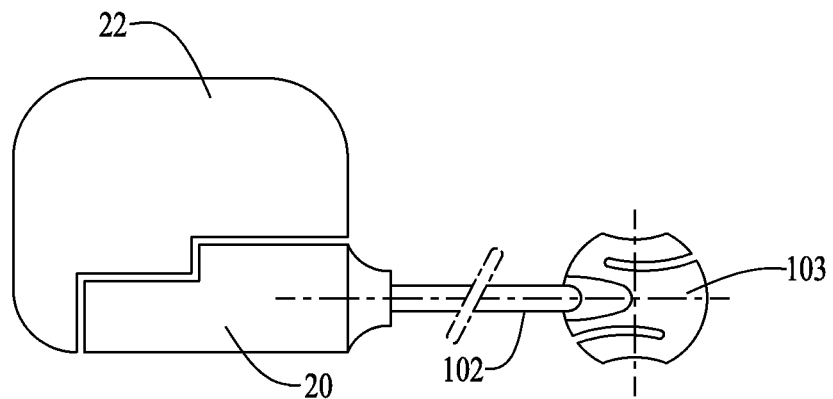
FIG. 31 shows a schematic top view of an arrangement of a durable housing portion and a disposable housing portion of a delivery system according to an embodiment of the invention.

Also, while embodiments described above may include an on-board needle or cannula injector device that may be activated through the operator or opening 25, other embodiments may employ an injection site module 103 that is external to the disposable housing portion 20, but connected to the disposable housing portion 20, through a suitable conduit 102, as shown in FIG. 31. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bathe, swim or conduct other activities, yet also allow the patient-user to readily re-connect the disposable housing portion 20 to the module 103, for example, upon completion of such activities. Examples of connectors can be found in U.S. patent application Ser. No. 10/328,393 filed Dec. 22, 2003, and entitled "Reservoir Connector," and U.S. Pat. No. 5,545,152 issued Aug. 13, 1996, and entitled "Quick-Connect Coupling For A Medication Infusion System," both of which are incorporated herein by reference in their entirety. In other alternatives, different connectors such as Luer locks, or the like may be used.

Figure 32:
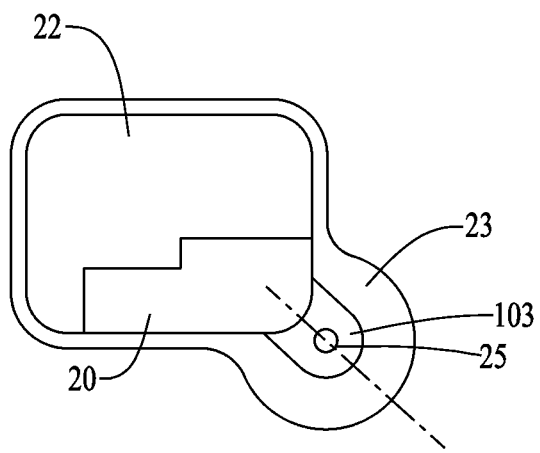
FIG. 32 shows a schematic top view of an arrangement of a durable housing portion and a disposable housing portion of a delivery system according to another embodiment of the invention.

In yet further embodiments, the conduit 102 may be eliminated and an injection site module 103 may be directly connected with the disposable housing portion 20, as shown in FIG. 32. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Figure 33:
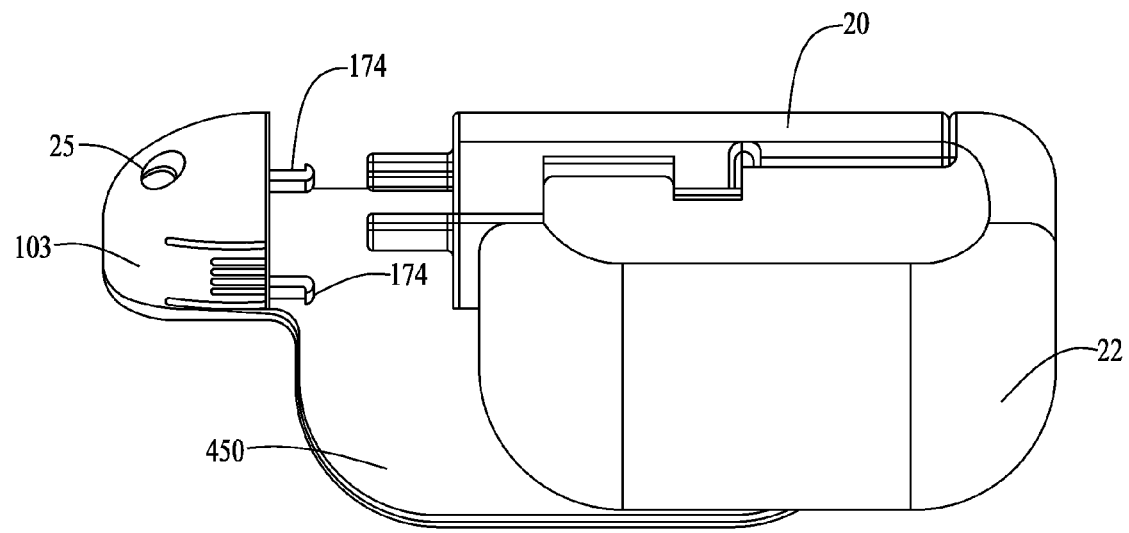
FIGS. 33-34 each show a perspective view of a connection arrangement for a disposable housing portion and an injection site module.
Figure 34:
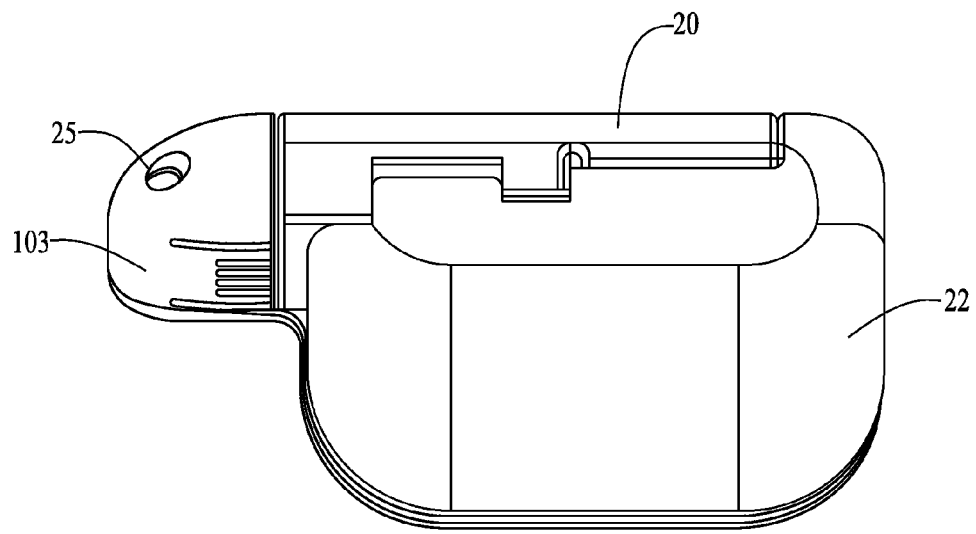
Figure 35:
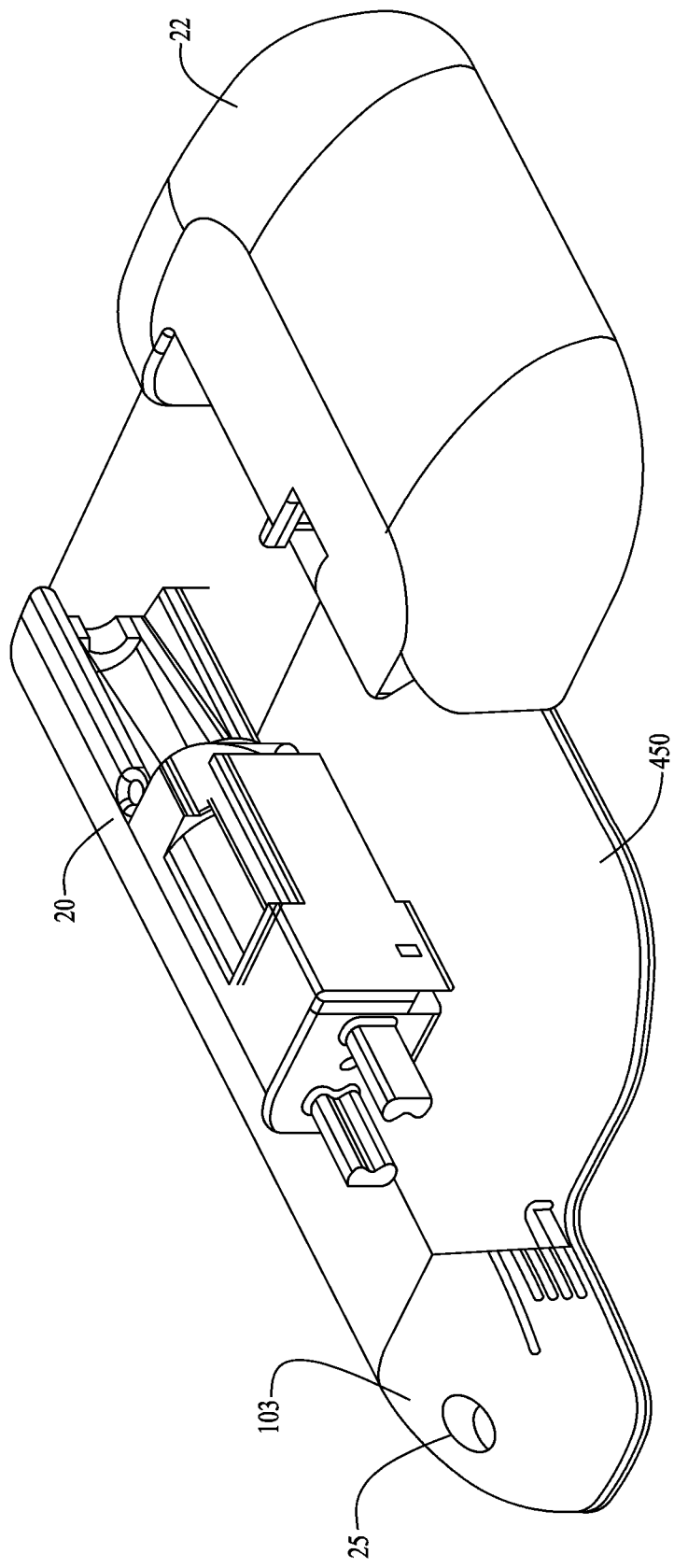
FIGS. 35 and 36 each show a perspective view of another connection arrangement for a disposable housing portion and an injection site module.

Various examples of mating arrangements, for directly connecting an injection site module 103 to a disposable housing portion are described with reference to FIGS. 33-40. FIGS. 33-35 show an example arrangement, in which an injection site module 103 includes at least one (two in FIG. 33) protruding engagement pawl 174 that are configured to be received in a corresponding number of receptacles on the disposable housing portion 20 (similar to the pawls 74 and receptacles 76 described in U.S. Patent Application No. 60/839,741, titled INFUSION PUMPS AND METHODS AND DELIVERY DEVICES AND METHODS WITH SAME, filed Aug. 23, 2006, which has been incorporated herein by reference. In other embodiments, the pawl(s) 174 may be located on the disposable housing portion 20, while the corresponding receptacles may be located on the module 103. In yet other embodiments, each of the disposable housing portion 20 and the module 103 may include one or more pawls and one or more receptacles.

The pawls 174 and receptacles may be configured to allow a patient-user to manually slide the pawls into the receptacles as the disposable housing portion 20 and the module 103 are brought together. When the pawls 174 are received in the corresponding receptacles, the module 103 is secured to the disposable housing portion 20. The pawls 174 may include a shaped portion or head to provide a snap-fit with the receptacles, when the pawls 174 are fully received within the receptacles. The pawls 174 may be configured with sufficient flexibility to allow the patient-user to separate the disposable housing portion 20 from the module 103, by applying a sufficient force to pull those two parts away from each other and unsnap the pawls 174 from the receptacles. In the embodiment of FIGS. 33-35, the module 103 may be attached to or may include a base portion 450 that may be secured to a patient-user's skin during operation, in lieu of the extended base 21 of the disposable housing portion 20 described above. The base portion 450 may include an adhesive material as described herein with respect to the base 21 of the disposable housing portion 20.

As shown in FIG. 35, the embodiment of FIGS. 33-35 may be formed in three general parts, including the disposable housing portion 20, the durable housing portion 22 and the module 103 on the base portion 450. The durable housing portion 22 and the disposable housing portion 20 may be secured together (as shown in FIG. 33), and the combined, connected disposable and durable housing portions may be secured to the module 103 and base portion 450. In one embodiment, the base portion 450 may be secured to a patient-user's skin, before the combined, connected disposable and durable housing portions are secured to the module 103 and base portion 450. In a further embodiment, the combined, connected disposable and durable housing portions are secured to the module 103 and base portion 450, before the base portion 450 is secured to the patient-user's skin.

Figure 36:
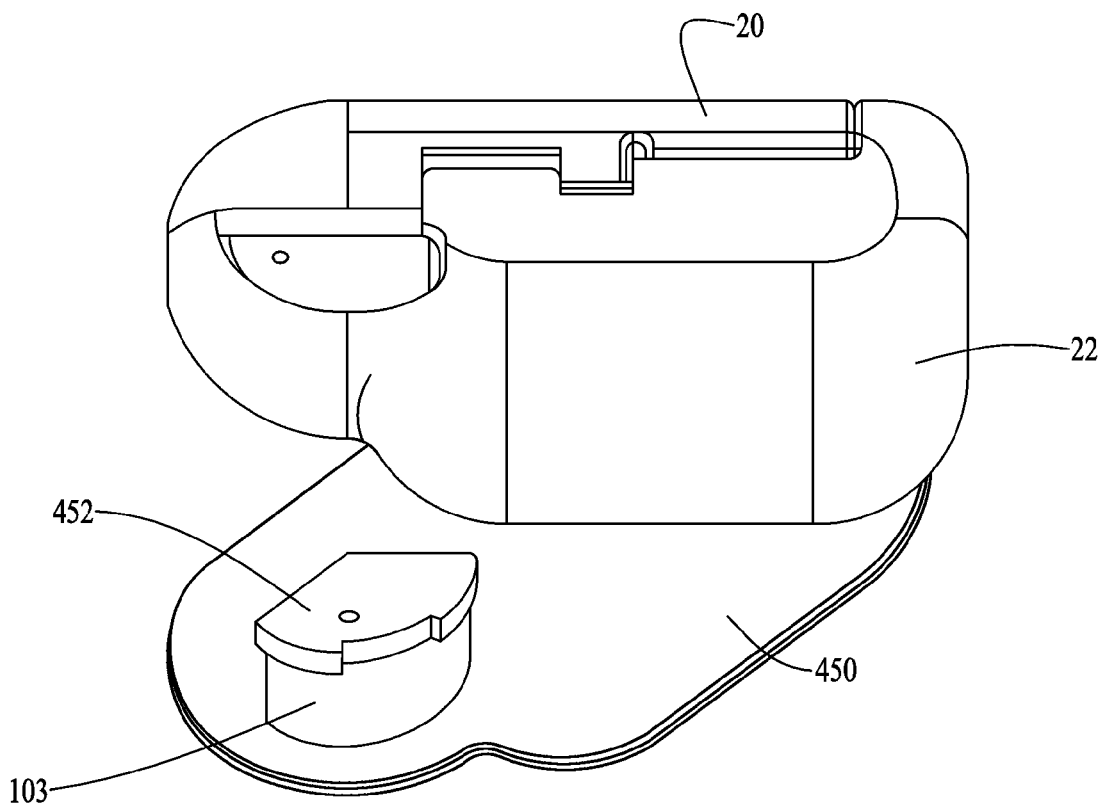
Figure 37:
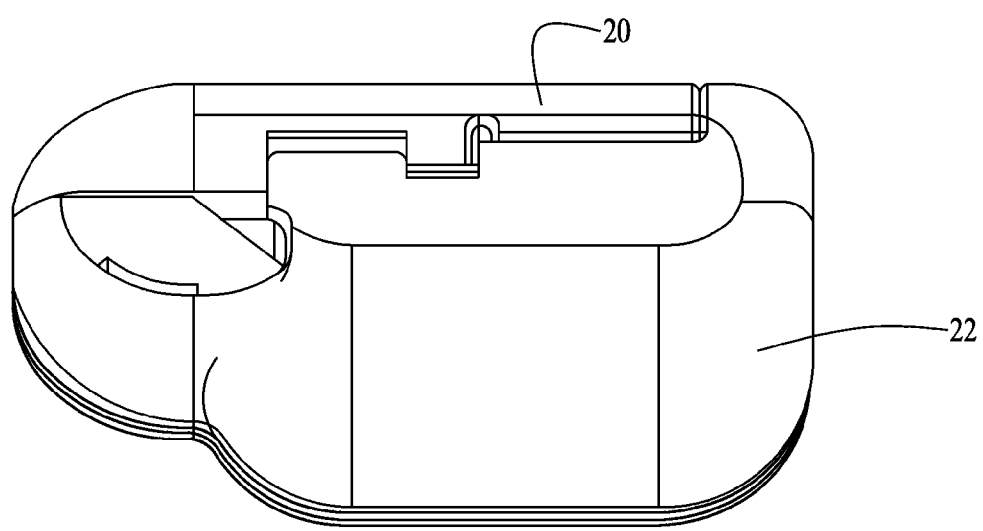
FIGS. 37-40 each show a perspective view of yet another connection arrangement for a disposable housing portion and an injection site module.

Another example of a connection structure is described with reference to FIGS. 36 and 37, wherein the module 103 includes a shaped head 452 configured to be received within a correspondingly shaped opening or receptacle in the disposable housing portion 20. The shaped head 452 may be configured with a shape that allows the head to be received in the receptacle when the disposable housing portion 20 is aligned relative to the module 103 in a first alignment position, as shown in FIG. 36, and further allows the disposable housing portion 20 to be rotated relative to the module 103 while the head 452 is received within the receptacle to a second alignment position as shown in FIG. 37. The receptacle in the disposable housing portion 20 may be shaped to allow the head 452 to be freely received or removed from the receptacle, when the disposable housing portion 20 is in the first alignment position (FIG. 36), yet abut the head 452 and inhibit separation of the head 452 from the receptacle (and, thus, inhibit separation of the disposable housing portion 20 from the module 103), when the disposable housing portion is in the second alignment position (FIG. 37).

Figure 38:
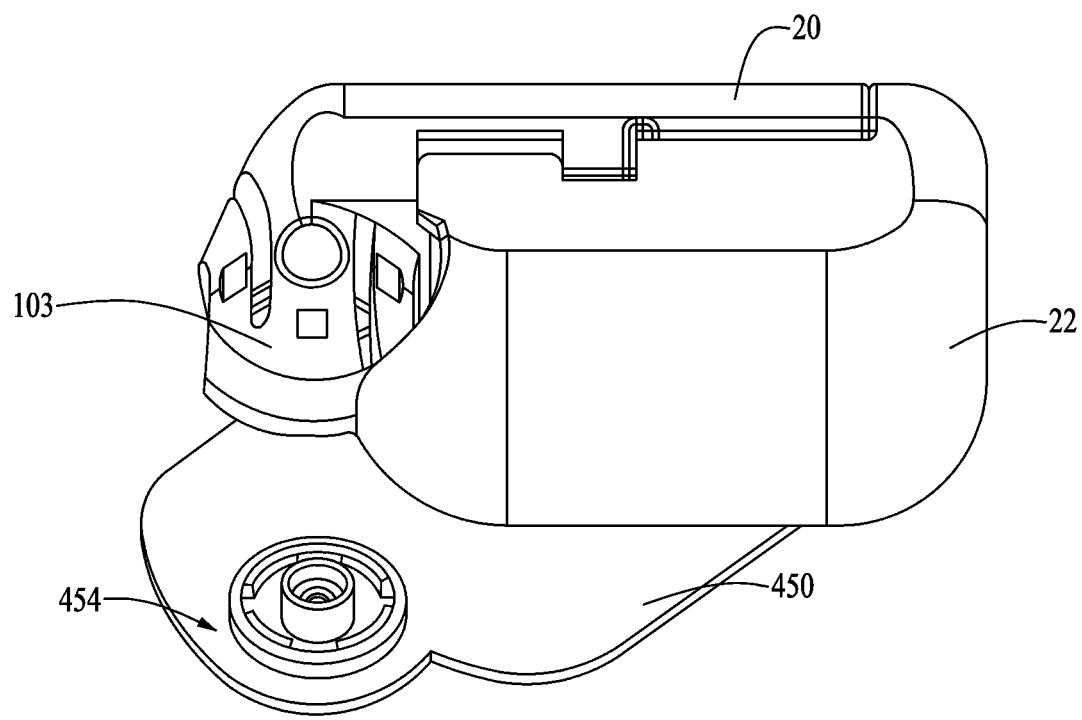
Figure 39:
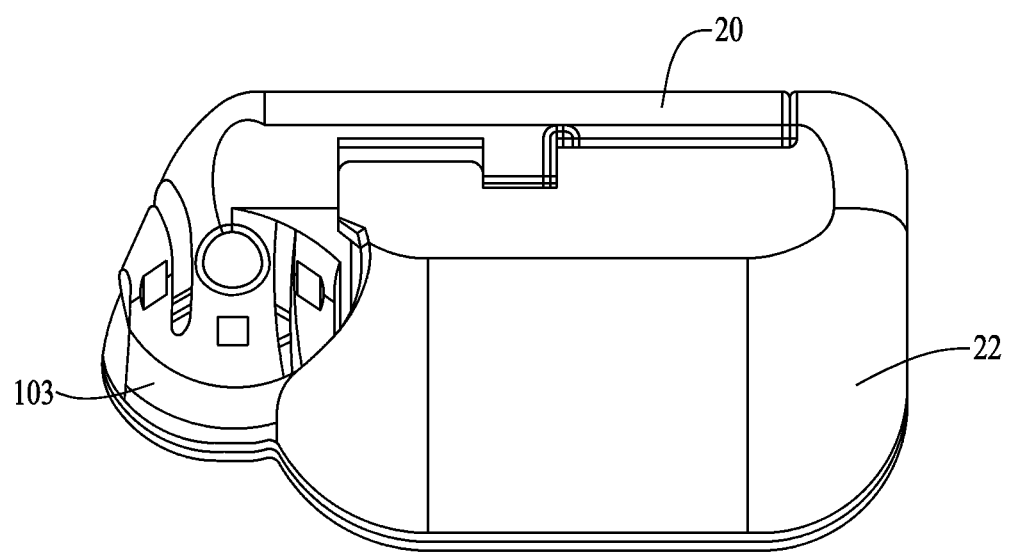
Figure 40:
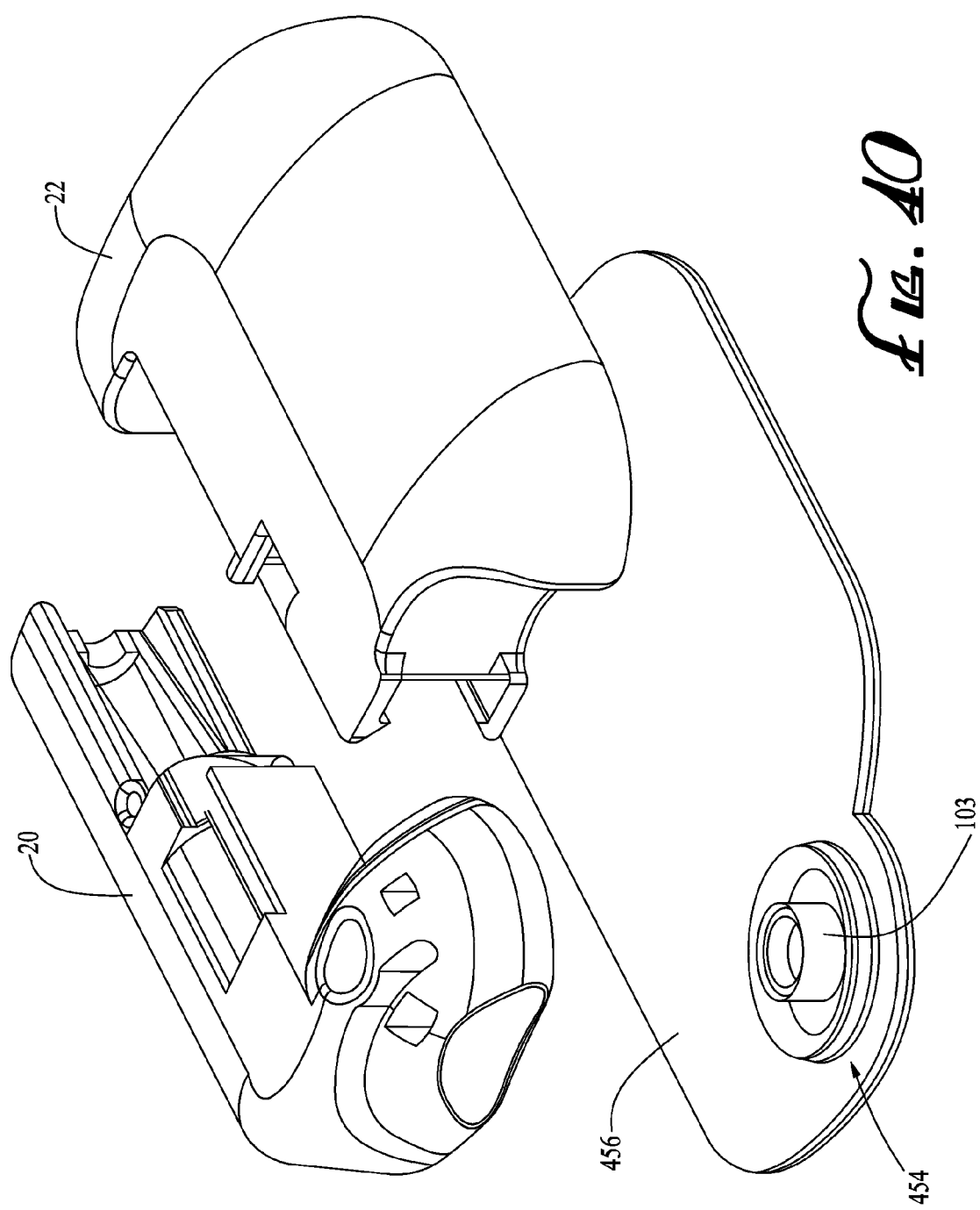

A further example of a connection structure is described with reference to FIGS. 38-40, wherein the device incorporates three parts, the durable housing portion 22, the disposable housing portion 20 and a base 456. A shaped receptacle 454 on the base portion 456 is configured to receive a correspondingly shaped connector member in the disposable housing portion 20. In FIGS. 38-40, the module 103 is formed, integral with the disposable housing portion 20. The shaped receptacle 454 may be configured with a shape that allows the connector member in module 103 to be engaged with the receptacle 454, when the disposable housing portion 20 is aligned relative to the base 456 and receptacle 454 in a first alignment position, as shown in FIG. 38, and further allows the disposable housing portion 20 to be rotated relative to the base 456 and receptacle 454, while the receptacle 454 is engaged within the connector member, to a second alignment position as shown in FIG. 39. The receptacle 454 and the connector member in the disposable housing portion 20 may be shaped to allow the connector member to be freely engage the receptacle 454, when the disposable housing portion 20 is in the first alignment position (FIG. 38), yet lock with the receptacle 454 and inhibit separation of the connector member from the receptacle (and, thus, inhibit separation of the disposable housing portion 20 from the module 103), when the disposable housing portion is in the second alignment position (FIG. 39). The receptacle 454 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction. A motion inhibiting structure, such as a locking tab, pawl or the like, may be provided to inhibit relative motion between the disposable housing portion 20 and the base 456, once those parts have been connected, as described above.

As shown in FIG. 40, the embodiment of FIGS. 38-40 may be formed in three general parts, including the disposable housing portion 20, the durable housing portion 22 and the module 103 on the base portion 456. The durable housing portion 22 and the disposable housing portion 20 may be secured together (as shown in FIG. 38), and the combined, connected disposable and durable housing portions may be secured to the base portion 456. In one embodiment, the base portion 456 may be secured to a patient-user's skin, before the combined, connected disposable and durable housing portions are secured to the base portion 456. In a further embodiment, the combined, connected disposable and durable housing portions are secured to the base portion 456, before the base portion 456 is secured to the patient-user's skin.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain all materials that are in direct contact with the infusion medium, such as reservoir body, reservoir piston, septum systems and injection needle. The non-disposable portion could contain substantially the materials that are not in contact with the medication including the drive system, pressure or force sensing system, battery, electronics, display, and non-disposable housing. The pump could be designed such that the disposable portion (with an unused new, user-filled, prefilled, refurbished, remanufactured or re-filled reservoir 26) is inserted into the non-disposable portion. By simplifying the manner in which the disposable portion of the delivery device can be replaced and by simplifying the manner in which the delivery device can be re-activated after replacing a disposable portion, a greater number of patient-users will be able to use and benefit from such delivery devices.

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23, to allow the delivery device to be secured, removed and re-secured to the patient-user's skin one or more times.

In such embodiments, a first cover film layer located at the end of the stack of alternating layers of adhesive material and cover film, may be removed to expose a first layer of adhesive material. With the first layer of adhesive material exposed, the delivery device (or component thereof) may be adhered to a patient-user's skin, as described above. After a suitable period of usage, the delivery device (or component having the adhesive) may be removed from the patient-user's skin, for example, for servicing, re-filling, replacement of one or more components, or the like. After removal of the delivery device (or component) from the patient-user's skin, a second cover film layer on the delivery device (or component) may be removed to expose a second layer of adhesive material. With the second layer of adhesive material exposed, the delivery device (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while embodiments described above include an injection site located on the disposable housing portion 20 or in an external injection site module 103, other embodiments may employ an injection site located in the durable housing portion 22 and connected, through suitable fluid-flow passages, to the reservoir in the disposable housing portion 20, when the durable housing portion and disposable housing portion are engaged. Also, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

Also, various embodiments described above may employ a reservoir 26, 126, 226, 326, 426 that, in some examples, may comprise a canister that is removable from and insertable into the first or disposable housing portion 20. In this manner, a reservoir cartridge may be removed and replaced with a new, refilled, pre-filled, user-filled, refurbished or remanufactured cartridge. In such embodiments, the reservoir cartridge may include an electronic storage device (such as an electronic memory chip or the like) for storing information, such as, but not limited to, identification of the contents of the reservoir, identification of the maker of the reservoir or its contents, information relating to the state of fill or depletion of the reservoir, or the like. Suitable electrical contact pads located in the disposable housing portion may electrically connect with contact pads on the reservoir, to electrically connect the electronic storage device on the reservoir canister with suitable electronics in the disposable housing portion or the durable housing portion 22, for reading information stored on the electronic storage device. Such information (or other information, warnings, etc., associated with the stored information) may be displayed on a display device on the durable housing portion 22, when the reservoir canister is inserted into the disposable housing portion 20, and the disposable housing portion 20 and the durable housing portion 22 are engaged.

In addition, in any of the above-described embodiments, one or both of the disposable housing portion 20 and the durable housing portion 22 (and/or a separate base portion 21' or 450 or a separate injection site module 103) may include a force sensor (not shown) or other suitable sensing device for sensing the proper placement or engagement of one or more of the disposable housing portion 20 and the durable housing portion 22 (and/or a separate base portion or a separate injection site module) on a patient-user's skin (or other proper location for operation with the patient). In such an embodiment, further electronics may control the operation of the drive device to inhibit operation of the drive device and/or the needle injector, unless the sensor senses the proper operable engagement of one or more of the disposable housing portion 20 and the durable housing portion 22 (and/or a separate base portion or a separate injection site module) with the patient-user's skin (or other proper location for operation).

Alternatively or in addition, one or both of the disposable housing portion 20 and the durable housing portion 22 may include a sensing device (not shown) for sensing the proper operable engagement of the disposable housing portion 20 and the durable housing portion 22 together (and/or with a separate base portion or a separate injection site module). In such an embodiment, further electronics may control the operation of the drive device to inhibit operation of the drive device and/or the needle injector, unless the sensor senses the proper operable engagement of the disposable housing portion 20 and the durable housing portion 22 together (and/or with a separate base portion or a separate injection site module).

In any of the above embodiments, a sensor may be provided in (or otherwise associated with) the reservoir to detect a low volume of infusion medium in the reservoir. For example, a sensor may be configured to detect a condition at which the volume of infusion medium in the reservoir reaches a threshold minimal level. A warning device may be operably connected to the sensor, to provide a warning signal, upon the detection of a low volume condition. The warning device may provide an audible warning sound, a visible warning signal and/or a tactile warning signal (such as, but not limited to a perceptible vibration) to the patient-user, upon the detection of the volume of infusion medium in the reservoir reaching a threshold minimal level. In one embodiment, the visible warning may be provided as a message on an electronic display (as described above) on the durable housing portion 22. Alternatively or in addition, a warning signal condition may be communicated to and displayed on a remote CCD 16 or computer 18 (FIG. 2), for example, through wireless communication electronics as described above.

In addition, while various embodiments described above may include one or more adhesive layers, each having a peelable cover layer, other embodiments may employ a single adhesive layer having (or plural adhesive layers, each having) a pattern of plural peelable cover layer portions, such that a patient-user may peel off one portion of the cover layer for adhering the delivery device to the patient-user as described above, while leaving the rest of the pattern of peelable cover layer portions on the adhesive. In such an embodiment, after completion of a first period of operation of the delivery device and removal of the delivery device from the patient-user, a second portion of the peelable cover layer may be removed from the adhesive layer and the delivery device may be adhered to a patient-user for a second period of operation.

Also, while various delivery device embodiments described above include base portions (for example, 21, 21' and 450) that are configured to be secured to a patient-user's skin (or other suitable surface of operation) and that extend along the full length and width of the delivery device structure, other embodiments may employ base portions (that secure to the patient-user's skin or other surface) that are configured to be less than the full length or width dimension of the delivery device structure, to minimize the surface area in contact with the patient-user (or other surface) and, thus, improve patient-user comfort during operation. Base portions having shapes and sizes different from those shown in the accompanying drawings may be employed for additional improvements with regard to patient-user comfort and minimizing surface area in contact with the patient-user. Furthermore, as noted above, the base portion may be composed of a flexible material that at least partially conforms to the curvature and movement of the patient-user's body.

In any of the above-described embodiments in which an adhesive material is used to secure one or more of the delivery device components to the patient-user's skin (or other suitable surface for operation), multiple types of adhesive materials (or multiple strengths of adhesives) may be employed, such that a stronger adhesive is provided in certain areas (such as around the needle injection site), while a weaker adhesive is provided in other areas.

As described above, an infusion medium delivery device may include multiple connectable parts that connect together for operation, but may disconnect and separate from each other for servicing, replacement, inspection, or the like. Embodiments may include one or more housing portions (for example, referred to herein as a disposable housing portion 20 and a durable housing portion 22) that are selectively connectable to and separable from a base portion (such as, but not limited to a base portion 21', 450 or 456 described above). In further embodiments, the base portion may be incorporated into one or more of the housing portions (such as, but not limited to, the arrangements shown in FIGS. 2, 3, 28 and 29). In yet further embodiments, connectable parts may comprise an injection site module (such as module 103 described above) that is selectively connectable to and separable from a base portion or a durable or disposable housing portion, as described above.

In addition to, or as an alternative to, any of the connection structure described above for allowing one or more parts of the infusion device to be selectively connectable to, and separable from, one or more other parts of the infusion delivery device, any of the above described embodiments (or other suitable embodiments) may include one or more magnets as described below. The magnet(s) may function to provide one or more of aligning connectable parts, connection of connectable parts, and sensing the connection of connectable parts, as described below.

A generalized representation of a two connectable parts 500 and 502 of an infusion delivery device as described above is shown in FIG. 41. The parts 500 and 502 may be two housing portions, such as, but not limited to, a durable housing portion 22 and a disposable housing portion 20, as described above. Alternatively, one of the parts 500 and 502 may be a base portion (such as, but not limited to, the base portions 21', 450 and 456 described above) and the other of the parts 500 and 502 may be a housing portion (such as, but not limited to a durable housing portion 22 and/or a disposable housing portion 20) as described above.

According to an embodiment of the present invention, one of the infusion device parts (500 in FIG. 41) is provided with a first magnet 504. The first magnet 504 may be arranged in a fixed relation to the part 500, for example, by attaching the magnet 504 to a suitable location on a wall or on other structure of or in the part 500. The other infusion device part (502 in FIG. 41) is provided with a second magnet 506. The second magnet 506 may be arranged in a fixed relation to the part 502, for example, by attaching the magnet 506 to a suitable location on a wall or on other structure of or in the part 502.

The magnets 504 and 506 may be suitable permanent magnets and/or electromagnets. In embodiments in which one or both of the magnets 504 and 506 are electromagnets, suitable electronics are connected to the electromagnets to provide a controlled power signal to selectively activate the electromagnets. For example, electromagnets may be controlled to activate upon a manual activation of a control button, switch (or other manual operator) on one of the connectable components (or on a remote-controller device that is connected in wireless communication with the electromagnet(s) through suitable control electronics). In yet other embodiments, the electromagnets may be controlled to activate, upon the activation of a needle inserter to insert a needle or cannula, as described above.

The first magnet 504 is arranged in a location to magnetically interact with the second magnet 506, when the first part 500 and the second part 502 are in relative close proximity to each other. Also, the first and second magnets 504 and 506 are arranged with their poles facing opposite to each other, such that the pole of the first magnet 504 that faces the second magnet 506 is opposite to the pole of the second magnet 506 that faces the first magnet 504. In the illustrated embodiment, the south pole of the first magnet 504 is arranged to face the second magnet 506, while the north pole of the second magnet 506 is arranged to face the first magnet 504. In other embodiments, the pole faces may be reversed.

When the first part 500 and the second part 502 are aligned for connection and brought into proximity to each other, the facing poles of the first and second magnets 502 and 504, being of opposite polarity, provide an attraction force, for attracting the first and second parts 500 and 502 together. According to certain embodiments, the magnets provide a sufficient attraction force to operate to connect the first part 500 to the second part 502, when the parts 500 and 502 are brought in sufficiently close proximity to each other. Multiple pairs of first and second magnets may be provided on the first and second parts 500 and 502, respectively, with their opposite-facing poles, as described above with respect to first and second magnet 502 and 504, for example, to provide a stronger and more stable connection between the first and second parts 500 and 502.

In the illustrated embodiment, a second pair of magnets 502' and 504' are shown as supported by the first and second parts 500 and 502 in a manner similar to that described above for magnets 502 and 504. In further embodiments, more than two pairs of magnets 502 and 504 may be supported by the parts 500 and 502, as described above. In further embodiments, one of the magnets 504 or 506 (and/or 504' or 506') may be replaced with a magnetically attractive material, such as, but not limited to a ferrous material including an iron or iron alloy, or the like. In such further embodiments, the remaining magnet 504 or 506 provides an attraction force on the magnetically attractive material, to provide a connection operation as described above.

Accordingly, as part of a process of assembling a first part 500 and a second part 502 of an infusion device, a user may bring the two parts into sufficiently close proximity to allow the magnets 504 and 506 and magnets 504' and 506' (or one of those magnets and a magnetically attractable material) to provide a sufficient attraction force to draw the two parts 500 and 502 together and to connect the parts 500 and 502 together. The magnets 504 and 506 (or multiple pairs of magnets 504, 506 and 504', 506') may provide a sufficient force to connect the two parts 500 and 502 together in a securable manner for operation of the infusion device. In further embodiments, additional connection structure as described above may be provided to further secure the two parts 500 and 502 together for operation of the infusion device.

In addition to, or as an alternative to providing a connection function, magnets 504 and 506 (or one of those magnets and a magnetically attractable material) may help a user align the first and second parts 500 and 502 relative to each other, for proper connection. For example, one or more pairs of magnets 504, 506 and/or 504', 506' (or of one of those magnets and a magnetically attractable material) may be arranged at one or more appropriate locations on the two parts 500 and 502, and may be of suitable sizes, shapes and positions such that the patient-user (or other person assembling the parts) may feel the greatest attraction force drawing the magnets 504 and 506 and/or magnets 504' and 506' (or magnet and attractable material) together, when the two parts are properly aligned in multiple dimensions, relative to each other.

Additional structural features may be provided on one or both of the first and second parts 500 and 502, to provide a mechanical alignment function. In the illustrated embodiment, such additional structural features include a first sloping surface 500a on the first part 500 that is arranged to engage a corresponding, mating sloping surface 502a on the second part 500. As the parts 500 and 502 are brought together, a slight misalignment of the parts will result in the sloped surfaces 500a and 502a engaging each other in a position at which the surfaces will slide relative to each other toward a proper alignment position. Multiple sloping surfaces arranged at opposite sides of the parts 500 and 502 may be provided (as represented by the second set of mating, sloping surfaces 500b and 502b), to provide alignment in multiple directions and multiple dimensions. While the illustrated embodiment includes mating, sloping surfaces, other embodiments may include other suitable structural features to aid in the alignment, including, but not limited to, curved or stepped surfaces, rollers or the like on the parts 500 and 502 that abut as the parts 500 and 502 are brought together for connection. While the additional structural features for alignment shown in FIGS. 41 and 42 include mating, sloped surfaces that are provided on the parts 500 and 502, other embodiments may employ a mating, sloped (or otherwise shaped) surface on one or both magnets 504 and 506, for engaging and providing an alignment function, when the parts 500 and 502 are brought together for connection.

Figure 41:
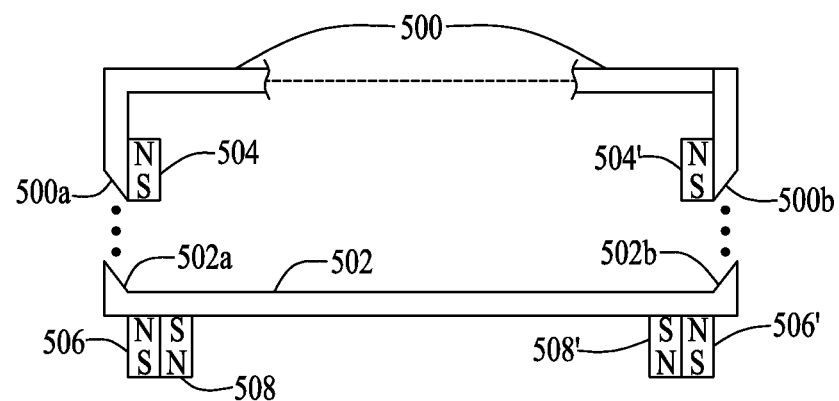
FIG. 41 is a generalized, partial cross-section view of two connectable parts of an infusion medium delivery device according to an embodiment of the present invention.

In the embodiment of FIG. 41, two pairs of magnets 504, 506 and 504', 506' are shown, with one on each side of the drawings, as a non-limiting, illustrative example. As an alternative or addition to the use of one or more pairs of magnet 504, 506 and 504', 506' (or of one of those magnets and a magnetically attractable material) for alignment, further embodiments may employ one or more pairs of magnets that are arranged on the two parts 500 and 502 with common poles facing each-other when the two parts 500 and 502 are brought together for connection. In the embodiment of FIG. 41, the pairs of magnets that define the alignment pair with common poles facing each other are the magnets 504 (and 504') on the part 500 and the magnets 508 (and 508') on the part 502.

In FIG. 41, the south poles of the magnets 504 and 508 are arranged to face toward each other, when the two parts 500 and 502 are brought together for connection. In other embodiments, the north poles of the magnets 504 and 508 may be arranged to face toward each other, when the two parts 500 and 502 are brought together for connection. Also, in other embodiments, one or more separate magnets (other than the magnets 504 that are used for attraction with magnets 506 as described above) may be included for alignment interaction with a magnet 508 as described herein. The magnets 508 and 508' may include any suitable magnet structure as described above with respect to magnets 504 and 506.

The alignment pair of magnets with common poles facing each other are arranged to be laterally offset from each other a sufficient distance to allow the two parts 500 and 502 to be brought together in proper alignment with respect to each other, while providing a sufficient opposition force to force the parts 500 and 502 apart when the two parts 500 and 502 are brought toward each other into a close, but improper alignment relative to each other. One or more pairs of magnets 504 and 508 may be appropriately arranged on the parts 500 and 502, respectively, such that, as a patient-user (or other person assembling the parts 500 and 502) brings the two parts 500 and 502 together for connection, the two parts 500 and 502 need only be brought into close alignment (rough alignment), whereupon the magnet pairs 504 and 508 assist the alignment process by not allowing the two parts 500 and 502 to come together until a proper alignment is achieved (and, in some embodiments, effectively forcing the two parts 500 and 502 toward a proper alignment position).

When the two parts 500 and 502 are brought together in proper alignment for connection, the magnet 508 on the part 502 is at a position that is laterally offset from the position of magnet 504 on the part 500. The lateral offset is in a direction generally perpendicular to the direction in which the two parts 500 and 502 are moved relative to each other to bring the two parts together. In the illustrated embodiment, the lateral offset is shown as an offset spacing in the horizontal-widthwise direction of the drawing, wherein one of the two magnets 504 and 508 (508 in FIG. 41) is arranged closer to a center position of its corresponding part (part 502 in FIG. 41) than the other magnet (504 in FIG. 41) on the other part (part 500 in FIG. 41), when the two parts 500 and 502 are in proper alignment for connection.

A similar arrangement of two magnets 504 and 508 that are offset from one another, with one of the magnets arranged closer to the center position of its corresponding part (508' in FIG. 41) is arranged closer to a center position of its corresponding part (part 502 in FIG. 41) than the other magnet (504' in FIG. 41) on the other part (part 500 in FIG. 41), when the two parts 500 and 502 are in proper alignment for connection. For example, by arranging two or more magnet pairs 504, 508 and 504', 508' in positions that are offset from each other as described above, the opposing forces provided by the facing common poles of each respective magnet pair can assist a patient-user (or other person assembling the parts) to properly align the parts 500 and 502 in multiple dimensions. In embodiments that also employ a magnet 506, with an opposite pole facing the pole of the magnet 504, when the parts 502 and 104 are in proper alignment for connection, the magnet pair(s) 504 and 508 (and 504' and 508') can guide alignment from an initial roughly aligned state to a properly aligned state, at which state the magnet pair(s) 504 and 506 (and 504' and 506') attract the parts 502 and 504 together into a properly aligned, connection position relative to each other.

In addition to or as an alternative to either or both of the attracting pairs of magnets (504, 506 and 504', 506') and opposed pairs of magnets (504, 508 and 504', 508') described above, further embodiments represented by FIG. 42 may include a magnet-responsive device 510, such as a magnetically activating switch or other suitable magnet detector that produces an electronically detectable state or signal upon being in sufficiently close proximity to a magnet. In certain embodiments, the device 510 may include a conventional magnetically activating switch or a conventional device capable of detecting magnetic fields.

One or both of the parts 500 and 502 may include a magnet-responsive device supported by the respective part 500 and 502 in a position to be activated, only when the parts 500 and 502 are brought into a pre-defined, sufficiently aligned position and in a pre-defined, sufficiently close proximity. The predefined aligned position and proximity, for example, may correspond to a properly aligned and mutually proximate position for connection of the two parts 500 and 502 for operation.

Figure 42:
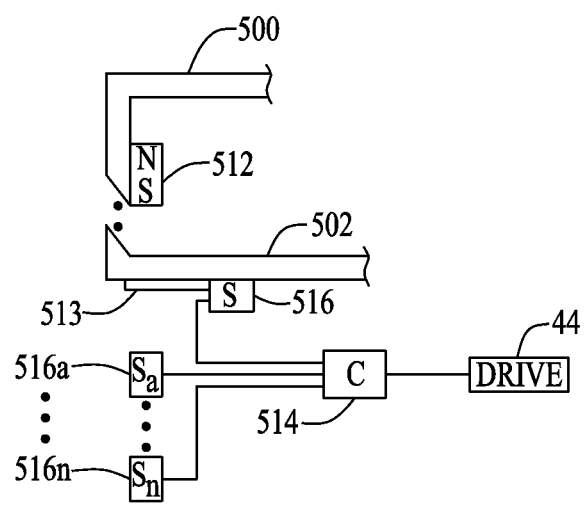
FIG. 42 is a generalized, partial cross-section view of two connectable parts of an infusion medium delivery device according to a further embodiment of the present invention.

In FIG. 42, a magnet-responsive device 510 is provided on the part 502, while a magnet 512 for activating the magnet-responsive device 510 is provided on the part 500. In other embodiments, a similar magnet-responsive device 510 may be provided on the part 500 and an associated magnet 512 may be provided on the part 502, either in addition to or as an alternative to the arrangement shown in FIG. 42. In yet further embodiments, multiple pairs of magnet-responsive devices 510 and magnets 512 may be provided on the parts 500 and 502. In certain embodiments, the magnet 512 may be one of the magnets 504, 506 or 508 described above. In other embodiments, the magnet-responsive device 510 and magnet 512 may be independent of (in addition to or as an alternative to) the magnets 504, 506 and 508.

In embodiments as shown in FIG. 42, in which a magnet 504 on the first part 500 functions with a magnetically attractive material 513 on the second part 502 (instead of or in addition to a magnet 506) to provide a magnetic attraction for assisting in aligning and/or connecting the parts 500 and 502 together as described above, a magnet-responsive device 516 may be located at a position adjacent the magnetically attractive material 513, but remote from the location of the magnet 512 on the first part 500 (and any alignment magnet (corresponding to magnet 508 described above) on the second part 502. In such embodiments, the magnetically attractive material 513 on the second part 502 becomes magnetized by the magnet 512 on the first part 500, to activate the remote device 516 when the first and second parts 500 and 502 are brought together for connection.

The magnet-responsive device 510 is connected in electrical communication with control electronics 514. The control electronics 514 may be incorporated within the control electronics for controlling a drive device (such as, but not limited to, the control electronics 52 for controlling the drive device 44 described above with respect to FIG. 4). Alternatively, the control electronics 514 may be separate from and in addition to the control electronics 52, but connected in electrical communication with the control electronics 52 and/or the drive device 44, to provide a drive control signal to the drive device. More specifically, the control electronics 514 is configured to inhibit operation of the drive device 44, unless the magnet-responsive device 510 is activated by the magnet 512 (upon the parts 500 and 502 being in proper alignment and sufficiently close proximity to connect for operation). In one embodiment, the control electronics 514 may provide a detect signal (such as, but not limited to an electronic signal, flag setting or other indicator) to the control electronics 52 and/or drive device 44, upon activation of the magnet-responsive device 510 by the magnet 512. In that embodiment, the control electronics 52 and/or drive device 44 may be configured to allow operation of the drive device 44, only upon the presence of the detect signal.

As discussed above, in certain embodiments, multiple pairs of magnet-responsive devices 510 and magnets 512 may be provided on the parts 500 and 502 and connected to the control electronics 514. In such embodiments, the multiple pairs of devices 510 and magnets 512 may be located, for example, at different respective positions around or within the parts 500 and 502, to provide multiple alignment readings from different locations. In such embodiments, for example, the control electronics 514 may be configured to provide a detect signal (to allow operation of the drive device 44) only upon an activation of all (or a predefined number or set of) the magnet-responsive devices 510.

In yet further embodiments, additional sensors 516a-516n may be provided within the infusion device and connected for electrical communication with the control electronics 514. Such additional sensors 516 may comprises magnetically actuating switches, magnetic field magnitude and direction sensors, inductive sensors, other proximity sensors, contact sensors or the like, for providing a detectable signal or state upon proper connection of other components in the infusion device. Such proper connection of other components may comprise one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the infusion device. Alternatively, or in addition, the sensors 516a-516n may include one or more flow detectors, for detecting the occurrence or blockage of a fluid flow path in the infusion device. In such embodiments, the control electronics 514 may be configured to provide a detect signal (to allow operation of the drive device 44) only upon an activation of all (or a predefined number or set of) the magnetically responsive devices 510 and a proper state of sensors 516a-516n.

The control electronics 514 (FIG. 42) and/or control electronics 52 (FIG. 4) may be configured to control the drive device 44 (FIG. 4) in various manners, in accordance with various different embodiments of the invention. For example, the drive device 44 may be controlled to stop pumping (delivery) operation, immediately upon a detection of an interruption of a fluid-flow path or a disconnection of a critical component in the infusion device, such as, but not limited to, a disconnection of a housing portion from another housing portion or from a base portion, a disconnection of a conduit from another conduit or from a reservoir, a disconnection of a reservoir from a housing portion or a base, or the like.

In alternative or in addition, the control electronics 514 (FIG. 42) and/or control electronics 52 (FIG. 4) may be configured to detect a first-time connection of parts 500 and 502 (or a first-time connection of other components in the infusion device), when the parts 500 and 502 (or other components) are connected for a first-time use, as compared to a re-connection after previous or partial usage. In this manner, the drive device 44 may be controlled to provide a priming operation (or other suitable first-time operation), upon detection of a first-time connection of the parts.

In alternative or in addition, the control electronics 514 (FIG. 42) and/or control electronics 52 (FIG. 4) may be configured to provide an electronic, user-perceptible indication of the proper alignment and/or connection of parts 500 and 502. For example, upon the detection of a proper alignment and/or connection of the parts 500 and 502 (or upon the detection of the connection of other components, such as, but not limited to the connection of a reservoir to a housing portion 500, or the connection of an injection site module to one or both connected parts 500 and 502), the control electronics 514 (FIG. 42) or 52 (FIG. 4) provides a suitable control signal to activate an indicator device (not shown). The indicator device may include, but is not limited to, an audible indicator, an optical indicator, a tactile indicator, combinations of one or more those indicators, or the like. For example, upon a proper alignment or connection of components as described above, an audible beeping sound (or other suitable sound) may be generated by a sound generating device in one of the parts 500 and 502, an LED (or other light source) on one of the parts 500 and 502 may be operated to produce an on or flashing state, and/or a vibration may be generated by a vibration generator in one of the parts 500 and 502.

In yet further embodiments, a signal may be communicated (from a transmitter in one of the parts 500 and 502) to a remotely located communication device (such as, but not limited to, a hand-held controller, a computer, or the like) to provide one or more of the above-noted user-perceptible indications to a user of the remote device. In yet further embodiments, a text or graphic message may be displayed on a display screen on one of the parts 500 and 502 and/or on the remotely located communication device, as an indicator of a proper (or improper) alignment or connection of the parts 500 and 502.

While different embodiments may employ different arrangements of magnets, magnetically attractive material and/or magnet-responsive devices 516 on the parts 500 and 502, in embodiments in which one of the parts 500 and 502 is intended to be disposable (for example, disposed of after one or a prescribed number of uses or period of use), magnets may be provided on the disposable part, while a magnetically attractive material (that is not magnetized by itself) and/or magnet-responsive devices may be provided on a durable part. As a result, after a period of usage, the magnet(s) on the disposable part that may have attracted and collected stray material can be disposed of with the disposable part. On the other hand, the magnetically attractive material (that is not magnetized by itself) can be sufficiently clean and free of stray material for further usage.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A medical device for delivering an infusion medium to a user, the medical device comprising:
    a first housing portion adapted to be carried by a user;
    a second housing portion configured to be selectively operatively engaged with and disengaged from the first housing portion;
    a reservoir connected to one of the first and second housing portions;
    at least one of a drive device or a needle inserting device supported by the other of the first and second housing portions relative to the respective housing portion to which the reservoir is connected, such that upon the first and second housing portions being operatively engaged, the reservoir is operatively coupled to at least one of the drive device or the needle inserting device;
    a first magnet supported on the first housing portion; and
    a second magnet supported on the second housing portion in a position to magnetically interact with the first magnet upon the first and second housing portions being improperly aligned when brought toward each other for operative engagement;
    wherein the first and second magnets are positioned relative to each other so as to impart a repelling force directed toward properly aligning the first and second housing portions for operative engagement.

2. The medical device according to claim 1, wherein the second magnet is supported on the second housing portion in a position to repel the first magnet upon the first and second housing portions being improperly aligned when brought toward each other for operative engagement.

3. The medical device according to claim 1, wherein one of the first magnet and the second magnet is arranged closer to a center position of the first housing portion than the other of the first magnet and the second magnet to a center position of the second housing portion.

4. The medical device according to claim 1, wherein the first and second magnets are positioned relative to each other so as to impart a repelling force directed toward properly aligning the first and second housing portions for operative engagement, when the first and second housing portions are not properly aligned when brought toward each other for operative engagement.

5. The medical device according to claim 1, wherein the first and second magnets are positioned laterally offset from each other upon the first and second housing portions being operatively engaged.

6. The medical device according to claim 1, wherein the first housing portion includes a first surface for engaging a corresponding surface on the second housing portion, upon the first and second housing portions being operatively engaged, wherein the first surface of the first housing portion and the corresponding surface on the second housing portion are shaped to mate with each other, upon the first and second housing portions being operatively engaged.

7. The medical device according to claim 6, wherein the first surface and the corresponding surface each comprise a sloping surface.

8. The medical device according to claim 7, wherein the sloping first surface and the sloping corresponding surface are arranged to abut and to force the first and second housing portions toward an aligned position for operative engagement, upon the first and second housing portions being brought together for operative engagement.

9. The medical device according to claim 1,
wherein when the first housing portion and the second housing portion are in a first state of engagement, the first magnet is supported on the first housing portion in alignment with the second magnet;
wherein when the first housing portion and the second housing portion are in a second state of engagement, the first magnet is supported on the first housing portion in a position that is laterally offset from the second magnet.

10. The medical device according to claim 9, wherein the second state of engagement corresponds to a proper operative engagement of the first housing portion and the second housing portion.

11. The medical device according to claim 1, wherein one or more of the first magnet or the second magnet is configured to inhibit vertical alignment between each other.

12. The medical device according to claim 1, the device further comprising:
at least one of a third magnet or an attractive material supported on the second housing portion in a position to magnetically interact with the first magnet upon the first housing portion and the second housing portion being operatively engaged;
wherein the first magnet is configured to be attracted to the at least one of the third magnet or the attractive material.

13. The medical device according to claim 1, the device further comprising:
a magnet-responsive device supported on the second housing portion in a position to magnetically interact with the first magnet upon the first housing portion and the second housing portion being operatively engaged.

14. The medical device according to claim 13, wherein the first magnet is configured to magnetically interact with the magnet-responsive device when the first magnet contacts the magnet-responsive device or a magnetically attractive material adjacent the magnet-responsive device.

15. The medical device according to claim 13, wherein the first magnet is configured to be attracted to at least one of the magnet-responsive device and a magnetically attractive material adjacent the magnet-responsive device.

16. The medical device according to claim 1, wherein
the first housing portion and the second housing portion are moveable relative to each other in a first direction, to selectively operatively engage with or disengage from each other;
the first and second magnets are offset relative to each other along a direction transverse to the first direction, when the first housing portion and the second housing portion are operatively engaged with each other.

17. The medical device according to claim 1, wherein
the first housing portion and the second housing portion are moveable toward or away from each other in a first direction, to selectively operatively engage with or disengage from each other;
the first and second magnets are arranged to repel each other along the first direction, when the first housing portion and the second housing portion are improperly aligned when moved toward each other for operative engagement.

18. The medical device according to claim 17, wherein
the first and second magnets are offset relative to each other along a direction transverse to the first direction, when the first housing portion and the second housing portion are operatively engaged with each other.

19. A medical device for delivering an infusion medium to a user, the medical device comprising:
a first housing portion adapted to be carried by a user;
a second housing portion configured to be selectively operatively engaged with and disengaged from the first housing portion;
a reservoir connected to one of the first and second housing portions;
at least one of a drive device or a needle inserting device supported by the other of the first and second housing portions relative to the respective housing portion to which the reservoir is connected, such that upon the first and second housing portions being operatively engaged, the reservoir is operatively coupled to at least one of the drive device or the needle inserting device;
a first magnet supported on the first housing portion; and
a second magnet supported on the second housing portion in a position to magnetically interact with the first magnet upon the first and second housing portions being improperly aligned when brought toward each other for operative engagement;
wherein each of the first magnet and the second magnet has a pole that faces a pole of the other of the first magnet and the second magnet when the first and second housing portions are improperly aligned when brought toward each other for operative engagement; and
wherein the facing poles of the first magnet and the second magnet are of the same polarity such that the first magnet and second magnet mutually repel each other upon the first and second housing portions being improperly aligned when brought toward each other for operative engagement.

20. A medical device for delivering an infusion medium to a user, the medical device comprising:
a first housing portion adapted to be carried by a user;
a second housing portion configured to be selectively operatively engaged with and disengaged from the first housing portion;
a reservoir supported by one of the first and second housing portions;
at least one of a drive device or a needle inserting device supported by the other of the first and second housing portions relative to the respective housing portion that supports the reservoir, such that upon the first and second housing portions being operatively engaged, the reservoir is operatively coupled to at least one of the drive device and the needle inserting device;
a first magnet supported on the first housing portion; and
a second magnet supported on the second housing portion in a position to repel the first magnet upon the first and second housing portions being improperly aligned when brought toward each other for operative engagement.

* * * * *